(12) United States Patent
Wantanabe et al.

(10) Patent No.: US 6,838,483 B2
(45) Date of Patent: Jan. 4, 2005

(54) SULFONATED AMINO ACID DERIVATIVES AND METALLOPROTEINASE INHIBITORS CONTAINING THE SAME

(75) Inventors: Fumihiko Wantanabe, Nara (JP); Hiroshige Tsuzuki, Kyoto (JP); Mitsuaki Ohtani, Nara (JP)

(73) Assignee: Shionogi & Co., Ltd., Osaka (JP)

( * ) Notice: Subject to any disclaimer, the term of this patent is extended or adjusted under 35 U.S.C. 154(b) by 150 days.

(21) Appl. No.: 10/290,245

(22) Filed: Nov. 8, 2002

(65) Prior Publication Data

US 2003/0225043 A1 Dec. 4, 2003

Related U.S. Application Data

(63) Continuation of application No. 09/120,383, filed on Jul. 22, 1998, which is a continuation of application No. PCT/JP96/00126, filed on Jan. 22, 1997.

(30) Foreign Application Priority Data

Jan. 23, 1996 (JP) .............................................. 8-30082
Aug. 13, 1996 (JP) ............................................ 8-213555

(51) Int. Cl.$^7$ .......................................... A61K 31/195
(52) U.S. Cl. ....................... 514/562; 514/604; 562/430; 564/85
(58) Field of Search ........................... 564/85; 562/430; 514/562, 604

(56) References Cited

U.S. PATENT DOCUMENTS

| | | | |
|---|---|---|---|
| 3,784,701 A | 1/1974 | Tomcufcik et al. |
| 4,269,775 A | 5/1981 | Szczepanski et al. |
| 4,388,464 A | 6/1983 | Kristinsson et al. |
| 4,599,361 A | 7/1986 | Dickens et al. |
| 4,632,931 A | 12/1986 | Nakane |
| 4,715,883 A | 12/1987 | Lukaszczyk et al. |
| 5,270,326 A | 12/1993 | Galardy et al. |
| 5,854,277 A | 12/1998 | Kluender et al. |
| 6,150,394 A | 11/2000 | Watanabe et al. |
| 6,207,698 B1 | 3/2001 | Wantanabe et al. |
| 6,235,768 B1 | 5/2001 | Wantanabe et al. |
| 6,441,021 B1 | 8/2002 | Wantanabe et al. |

FOREIGN PATENT DOCUMENTS

| | | |
|---|---|---|
| EP | 0 305 947 A1 | 3/1989 |
| EP | 0 468 231 A2 | 1/1992 |
| EP | 0 548 798 A1 | 6/1993 |
| EP | 0 606 046 B1 | 7/1994 |
| JP | 57-59969 | 4/1982 |
| WO | WO 14069 | 7/1993 |
| WO | WO 94/12181 A1 | 6/1994 |
| WO | WO 95/13289 A1 | 5/1995 |
| WO | WO 35276 | 12/1995 |
| WO | WO 95/35275 A1 | 12/1995 |
| WO | WO 95/35276 A1 | 12/1995 |
| WO | WO 00214 | 1/1996 |
| WO | WO 96/00214 A1 | 1/1996 |
| WO | WO 96/11209 A1 | 4/1996 |
| WO | WO 96/15096 A1 | 5/1996 |
| WO | WO 97/27174 A1 | 7/1997 |

OTHER PUBLICATIONS

Qi–Zhuang Ye et al., Purification and Characterization of the Human Stromelysin Catalytic Domain Expressed in *Escherichia coli*, Biochemistry, Sep. 3, 1992, pp. 11231–11235, vol. 31–Issue No. 45, American Chemical Society.

Kevin T. Chapman et al., Inhibition of Matrix Metalloproteinases by N–Carboxyalkyl Peptides, Journal of Medicinal Chemistry, Apr. 26, 1993, pp. 4293–4301, vol. 36–Issue No. 26, American Chemical Society.

Debnath A.K., et al., "4–(4–Substituted benzoyl) aminobenzenesulphonyl–L(–)glutamic acids and 5–N–Substituted – 2–[4'–(4"–substituted benzyol)aminobenzenesulphonyl]–L–glutamines as potential antineoplastic agents; Synthesis, biological evaluation and quantitative structure–activity relationsip studies," Indian J. of Chem., 1989, pp 843–847, vol. 288.

Galli, B., et al., "Enantiomeric separation of dansyl–and dabsylamino acids by ligand–exchange chromatography with (*S*)– and (*R*)–phenylalaninamide–modified silica gel," J. of Chroma., 1994, pp. 77–89, A.666.

Hansel J., et al., "Oxazoline Formation via a Palladium–catalyzed Cyclization: A direct, Stereoselective to *cis*–5–amino–2–cyclopenten–1–ol Derivatives," 1995, Tetrahedron Letters, pp. 2913–2916, vol. 36, No. 17.

Hlavacek, J., et al, "an alternative Route to $N^\alpha$–Methylamino Acid Derivatives: Synthesis and Conformation of Some $N^\alpha$–Acetyl– $N^\alpha$–Methylamino Acid Methylamides," 1988, Collect. Czechoslovak Chem. Commun., vol. 53.

Kaiser, C., et al., "2–Substituted Derivatives of 3,4–Dihydroxyphenylalanine," 1957, pp. 4365–4370, vol. 79.

Lin, J., et al., "Debsyl Chloride: Its Synthesis, Characterization and Application in Amino Acid and Amine Microanalysis," J. of the Chinese Biochem. Soc., 1985, pp. 10–19, vol. 14, no. 1.

(List continued on next page.)

*Primary Examiner*—Samuel Barts
(74) *Attorney, Agent, or Firm*—Foley & Lardner LLP

(57) ABSTRACT

Compounds having a metalloproteinase inhibitory activity, represented by the formula (I), its optically active isomers, their pharmaceutically acceptable salts, or hydrates thereof.

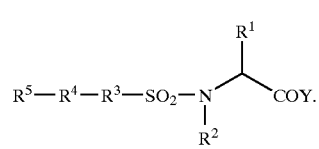

11 Claims, No Drawings

OTHER PUBLICATIONS

Natelson, S., et al., "Preparation of D–, DL–, and L–Homoserine Lactone from Methionine,". Microchem. Journ., 1989, pp. 226–232, vol. 40.

Nickel, P., et al., "Carboxylic acid analogues of suramin, potential filaricides," Indian Journal of Chemistry, 1991, pp. 182–187, vol. 30B.

Stocchi, V., et al., "Reversed–Phase High Performance Liquid Chromatography Separation of Dimethylaminoazobenzene Sulfonyl–and Dimethylaminoazobenzene Thiohydantoin–Amino Acid Derivatives for Amino Acid Analysis and Microsequencing Studies at the Picomole Level," Analyt. Biochem., 1989, pp. 107–117, vol. 178.

Verderame, M., et al., "Sulfide Derivatives of Cysteine II," Journal of Pharma. Sci., 1962, pp 576–579, vol. 51.

Yoneda, N., et al., "Reactions of L–$\alpha$–Tosylamido–$\beta$–propiolactone. I. Synthesis, Reactions with Amines and Derivation to L–Serine," UDC, 1969, pp. 98–103, vol. 89, no. 1.

SULFONATED AMINO ACID DERIVATIVES AND METALLOPROTEINASE INHIBITORS CONTAINING THE SAME

This application is a continuation of application Ser. No. 09/120,383, filed Jul. 22, 1998, which is a continuation of International Application PCT/JP96/00126, filed Jan. 22, 1997, which claims priority to Japanese Patent Application Nos. 8/30082, filed Jan. 23, 1996, and 8/213555, filed Aug. 13, 1996, the disclosures of which are incorporated herein by reference in their entirety.

TECHNICAL FIELD

This application relates to sulfonated amino acid derivatives and metalloproteinase inhibitors containing the same.

BACKGROUND ART

An extracellular matrix consists of collagen, proteoglycan, etc., has a function to support tissues, and plays a role in a maintaining of a cell functions, for example propagation, differentiation, adhesion, or the like. Matrix metalloproteinases (MMP) such as gelatinase, stromelysin, collagenase, and the like have an important role in degradation of an extracellular matrix, and these enzymes work for growth, tissue remodeling, etc. under physiological conditions. Therefore, it is considered that these enzymes participate in progression of various kind of diseases involving breakdown and fibrosis of tissues, such as osteoarthritis, rheumatoid arthritis, corneal ulceration, periodontitis, metastasis and invasion of tumor, and virus infection (for example, HIV infection). At the present time, it is not clear which enzyme participates in the above diseases seriously, but it is considered that these enzymes at least participate in tissue breakdown. As metalloproteinase inhibitors of amino acid derivatives, for example hydroxamic acid derivatives of amino acids (JP-A-6-2562939), carboxylic acid derivatives of amino acid and/or their hydroxamic acid derivatives (WO95/35276), etc. are disclosed.

DISCLOSURE OF INVENTION

If it is able to inhibit the activity of MMP, it is considered that MMP inhibitors contribute to an improvement and prevention of the above diseases caused by or related to its activity. Therefore, development of MMP inhibitors has long been desired.

In the above situation, the inventors of the present invention found that a kind of sulfonamide derivatives have strong activity to inhibit MMP.

The present invention relates to a composition for inhibiting metalloproteinase which contains a compound of the formula I:

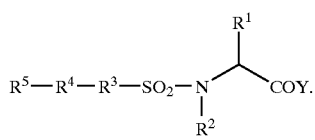

I wherein $R^1$ is optionally substituted lower alkyl, optionally substituted aryl, optionally substituted aralkyl, optionally substituted heteroaryl, or optionally substituted heteroarylalkyl; $R^2$ is hydrogen atom, optionally substituted lower alkyl, optionally substituted aryl, optionally substituted aralkyl, optionally substituted heteroaryl, or optionally substituted heteroarylalkyl; $R^3$ is a bond, optionally substituted arylene, or optionally substituted heteroarylene; $R^4$ is a bond, —$(CH_2)m$-, —CH=CH—, —C≡C—, —CO—, —CO—NH—, —N=N—, —N($R^A$)—, —NH—CO—NH—, —NH—CO—, —O—, —S—, —$SO_2$NH—, —$SO_2$—NH—N=CH—, or tetrazol-diyl; $R^5$ is optionally substituted lower alkyl, optionally substituted $C_3$–$C_8$ cycloalkyl, optionally substituted aryl, optionally substituted heteroaryl, or an optionally substituted non-aromatic heterocyclic group; $R^A$ is hydrogen atom or lower alkyl; Y is —NHOH or —OH; and m is 1 or 2; provided $R^2$ is hydrogen atom when Y is —NHOH, its optically active substance, their pharmaceutically acceptable salt, or hydrate thereof.

Mentioned in more detail, the invention relates to the following a)–b), 1)–16), and A)–C).

a) A composition for inhibiting metalloproteinase which contains a compound of the formula I:

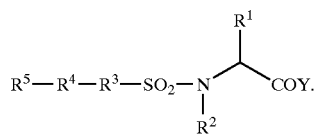

I wherein $R^1$ is optionally substituted lower alkyl, optionally substituted aryl, optionally substituted aralkyl, optionally substituted heteroaryl, or optionally substituted heteroarylalkyl; $R^2$ is hydrogen atom, optionally substituted lower alkyl, optionally substituted aryl, optionally substituted aralkyl, optionally substituted heteroaryl, or optionally substituted heteroarylalkyl; $R^3$ is a bond, optionally substituted arylene, or optionally substituted heteroarylene; $R^4$ is a bond, —$(CH_2)m$-, —CH=CH—, —C≡C—, —CO—, —CO—NH—, —N=N—, —N($R^A$)—, —NH—CO—NH—, —NH—CO—, —O—, —S—, —$SO_2$NH—, —$SO_2$—NH—N=CH—, or tetrazol-diyl; $R^5$ is optionally substituted lower alkyl, optionally substituted $C_3$–$C_8$ cycloalkyl, optionally substituted aryl, optionally substituted heteroaryl, or an optionally substituted non-aromatic heterocyclic group; $R^A$ is hydrogen atom or lower alkyl; Y is —NHOH or —OH; and m is 1 or 2; provided $R^2$ is hydrogen atom when Y is —NHOH, $R^5$ is optionally substituted aryl or optionally substituted heteroaryl when $R^3$ is optionally substituted arylene or optionally substituted heteroarylene and $R^4$ is —CO—NH— or —NH—CO—, $R^5$ is optionally substituted aryl or optionally substituted heteroaryl when $R^3$ is optionally substituted arylene or optionally substituted heteroarylene and $R^4$ is tetrazol-diyl, $R^5$ is lower alkyl, aryl substituted by lower alkyl or optionally substituted aryl, or heteroaryl substituted by lower alkyl or optionally substituted aryl when $R^3$ is optionally substituted arylene and $R^4$ is a bond, both of $R^3$ and $R^4$ are not a bond at the same time, and $R^4$ is not —O— when $R^3$ is optionally substituted arylene or optionally substituted heteroarylene, its optically active substance, their pharmaceutically acceptable salt, or hydrate thereof.

b) A composition for inhibiting metalloproteinase as mentioned above, which is a composition for inhibiting type-IV collagenase.

Preferred embodiment of the present invention are as follows.

1) A compound of the formula I:

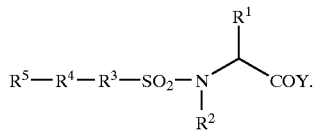

wherein $R^1$ is optionally substituted lower alkyl, optionally substituted aryl, optionally substituted aralkyl, optionally substituted heteroaryl, or optionally substituted heteroarylalkyl; $R^2$ is hydrogen atom, optionally substituted lower alkyl, optionally substituted aryl, optionally substituted aralkyl, optionally substituted heteroaryl, or optionally substituted heteroarylalkyl; $R^3$ is a bond, optionally substituted arylene, or optionally substituted heteroarylene; $R^4$ is a bond, —(CH$_2$)m-, —CH=CH—, —C≡C—, —CO—, —CO—NH—, —N=N—, —N(R$^A$)—, —NH—CO—NH—, —NH—CO—, —O—, —S—, —SO$_2$NH—, —SO$_2$—NH—N=CH—, or tetrazol-diyl; $R^5$ is optionally substituted lower alkyl, optionally substituted $C_3$–$C_8$ cycloalkyl, optionally substituted: aryl, optionally substituted heteroaryl, or an optionally substituted non-aromatic heterocyclic group; $R^A$ is hydrogen atom or lower alkyl; Y is —NHOH or —OH; and m is 1 or 2; provided $R^2$ is hydrogen atom when Y is —NHOH, $R^5$ is optionally substituted aryl or optionally substituted heteroaryl when $R^3$ is optionally substituted arylene or optionally substituted heteroarylene and $R^4$ is —CO—NH— or —NH—CO— (when $R^3$ is phenylene and $R^4$ is —CO—NH—, $R^1$ is not methyl or phenyl and $R^5$ is not 2-chlorophenyl, 4-chlorophenyl, or 2,4-dichlorophenyl), $R^5$ is lower alkyl, optionally substituted aryl, or optionally substituted heteroaryl when $R^3$ is optionally substituted arylene or optionally substituted heteroarylene and $R^4$ is tetrazol-diyl, $R^5$ is lower alkyl, aryl substituted with lower alkyl or optionally substituted aryl, or heteroaryl substituted with lower alkyl or optionally substituted aryl when $R^3$ is optionally substituted arylene and $R^4$ is a bond, both of $R^3$ and $R^4$ are not a bond at the same time, and $R^4$ is not —O— when $R^3$ is optionally substituted arylene or optionally substituted heteroarylene, its optically active substance, their pharmaceutically acceptable salt, or hydrate thereof.

2) A compound of the formula II:

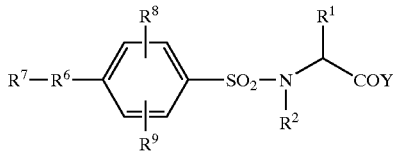

wherein $R^6$ is —CH=CH—, —C≡C—, —N=N—, —NH—CO—NH—, —S—, —SO$_2$NH—, or —SO$_2$—NH—N=CH—; $R^7$ is optionally substituted aryl or optionally substituted heteroaryl; $R^8$ and $R^9$ are each independently hydrogen atom, lower alkoxy, or nitro; $R^1$, $R^2$, and Y are as defined above, its optically active substance, their pharmaceutically acceptable salt, or hydrate thereof.

3) A compound of the formula III:

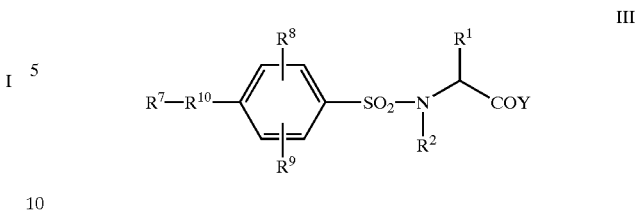

wherein $R^{10}$ is —(CH$_2$)m-, —CO—, —CO—NH—, —N(R$^A$)—, —NHCO—, or tetrazol-diyl; m is 1 or 2; $R^1$, $R^2$, $R^7$, $R^8$, $R^9$, $R^A$, and Y are as defined above, provided $R^1$ is not methyl or phenyl and $R^7$ is not 2-chlorophenyl, 4-chlorophenyl, or 2,4-dichlorophenyl when $R^{10}$ is —NH—CO—, its optically active substance, their pharmaceutically acceptable salt, or hydrate thereof.

4) A compound of the formula IV:

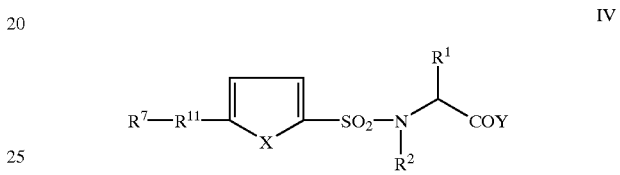

wherein $R^{11}$ is a bond, —CH=CH—, or —C≡C—; X is oxygen atom or sulfur atom, $R^1$, $R^2$, $R^7$, and Y are as defined above, its optically active substance, their pharmaceutically acceptable salt, or hydrate thereof.

5) A compound of the formula I':

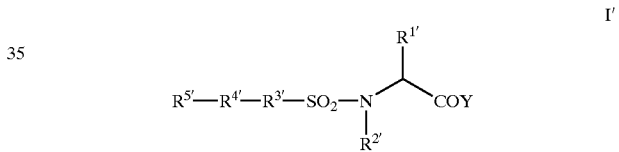

wherein $R^{1'}$ is benzyl, (indol-3-yl)methyl, (1-methylindol-3-yl)methyl, (5-methylindol-3-yl)methyl, (1-acetylindol-3-yl)methyl, (1-methylsulfonylindol-3-yl)methyl, (1-alkoxycarbonyl-3-yl)methyl (for example ethoxycarbonylmethyl), or i-propyl; $R^{2'}$ is hydrogen atom, methyl, 4-aminobutyl, or benzyl; $R^{3'}$ is 1,4-phenylene; $R^{4'}$ is —O—; $R^{5'}$ is phenyl or 4-hydroxy-phenyl; and Y is as defined above, its optically active substance, their pharmaceutically acceptable salt, or hydrate thereof.

6) A compound of the formula I":

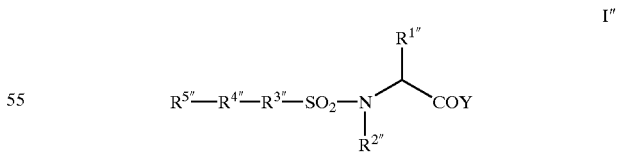

wherein $R^{1''}$ is 4-thiazolylmethyl, (indol-3-yl)methyl, (5-methoxyindol-3-yl)methyl, 1-naphthylmethyl, 2-naphthylmethyl, 4-biphenylylmethyl, 2,2,2-trifluoroethyl, 2-phenylethyl, benzyl, i-propyl, 4-nitrobenzyl, 4-fluorobenzyl, cyclohexylmethyl, (1-methylindol-3-yl)methyl, (5-methylindol-3-yl)methyl, (5-fluoroindol-3-yl)methyl, (pyridin-4-yl)methyl, (benzothiazol-2-yl)methyl, (phenyl)(hydroxy)methyl, phenyl, carboxymethyl, 2-carboxyethyl, hydroxymethyl, phenylmethoxymethyl, 4-carboxybenzyl, (benzimidazol-2-yl)methyl, (1-methyl-sulfonylindol-3-yl)methyl, or (1-ethoxycarbonylindol-3-yl)methyl; $R^{2'''}$ is hydrogen atom; $R^{3'''}$ is 1,4-phenylene; $R^{4'''}$ is a bond; $R^{5'''}$ is phenyl, 3-methoxyphenyl, 4-methoxyphenyl, 4-methylphenyl, 4-tert-butylphenyl, 4-trifluoromethyl-phenyl, 4-fluorophenyl, 4-methylthiophenyl, 4-biphenylyl, 2-thienyl, benzoxazol-2-yl, benzothiazol-2-yl, or tetrazol-2-yl; and Y is as defined above, its optically active substance, their pharmaceutically acceptable salt, or hydrate thereof.

7) A compound of the formula V:

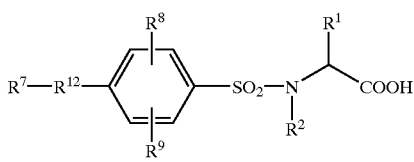

V wherein $R^{12}$ is —CH═CH— or —C≡C—; $R^1$, $R^2$, $R^7$, $R^8$, and $R^9$ are as defined above, its optically active substance, their pharmaceutically acceptable salt, or hydrate thereof.

8) A compound of the formula VI:

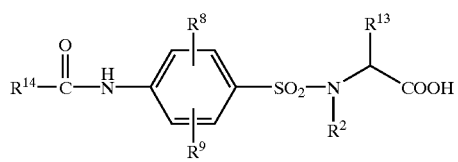

VI wherein $R^2$, $R^8$, and $R^9$ are as defined above, $R^{13}$ is optionally substituted lower alkyl, optionally substituted aryl, optionally substituted aralkyl, optionally substituted heteroaryl, or optionally substituted heteroarylalkyl; and $R^{14}$ is optionally substituted aryl, or optionally substituted heteroaryl; provided $R^{13}$ is not methyl or phenyl and $R^{14}$ is not 2-chlorophenyl, 4-chlorophenyl, or 2,4-dichlorophenyl, its optically active substance, their pharmaceutically acceptable salt, or hydrate thereof.

9) A compound of the formula VII:

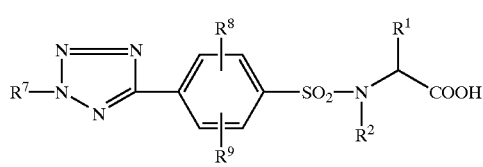

VII wherein $R^1$, $R^2$, $R^7$, $R^8$, and $R^9$ are as defined above, its optically active substance, their pharmaceutically acceptable salt, or hydrate thereof.

10) A compound of the formula VIII:

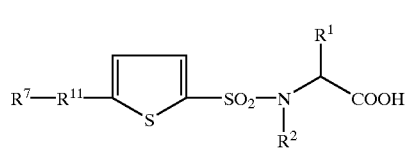

VIII wherein $R^1$, $R^2$, $R^7$, and $R^{11}$ are as defined above, its optically active substance, their pharmaceutically acceptable salt, or hydrate thereof.

11) A compound of the formula VIII:

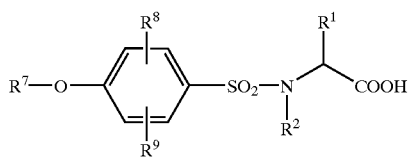

IX wherein $R^1$, $R^2$, $R^7$, $R^8$, and $R^9$ are as defined above, its optically active substance, their pharmaceutically acceptable salt, or hydrate thereof.

12) A compound of the formula X:

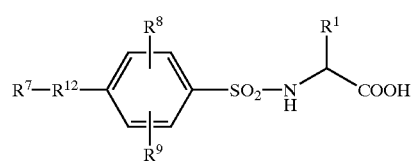

X wherein $R^{12}$ is —CH═CH— or —C≡C—; $R^1$, $R^7$, $R^8$, and $R^9$ are as defined above, its optically active substance, their pharmaceutically acceptable salt, or hydrate thereof.

13) A compound of the formula XI:

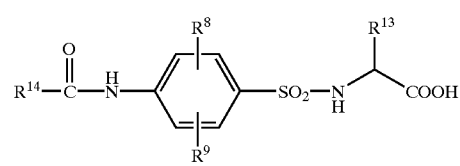

XI wherein $R^8$, $R^9$, $R^{13}$, and $R^{14}$ are as defined above, provided $R^{13}$ is not methyl or phenyl and $R^{14}$ is not 2-chlorophenyl, 4-chlorophenyl, or 2,4-dichlorophenyl, its optically active substance, their pharmaceutically acceptable salt, or hydrate thereof.

14) A compound of the formula XII:

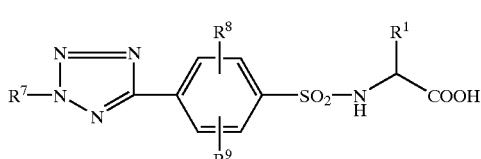

XII wherein $R^1$, $R^7$, $R^8$, and $R^9$ are as defined above, its optically active substance, their pharmaceutically acceptable salt, or hydrate thereof.

15) A compound of the formula XIII:

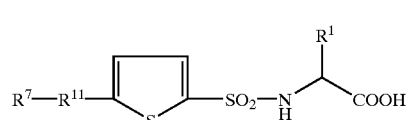

XIII wherein $R^1$, $R^7$, and $R^{11}$ are as defined above, its optically active substance, their pharmaceutically acceptable salt, or hydrate thereof.

16) A compound of the formula XIV:

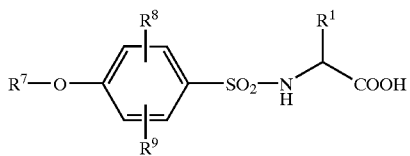

wherein $R^1$, $R^7$, $R^8$, and $R^9$ are as defined above, its optically active substance, their pharmaceutically acceptable salt, or hydrate thereof.

A compound of the invention is more specifically illustrated below:

A) The compound of any one of above 1) to 16), wherein $R^1$, $R^{1'}$, $R^{1''}$, and $R^{13}$ are i-propyl, benzyl, or (indol-3-yl) methyl.

B) The compound of any one of above 1) to 4) and 7) to 16), wherein $R^5$, $R^7$, and $R^{14}$ are phenyl optionally substituted with one or more substituents selected from the group consisting of alkoxy, alkylthio, and alkyl.

C) The compound of any one of above 1) to 16), wherein a configuration of asymmetric carbon atoms bonding with $R^1$, $R^{1'}$, $R^{1''}$, and $R^{13}$ is R configuration.

Further, this invention relates to a pharmaceutical composition, a composition for inhibiting metalloproteinase, and a composition for inhibiting type IV collagenase which contain the compound above 1) to 16) and A) to C)

All of compounds of above 1) to 16) and A) to C) have strong metalloproteinase inhibitory activity, and the following compound is more preferable:

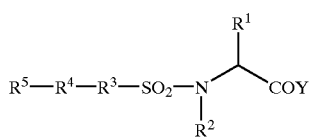

1) A compound wherein $R^1$ is i-propyl, benzyl, or (indol-3-yl) methyl, $R^2$ is hydrogen atom, $R^3$ is 1,4-phenylene, $R^4$ is —C≡C—, and $R^5$ is optionally substituted phenyl.

2) A compound wherein $R^1$ is i-propyl, benzyl, or (indol-3-yl) methyl, $R^2$ is hydrogen atom, $R^3$ is optionally substituted 2,5-thiophen-diyl, $R^4$ is —C≡C—, and $R^5$ is optionally substituted phenyl.

3) A compound wherein $R^1$ is i-propyl, benzyl, or (indol-3-yl)methyl, $R^2$ is hydrogen atom, $R^3$ is 1,4-phenylene, $R^4$ is tetrazol-diyl, and $R^5$ is optionally substituted phenyl.

The term "alkyl" herein used means $C_1$–$C_{10}$ straight or branched chain alkyl, for example, methyl, ethyl, n-propyl, i-propyl, n-butyl, i-butyl, sec-butyl, tert-butyl, n-pentyl, i-pentyl, neo-pentyl, tert-pentyl, and the like.

The term "lower alkyl" herein used means $C_1$–$C_6$ straight or branched chain alkyl, for example, methyl, ethyl, n-propyl, i-propyl, n-butyl, i-butyl, sec-butyl, tert-butyl, and the like.

The term "$C_3$–$C_8$ cycloalkyl" herein used is exemplified by cyclopropyl, cyclobutyl, cyclopentyl, cyclohexyl, cycloheptyl, and the like.

The term "aryl" herein used means monocyclic or condensed ring aromatic hydrocarbons. Examples of the aryl are phenyl, naphthyl, and the like.

The term "aralkyl" herein used means the above mentioned alkyl substituted by the above mentioned aryl at any possible position. Examples of the aralkyl are benzyl, phenethyl, phenylpropyl (e.g., 3-phenylpropyl), naphthylmethyl (α-naphthylmethyl), anthrylmethyl (9-anthrylmethyl), and the like. Benzyl is preferred. The aryl part may optionally be substituted.

The term "heteroaryl" herein used means a 5 to 6 membered aromatic heterocyclic group which contains one or more hetero atoms selected from the group consisting of nitrogen, oxygen and sulfur atoms in the ring and may be fused with a carbocyclic ring or other heterocyclic ring at any possible position. Examples of the heteroaryl are pyrrolyl (e.g., 1-pyrrolyl), indolyl (e.g., 2-indolyl), carbazolyl (e.g., 3-carbazolyl), imidazolyl (e.g., 4-imidazolyl), pyrazolyl (e.g., 1-pyrazolyl), benzimidazolyl (e.g., 2-benzimidazolyl), indazolyl (e.g., 3-indazolyl), indolizinyl (e.g., 6-indolizinyl), pyridyl (e.g., 4-pyridyl), quinolyl (e.g., 5-quinolyl), isoquinolyl (e.g., 3-isoquinolyl), acridinyl (e.g., 1-acridinyl), phenanthridinyl (e.g., 2-phenanthridinyl), pyridazinyl (e.g., 3-pyridazinyl), pyrimidinyl (e.g., 4-pyrimidinyl), pyrazinyl (e.g., 2-pyrazinyl), cinnolinyl (e.g., 3-cinnolinyl), phthalazinyl (e.g., 2-phthalazinyl), quinazolinyl (e.g., 2-quinazolinyl), isoxazolyl (e.g., 3-isoxazolyl), benzisoxazolyl (e.g., 3-benzisoxazolyl), oxazolyl (e.g., 2-oxazolyl), benzoxazolyl (e.g., 2-benzoxazolyl), benzoxadiazolyl (e.g., 4-benzoxadiazolyl), isothiazolyl (e.g., 3-isothiazolyl), benzisothiazolyl (e.g., 2-benzisothiazolyl), thiazolyl (e.g., 2-thiazolyl), benzothiazolyl (e.g., 2-benzothiazolyl), furyl (e.g., 3-furyl), benzofuryl (e.g., 3-benzofuryl), thienyl (e.g., 2-thienyl), benzothienyl (e.g., 2-benzothienyl), tetrazolyl, and the like. The aryl part of the above heteroaryl is optionally substituted.

The term "heteroarylalkyl" herein used means the above mentioned alkyl substituted with the above mentioned heteroaryl at any possible position. Examples of the heteroarylalkyl are thiazolylmethyl (e.g., 4-thiazolylmethyl), thiazolylethyl (e.g., 5-thiazolyl-2-ethyl), indolylmethyl (e.g., 2-indolylmethyl), imidazolylmethyl (e.g., 4-imidazolylmethyl), benzothiazolylmethyl (e.g., 2-benzothiazolylmethyl), benzopyrazolylmethyl (e.g., 1-benzopyrazolylmethyl), benzotriazolylmethyl (e.g., 4-benzotriazolylmethyl), benzoquinolylmethyl (e.g., 2-benzoquinolylmethyl), benzimidazolylmethyl (e.g., 2-benzimidazolylmethyl), pyridylmethyl (e.g., 2-pyridylmethyl), and the like. The aryl part of the above heteroaryl is optionally substituted.

The term "arylene" herein used is exemplified by phenylene, naphthylene, and the like. Mentioned in more detail, it is exemplified by 1,2-phenylene, 1,3-phenylene, 1,4-phenylene, and the like.

The term "heteroarylene" herein used is exemplified by thiophen-diyl, furan-diyl, pyridin-diyl, and the like, in more detail, by 2,5-thiophen-diyl, 2,5-furan-diyl, and the like.

The term "non-aromatic heterocyclic group" herein used means 5 to 6 membered non-aromatic heterocyclic group which contains one or more hetero atoms selected from the group consisting of nitrogen, oxygen and sulfur atoms in the ring, and may bind at any possible positin. Examples of the non-aromatic heterocyclic group are morpholino, piperidino, pyrrolidino, and the like.

The term "alkoxy" herein used means alkoxy of which alkyl part is the above mentioned alkyl. Examples of the alkoxy are methoxy, ethoxy, propoxy, butoxy, pentyloxy, and the like.

The term "lower alkoxy" herein used means alkoxy of which alkyl part is the above mentioned lower alkyl.

Examples of the lower alkoxy are methoxy, ethoxy, n-propoxy, i-propoxy, n-butoxy, i-butoxy, sec-butoxy, tert-butoxy, and the like.

The term "halogen" herein used means fluoro, chloro, bromo, and iodo.

The term "alkylthio" herein used means alkylthio whose alkyl part is the above mentioned lower alkyl. Examples of the alkylthio are methylthio, ethylthio, and the like.

Substituents for "optionally substituted alkyl", "optionally substituted $C_3$–$C_8$ cycloalkyl", and "optionally substituted non-aromatic heterocyclic group" are hydroxy, alkoxy (e.g., methoxy and ethoxy), mercapto, alkylthio (e.g., methylthio), cycloalkyl (e.g., cyclopropyl, cyclobutyl, cyclopentyl, and cyclohexyl), halogen (e.g., fluoro, chloro, bromo, and iodo), carboxy, alkoxycarbonyl (e.g., methoxycarbonyl and ethoxycarbonyl), nitro, cyano, haloalkyl (e.g., trifluoromethyl), substituted or unsubstituted amino (e.g., methylamino, dimethylamino, and carbamoylamino), guanidino, phenyl, benzyloxy, and the like. These substituents are able to bind them at one or more of any possible positions.

Substituents for the aromatic ring of "optionally substituted aryl", "optionally substituted aralkyl", "optionally substituted heteroaryl", "optionally substituted heteroarylalkyl", "optionally substituted arylene", and "optionally substituted heteroarylene" are, for example, hydroxy, alkoxy (e.g., methoxy and ethoxy), mercapto, alkylthio (e.g., methylthio), cycloalky (e.g., cyclopropyl, cyclobutyl, cyclopentyl), halogen (e.g., fluoro, chloro, bromo, and iodo), carboxy, alkoxycarbonyl (e.g., methoxycarbonyl and ethoxycarbonyl), nitro, cyano, haloalkyl (e.g., trifluoromethyl), aryloxy (e.g., phenyloxy) substituted or unsubstituted amino (e.g., methylamino, dimethylamino, diethylamino, and benzylidenamino), guanidino, alkyl (e.g., methyl, ethyl, n-propyl, i-propyl, n-butyl, i-butyl, sec-butyl, tert-butyl, n-pentyl, i-pentyl, neo-pentyl, and tert-pentyl), alkenyl (e.g., vinyl and propenyl), alkynyl (e.g., ethynyl and phenylethynyl), alkanoyl (e.g., formyl, acetyl, and propionyl), acyloxy (e.g., acetyloxy), acylamino, alkylsulfonyl (e.g., methylsulfonyl), phenyl, benzyl, an azo group (e.g., phenylazo), optionally substituted heteroaryl (e.g., 3-pyridyl), optionally substituted ureido (e.g., ureido and phenylureido), and the like. These substituents are able to bind to it at one or more of any possible position.

BEST MODE FOR CARRYING OUT THE INVENTION

Compounds (Ia) and (Ib) of the invention are able to be synthesized from the corresponding α-amino acids represented by the formula (XV) by means of the following 6 synthetic methods. Generally, it is possible to produce the compounds of the invention by means of the method A. Each classified type of the compounds is possible to be produced by means of methods the B to F. However, these methods are only examples to produce the compounds represented by the formula I. A compound represented by the formula I produced by any other method is included in this invention.

Method A: A general synthetic method of the compound represented by the formula I.

Method B: A synthetic method of the compound wherein and $R^3$ is optionally substituted arylene or optionally substituted heteroarylene, $R^4$ is —C≡C—, and $R^5$ is optionally substituted aryl or optionally substituted heteroaryl.

Method C: A synthetic method of the compound wherein $R^3$ is optionally substituted arylene or optionally substituted heteroarylene, $R^4$ is a bond, and $R^5$ is optionally substituted aryl or optionally substituted heteroaryl.

Method D: A synthetic method of the compound wherein $R^3$ is optionally substituted arylene or optionally substituted heteroarylene, $R^4$ is —CO—NH—, and $R^5$ is optionally substituted aryl or optionally substituted heteroaryl.

Method E: A synthetic method of the compound wherein $R^3$ is optionally substituted arylene or optionally substituted heteroarylene, $R^4$ is tetrazol-diyl, and $R^5$ is optionally substituted aryl or optionally substituted heteroaryl.

Method F: A synthetic method of the compound wherein $R^3$ is optionally substituted arylene or optionally substituted heteroarylene, $R^4$ is —CH═CH—, and $R^5$ is optionally substituted aryl or optionally substituted heteroaryl.

Details of these methods are explained as follows.
(Method A)

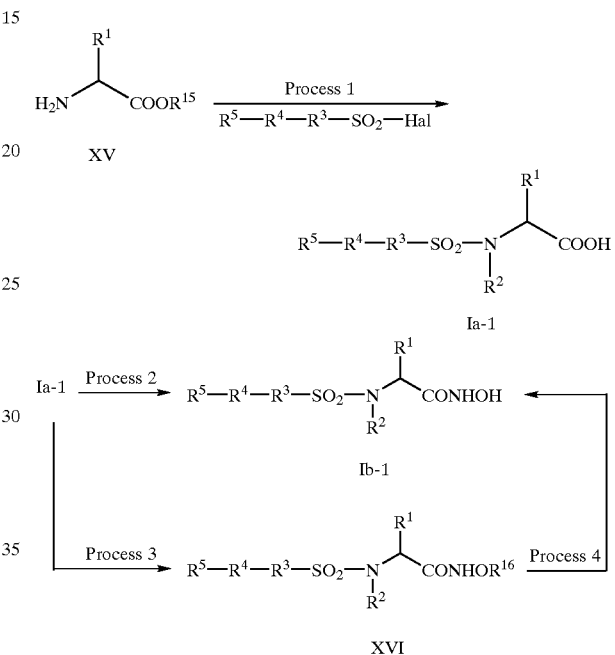

wherein $R^1$, $R^2$, $R^3$, $R^4$, and $R^5$ are as defined above, $R^{15}$ is hydrogen atom or a carboxy protective group, $R^{16}$ is a hydroxy protective group, and Hal is halogen.

Conversion of compound (XV) to compound (Ia-1) is sulfonation of an amino group of the compound (XV) (process 1). If necessary, after this reaction, N-alkylation, deprotection of a carboxyl protective group, etc. are carried out. Conversion of compound (Ia-1) to compound (Ib-1) is to obtain hydroxamic acid derivatives from carboxylic acid derivatives (process 2). To obtain compound (Ib-1) from compound (Ia-1), compound (Ia-1) may also be reacted with hydroxylamine having a hydroxyl protective group or its acidic salts to give compound (XVI) (process 3), followed by and deprotection (process 4). Conversion to sulfonyl derivatives and hydroxamic acid derivatives are able to be carried out according to an usual method. For example, an amino acid represented by the formula (XV) is reacted with a sulfonating agent such as sulfonyl halide represented by $R^5$—$R^4$—$R^3$—$SO_2$Hal ($R^3$, $R^4$, and $R^5$ are as defined above; and Hal is halogen) and then hydroxylamine. Each process will hereinafter be described in more detail.
(Process 1)

Some of amino acids represented by the formula (XV) or its acidic salts (e.g., hydrochloride, p-toluenesulfonate, and trifluoroacetate) which are starting materials are commercially available. The other are able to be synthesized in accordance with a method described in Zikkenkagakukoza, vol. 22, IV (nihonkagakukai), J. Med. Chem. 38, 1689–1700, 1995, Gary M. Ksander et. al., etc. some of sulfonating agents are commercially available and the other are synthesized in accordance with a method described Shin-zikkenkagakukoza, vol. 14, 1787, 1978, Synthesis 852–854, 1986, etc. A carboxyl protective group is exemplified by esters (e.g., methyl ester, tert-butyl ester and benzyl ester). Deprotection of this protective group may be carried out by hydrolysis with acid (e.g., hydrochloride and trifluoroacetic acid) or base (e.g., sodium hydroxide) depending on the type of the group, or by catalytic reduction, e.g., under 10% palladium-carbon catalyst condition. To obtain a compound (Ib-1), the esters may directly be converted to hydroxamic acid by the method of process 2. When a compound (XV) is an amino acid wherein $R^{15}$ is hydrogen atom, preferable solvents for this sulfonylation are dimethylformamide, tetrahydrofuran, dioxane, dimethylsulfoxide, acetonitrile, water, or mixed solvents thereof. When a compound (XV) is an amino acid wherein $R^{15}$ is a protective group such as an ester, a solvent for this sulfonylation is exemplified by the above solvents and mixed solvents of water-insoluble solvents (e.g., benzene and dichloromethane) and the above solvents. A base to be used in this sulfonylation is exemplified by organic bases such as triethylamine, N-methylmorpholine, etc. and inorganic bases such as sodium hydroxide, potassium hydroxide, potassium carbonate, and the like. Usually this reaction can be carried out at ice-cooling to room temperature. When $R^1$, $R^3$, $R^4$, $R^5$, or $R^{15}$ of compound (Ia-1) contains a functional group(s) possibly interfering this sulfonylation (e.g., hydroxy, mercapto, amino, and guanidino), it can previously be protected in accordance with a method described in "Protective Groups in Organic Synthesis" (Theodora W. Green (John Wiley & Sons)) and then deprotected at an appropriate process. When $R^2$ is not hydrogen atom, compound (Ia-1) wherein $R^2$ is hydrogen atom is further reacted with haloalkyl (e.g., methyl iodide, and ethyl iodide) or haloaralkyl (e.g., benzyl chloride, and benzyl bromide) in dimethylformamide, tetrahydrofuran, dioxane, and the like at a temperature range of ice-cooling to 80° C., preferably ice-cooling to room temperature, for 3–10 hours, preferably 10–20 hours to give the desired N—$R^2$ derivative.

(Process 2)

A hydroxylamine is reacted with compound (Ia-1) or its reactive derivatives to give hydroxamic acid derivatives (Ib-1). A hydroxylamine is usually used as its acidic salts (e.g., hydrochloride, and phosphate, sulfate: commercially available) in the presence of a base. A base to be used in this reaction is exemplified by organic bases such as triethylamine, N,N-dimethylaniline, N-methylmorpholine, etc. and inorganic bases such as sodium hydroxide, potassium hydroxide, potassium carbonate, etc. When compound (Ia-1) is used as a starting material of conversion to hydroxamic acid, this reaction is carried out in the presence of a peptide condensing agent (e.g., dicyclohexylcarbodiimide, 1-ethyl-3-(3-dimethylaminopropyl)carbodiimide, N,N'-carbonyldiimidazole, or a mixture of one of the above agents with 1-hydroxybenzotriazole, N-hydroxy sucinicimide, etc.). A solvent for this reaction may be dimethylformamide, tetrahydrofuran, dioxane, dimethylsulfoxide, acetonitrile, water, and mixed solvent thereof. This reaction is carried out at −20° C. to 40° C., preferably ice-cooling to room temperature, for 1 to 16 hours.

Acid anhydrides (especially, mixed acid anhydrides), acid halides, acid azides, and esters can be utilized in this reaction as a reactive derivative of compound (Ia-1). These reactive derivatives are produced by usual methods. For example, the acid anhydride derivatives can be produced by a reaction of compound (Ia-1) with acid halide derivatives (e.g., ethyl chlorocarbonate) in the presence of a base (e.g., triethylamine), and acid halide derivatives can be produced by a reaction of compound (Ia-1) with a halogenation agent (e.g., oxalylchloride, and thionylchloride). Ester derivatives may be inactive or active. Sulfonyl derivatives converted from a compound (XV) wherein $R^{15}$ is a carboxyl protective groups (e.g., methyl, tert-butyl, and benzyl) at process 1 can be used as inactive esters without deprotection. Active esters can be produced by a reaction of compound (Ia-1), carbodiimide reagents (e.g., dicyclohexylcarbodiimide, 1-ethyl-3-(3-dimethylaminopropyl)carbodiimide), and hydroxy derivatives corresponding to the active ester residue such as 1-hydroxybenzotriazole, N-hydroxysuccinimide, or the like. A reaction condition of conversion of the reactive derivatives of compound (Ia-1) to hydroxamic acid may be the same as that of conversion of compound (Ia-1) itself to hydroxamic acid. The reactions of processes 1 and 2 are able to continuously be carried out in one-pot reaction.

(Process 3)

A protected hydroxylamine to be used in this reaction includes O-benzylhydroxylamine, O-(p-methoxybenzyl) hydroxylamine, O-(tert-butyl)hydroxylamine, or the like. This reaction condition may be in the same manner as that of process 2.

(Process 4)

This process for deprotection is carried out by catalytic reduction, treatment with conc. hydrochloric acid, or treatment with trifluoroacetic acid to give the desired compound (Ib-1). The compounds of this invention (Ia-1) and (Ib-1) can be isolated and purified by usual separation methods and purification methods (e.g., chromatography, crystallization, etc.).

(Method B)

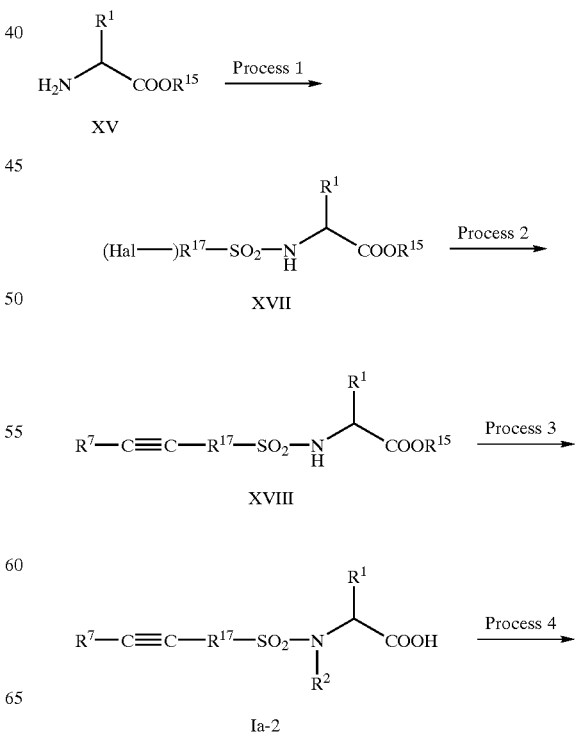

-continued

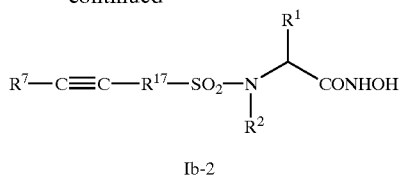

Ib-2 wherein $R^1$, $R^2$, $R^7$, $R^{15}$, and Hal are as defined above, $R^{17}$ is optionally substituted aryl or optionally substituted heteroaryl.

Conversion of compound (XV) to compound (XVII) is performed by sulfonation of an amino group of compound (XV) (process 1) in the same manner as that described in process 1 of method A. Conversion of compound (XVII) to compound (XVIII) is performed by Heck reaction (K. Sonogashira, Y. Tohda, and N. Hagihara, Tetrahedron Lett., 4467(1975) etc.) wherein halogen of $R^{17}$ is utilized to insert a triple bond (process 2). Conversion of compound (XVIII) to compound (Ia-2) is N-alkylation, deprotection of a carboxyl protective group, etc. (process 3), which can be carried out in the same manner as that described in process 1 of method A. Conversion of compound (Ia-2) to compound (Ib-2) is that of carboxylic acid derivatives to hydroxamic acid derivatives (process 4), which can be carried out in the same manner as those described in processes 2 to 4 of method A. Each process will hereinafter be described in more detail.

(Process 1)

This process may be carried out in the same manner as that described in process 1 of method A.

(Process 2)

Compound (XVII) is reacted with optionally substituted aryl or optionally substituted heteroaryl having an ethynyl group such as ethynylbenzene in a solvent such as dimethylformamide, toluene, xylene, benzene, tetrahydrofuran etc. in the presence of a palladium catalyst (e.g., Pd(Ph$_3$P)$_2$Cl$_2$), a divalent copper reagent (e.g., CuI), and an organic base (e.g., triethylamine, and diisopropylethylamine) to give a desired compound (XVIII) (Heck reaction). This reaction is carried out at room temperature to 100° C., preferably room temperature to 80° C. This reaction is completed for 3 to 30 hours, preferably 10 to 20 hours. When optionally substituted aryl or optionally substituted heteroaryl has a substituent(s) interfering this reaction, the substituent(s) can previously be protected in accordance with a method of "Protective Groups in Organic Synthesis", (Theodora W. Green (John Wiley & Sons)), and then deprotected at an appropriate step.

(Process 3)

This process may be carried out in the same manner as that described in process 1 of method A.

(Process 4)

This process may be carried out in the same manner as those described in processes 2 to 4 of method A.

(Method C)

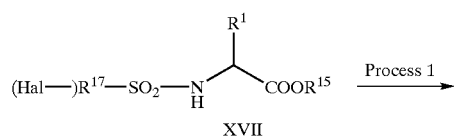

XVII

-continued

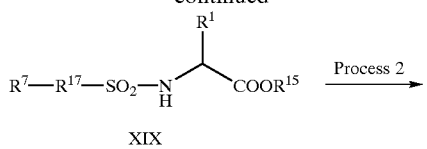

XIX

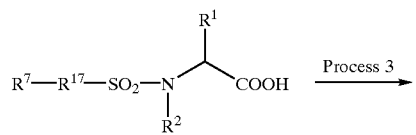

Ia-3

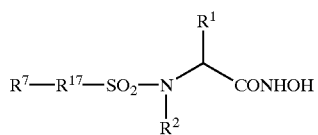

Ib-3 wherein $R^1$, $R^2$, $R^7$, $R^{15}$, $R^{17}$, and Hal are as defined above.

Conversion of compound (XVII) to compound (XIX) is performed by Suzuki reaction (M. J. Sharp and V. Shieckus, Tetrahedron Lett., 26, 5997 (1985) etc.) wherein halogen of $R^{17}$ is utilized to introduce aryl or heteroaryl (process 1). Conversion of compound (XIX) to compound (Ia-3) is N-alkylation, deprotection of a carboxyl protective group, etc. (process 2) and this process can be carried out in the same manner as that described in process 1 of method A. Conversion of compound (Ia-3) to compound (Ib-3) is that of carboxylic acid derivatives to hydroxamic acid derivatives (process 3), and this process can be carried out in the same manner as those described in processes 2 to 4 of method A. Each process will hereinafter be described in more detail.

(Process 1)

Compound (XVII) is reacted with optionally substituted aryl or optionally substituted heteroaryl having a B(OH)$_2$ (otherwise B(Et)$_2$) group such as phenylboronic acid in a solvent such as dimethylformamide, toluene, xylene, benzene, tetrahydrofuran etc. in the presence of a palladium catalyst (e.g., Pd(Ph$_3$P)$_4$) and a base (e.g., potassium carbonate, calcium carbonate, triethylamine, sodium methoxide etc.) to give the desired compound (XIX) (Suzuki reaction). This reaction is carried out at room temperature to 100° C., preferably room temperature to 80° C. This reaction is completed for 5 to 50 hours, preferably 15 to 30 hours. When optionally substituted aryl or optionally substituted heteroaryl has a substituent(s) interfering this reaction, the substituent(s) can previously be protected in accordance with a method of "Protective Groups in Organic Synthesis," (Theodora W. Green (John Wiley & Sons)) and then deprotected at an appropriate step.

(Process 2)

This process may be carried out in the same manner as that described in process 1 of method A.

(Process 3)

This process may be carried out in the same manner as those described in processes 2 to 4 of method A.

(Method D)

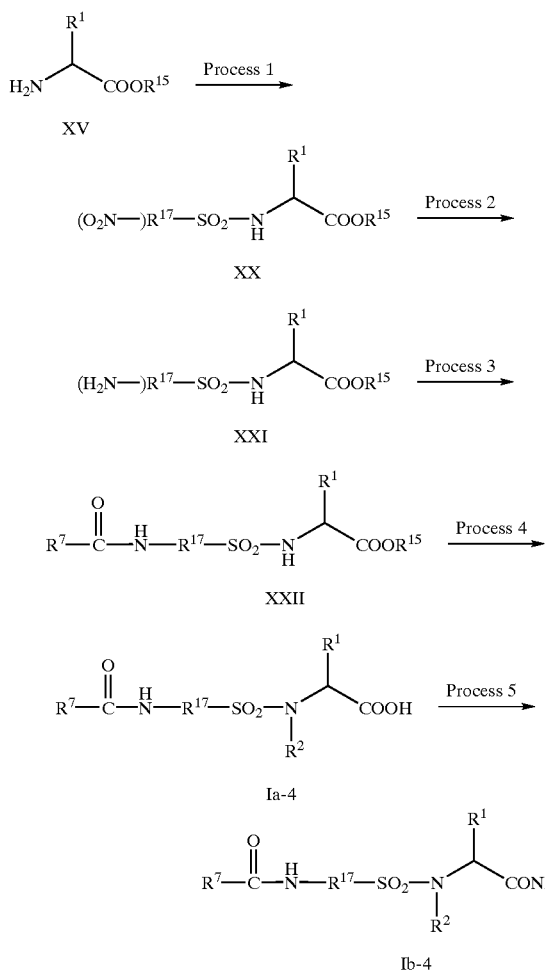

wherein $R^1$, $R^2$, $R^7$, $R^{15}$, $R^{17}$, and Hal are as defined above.

Conversion of compound (XV) to compound (XX) is sulfonation of an amino group of the compound (XV) (process 1) and this process may be carried out in the same manner as that described in process 1 of method A. Conversion of compound (XX) to compound (XXI) is reduction of a nitro group of $R^{17}$ to an amino group (process 2) and this process can be carried out by catalytic reduction or other reduction using hydrochloric chloride.Fe, hydrochloric chloride.Sn, etc. Conversion of compound (XXI) to compound (XXII) is performed by usual amide bond formation reaction wherein an amino group of $R^{17}$ is utilized (process 3). Conversion of compound (XXII) to compound (Ia-4) is N-alkylation, deprotection of a carboxyl protective group, etc. (process 4) of compound (XXII) and this process can be carried out in the same manner as that described in process 1 of method A. Conversion of compound (Ia-4) to compound (Ib-4) is that of carboxylic acid derivatives to hydroxamic acid derivatives (process 5) and this process can be carried out in the same manner as those described in processes 2 to 4 of method A. Each process will hereinafter be described in more detail.

(Process 1)

This process may be carried out in the same manner as that described in process 1 of method A.

(Process 2)

Compound (XX) is treated with hydrogen in a solvent such as methanol, ethanol, ethyl acetate, acetic acid, etc. in the presence of a catalyst (e.g., Pd—C, $PtO_2$, Raney Ni etc.), under a no-pressure or pressured condition to give the desired compound (XXI). This reaction is carried out at a temperature under ice-cooling to 80° C., preferably room temperature to 50° C., and is completed for 1 to 10 hours, preferably 2 to 5 hours.

(Process 3)

Compound (XXI) is reacted with optionally substituted aryl or optionally substituted heteroaryl having an acid halide (otherwise an active ester) group such as benzoyl chloride in a solvent such as dimethylformamide, tetrahydrofuran, dioxane, dimethylsulfoxide, acetonitrile, xylene, toluene, benzene, dichloromethane, etc. in the presence of a base (e.g., triethylamine, N-methylmorpholine, potassium carbonate etc.) to give the desired compound (XXII). This reaction is carried out at a temperature under ice-cooling to 100° C., preferably room temperature to 60° C., and is completed for 3 to 30 hours, preferably 10 to 25 hours.

(Process 4)

This process may be carried out in the same manner as that described in process 1 of method A.

(Process 5)

This process may be carried out in the same manner as those described in processes 2 to 4 of method A.

(Method E)

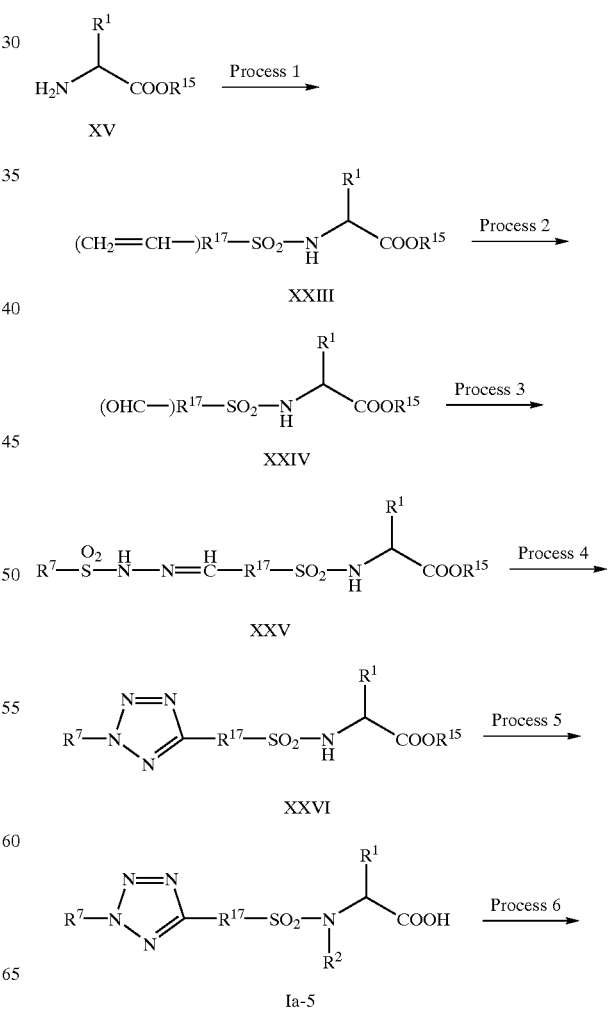

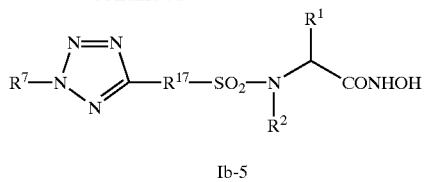

Ib-5 wherein $R^1$, $R^2$, $R^7$, $R^{15}$, $R^{17}$, and Hal are as defined above.

Conversion of compound (XV) to compound (XXIII) is performed by sulfonating an amino group of the compound (XV) (process 1) in the same manner as that described in process 1 of method A. Conversion of compound (XXIII) to compound (XXIV) is done by the reduction wherein an ethenyl group of $R^{17}$ is converted into an aldehyde group (process 2). Conversion of compound (XXIV) to compound (XXVI) is performed by a tetrazole ring formation reaction (processes 3 and 4). Conversion of compound (XXVI) to compound (Ia-5) is N-alkylation, deprotection of a carboxyl protective group, etc. of compound (XXVI) (process 5), and this process can be carried out in the same manner as that described in process 1 of method A. Conversion of compound (Ia-5) to compound (Ib-5) is that of carboxylic acid derivatives to hydroxamic acid derivatives (process 6), which can be carried out in the same manner as those described in processes 2 to 4 of method A. Each process will hereinafter be described in more detail.

(Process 1)

This process may be carried out in the same manner as that described in process 1 of method A.

(Process 2)

A compound (XXIII) is treated with ozone in a solvent such as dichloromethane, ethyl acetate, methanol, etc. to form an ozonide, and then a reagent such as zinc-acetic acid, triethylphosphate, dimethylsulfide, etc. is added to this reaction mixture for reduction to give the desired aldehyde derivatives (XXIV) The reduction can also be carried out by catalytic hydrogenation. This reaction is carried out at $-100°$ C. to room temperature, preferably $-78°$ C. to a temperature under ice-cooling, and is completed for 0.5 to 10 hours, preferably 1 to 3 hours.

(Process 3)

A compound (XXIV) is reacted with benzensulfonylhydrazide in a solvent such as tetrahydrofuran, ether, etc. mixed with a solvent such as methanol, ethanol, etc. to give the desired compound (XXV). This reaction is carried out at a temperature under ice-cooling to 80° C., preferably room temperature to 50° C., and is completed for 3 to 30 hours, preferably 10 to 20 hours.

(Process 4)

Optionally substituted aryl or optionally substituted heteroaryl having amino group such as aniline is dissolved in a mixed solvent such as alcohol (e.g., ethanol) and water. To this mixture conc. hydrochloric acid and a diazotizing agent such as a sodium nitrite aqueous solution are added at $-20°$ C. to 10° C., preferably 0° C. to 5° C., to give a diazonium salt. The reaction time is 5 min to 1 hr, preferably 10 to 30 min. This reaction mixture is added to a pyridine solution of compound (XXV) and allowed react for 1 to 10 hr, preferably 2 to 5 hr, at $-30°$ C. to 50° C., preferably $-15°$ C. to room temperature to give the desired compound (XXVI). When optionally substituted aryl or optionally substituted heteroaryl has a substituent(s) interfering this reaction, the substituent(s) can previously be protected in accordance with a method of "Protective Groups in Organic Synthesis" (Theodora W. Green (John Wiley & Sons)), and then deprotected at an appropriate step.

(Process 5)

This process may be carried out in the same manner as that described in process 1 of method A.

(Process 6)

This process may be carried out in the same manner as those described in processes 2 to 4 of method A.

(Method F)

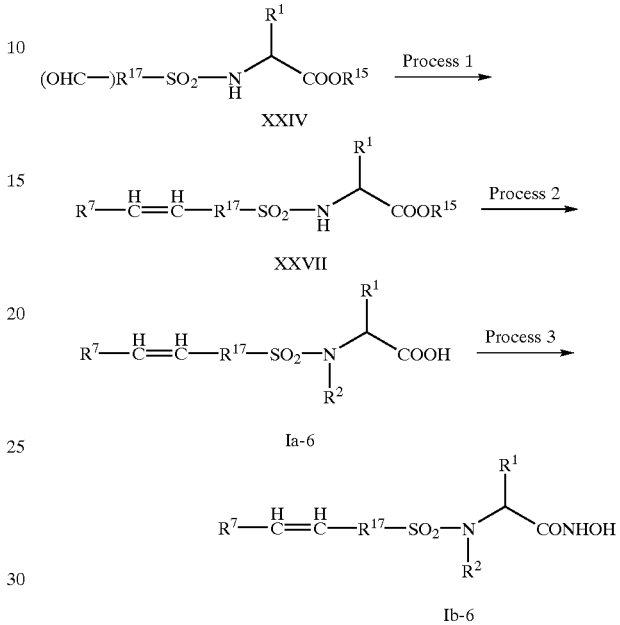

wherein $R^1$, $R^2$, $R^7$, $R^{15}$, $R^{17}$, and Hal are as defined above.

Conversion of compound (XXIV) to compound (XXVII) is performed by Wittig reaction (G. Wittig et al., Chem. Berr. 87, 1318 (1954)) wherein an aldehyde group of $R^{17}$ is utilized to introduce aryl or heteroaryl through a double bond (process 1). Conversion of compound (XXVII) to compound (Ia-6) is N-alkylation, deprotection, etc. of compound (XXVII) (process 2), and this process can be carried out the same similar as described in process 1 of method A. Conversion of compound (Ia-6) to compound (Ib-6) is that of carboxylic acid derivatives to hydroxamic acid derivatives (process 3), and this process can be carried out in the same manner as those described in processes 2 to 4 of method A. Each process will hereinafter be described in more detail.

(Process 1)

Compound (XXIV) is reacted with ylide derivatives of optionally substituted aryl or optionally substituted heteroaryl such as $Ph_3P=CHPh$, etc., which is produced by an usual method, in a solvent such as toluene, xylene, tetrahydrofuran, ether, dimethylformamide, etc. at $-100°$ C. to room temperature, preferably $-78°$ C. to ice-cooling for 1 to 20 hours, preferably 1 to 5 hours, to give the desired compound (XXVII). When optionally substituted aryl or optionally substituted heteroaryl has a substituent(s) interfering this reaction, the substituent(s) can previously be protected in accordance with a method of "Protective Groups in Organic Synthesis" (Theodora W. Green (John Wiley & Sons)), and deprotected at an appropriate step.

(Process 2)

This process may be carried out in the same manner as that described in process 1 of method A.

(Process 3)

This process may be carried out in the same manner as those described in processes 2 to 4 of method A.

The term "compound of the present invention," herein used includes pharmaceutically acceptable salt or hydrate of the compound. The salt is exemplified by a salt with alkali metals (e.g., lithium, sodium, and potassium), alkaline earth metals (e.g., magnesium and calcium), ammonium, organic bases, amino acids, mineral acids (e.g., hydrochloric acid, hydrobromic acid, phosphoric acid, and sulfuric acid), or organic acids (e.g., acetic acid, citric acid, mallein acid, fumaric acid, benzenesulfonic acid, and p-toluenesulfonic acid). These salts can be formed by the usual method.

The compound of the present invention is not restricted to any particular isomers but includes all possible isomers and racemic modifications.

The compound of the present invention has an excellent activity for inhibiting metalloproteinase, especially activity for inhibiting MMP, and inhibits matrix dissolution, as described in the following test example. Therefore, the compound of the present invention is useful to treat or prevent diseases which are caused by MMP and relative enzymes such as TNF-α converting enzyme, etc.

Definitely, the compounds of the present invention are useful in the prevention or treatment of diseases such as osteoarthritis, rheumatoid arthritis, corneal ulceration, periodontal disease, metastasis and invasion of tumor, advanced virus infection (e.g., HIV), arteriosclerosis obliterans, arteriosclerotic aneurysm, atherosclerosis, restenosis, sepsis, septic shock, coronary thrombosis, aberrant angiogenesis, scleritis, multiple sclerosis, open angle glaucoma, retinopathies, proliferative retinopathy, neovascular glaucoma, pterygium, keratitis, epidermolysis bullosa, psoriasis, diabetes, nephritis, neurodegengerative disease, gingivitis, tumor growth, tumor angiogenesis, ocular tumor, angiofibroma, hemangioma, fever, hemorrhage, coagulation, cachexia, anorexia, acute infection, shock, autoimmune disease, malaria, Crohn disease, meningitis, and gastric ulcer.

When the compound of the present invention is administered to a person for treatment or prevention of the above diseases, they can be administered by oral administration such as powder, granules, tablets, capsules, pilulae, and liquid medicine, or by parenteral administration such as injections, suppository, percutaneous formulations, insufflation, or the like. An effective dose of the compound of the invention is formulated by being mixed with medicinal admixture such as excipient, penetrant, disintegrators, lubricant, and the like if necessary. When parenteral injection is prepared, the compound of the invention and an appropriate carrier are sterilized to prepare it.

An appropriate dosage varies with the conditions of the patients, an administration route, their age, their body weight and the like and should be determined by a physician in the end. In the case of oral administration, a daily dosage can generally be between 0.1–100 mg/kg/day, preferably 1–20 mg/kg/day. In the case of parenteral administration, the daily dosage can generally be between 0.01–10 mg/kg/day, preferably 0.1–1 mg/kg/day. The daily dosage can be administrated in one to several divisions.

The following examples are provided to further illustrate the present invention and are not to be constructed as limiting the scope thereof.

Abbreviations described below are used in the following examples.

p-TsOH: p-toluenesulfonic acid
DMSO: dimethylsulfoxide
Me: methyl
$^t$Bu: tert-butyl

EXAMPLE 1

(Method A)

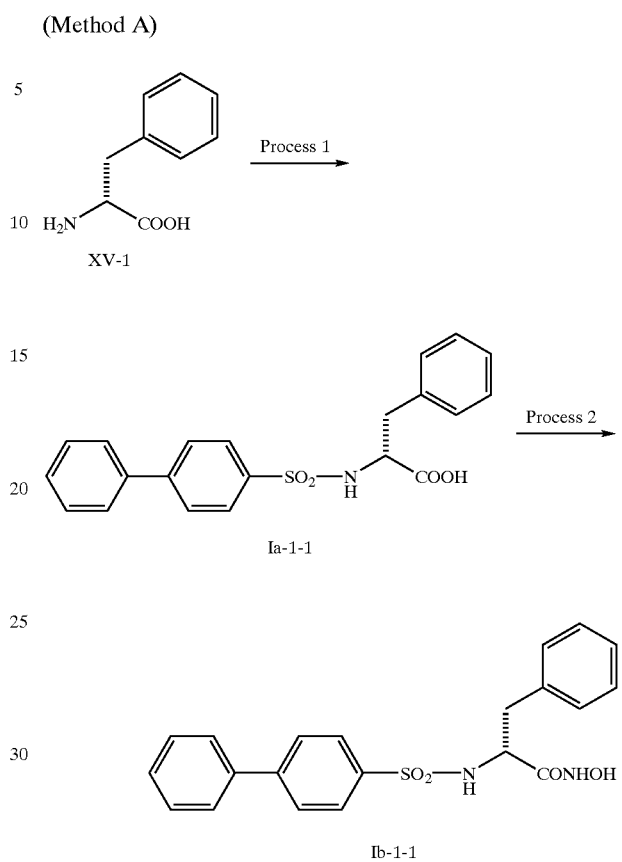

To a suspension of (R)-(+)-phenylalanine (compound XV-1, 1.65 g (10 mmol)) in 50 ml of dimethylformamide and 35 ml of water was stirred and treated with 2.78 ml (20 mmol) of triethylamine under ice-cooling. Then, 2.52 g(10 mmol) of 4-biphenylsulfonyl chloride in 10 ml of dimethylformamide was added dropwise to the mixture over 5 min. After the reaction mixture was stirred for 2 h at the same temperature, 1.35 g (10 mmol) of 1-hydroxybenzotriazole hydrate, 2.1 g (11 mmol) of 1-ethyl-3-(3-dimethylaminopropyl)carbodiimide hydrochloride, 3.47 g (50 mmol) of hydroxylamine hydrochloride, and 7 ml (50 mmol) of triethylamine were added to the mixture. After being stirred for 16 h at room temperature, the reaction mixture was poured into water and extracted with ethyl acetate. The organic layer was washed with 2N HCl, 5% NaHCO$_3$, and water, and concentrated in vacuo. The residue was subjected to silica gel column chromatography and the fractions eluting with CHCl$_3$/MeOH=40/1 to 20/1 were collected to yield 1.70 g of compound (Ib-1-1) as a foam. Yield 43%. mp. 169–170° C.

Elemental analysis (%) $C_{21}H_{20}N_2O_4S$

Calcd.: C, 63.62; H, 5.08; N, 7.07; S, 8.09. Found: C,63.61; H, 5.12; N, 6.98; S, 8.06.

IR ν max (cm$^{-1}$) (Nujol): 3365, 3295, 3266, 1674, 1320, 1159.

NMR (δ ppm) d$_6$-DMSO: 2.61 (dd, J=8.6, 13.4 Hz, 1H), 2.80 (dd, J=6.0, 13.6 Hz, 1H), 3.80 (m, 1H).

[α]$_D$: +18.5±1.2 (c=0.503%, 25° C., DMSO)

EXAMPLE 1'

Another synthetic method of compound (Ib-1-1)

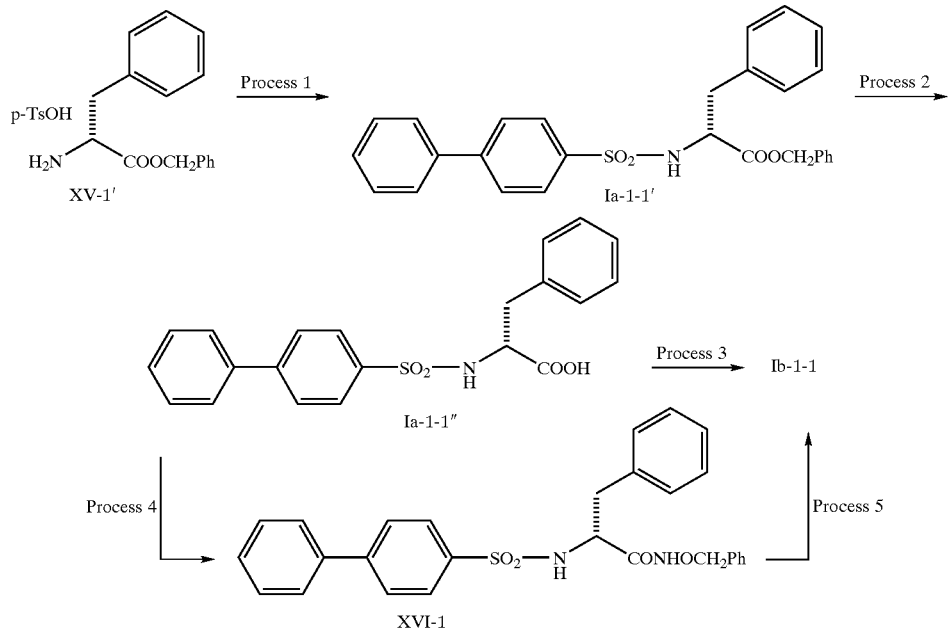

Process 1

To a solution of (R)-phenylalanine benzyl ester tosylate (compound XV-1', 2.5 g (5.85 mmol)) in 60 ml of dichloromethane was added triethylamine (1.8 ml, 12.87 mmol) and 4-biphenylsulfonyl chloride(1.63 g, 6.44 mmol) under ice-cooling. After being stirred for 2 h at room temperature, the reaction mixture was washed with 2N HCl, 5% $NaHCO_3$ and water, and concentrated in vacuo. The residue was subjected to silica gel column chromatography and the fractions eluting with $CHCl_3$/MeOH=40/1 to 20/1 were collected and crystallized from dichloromethane/hexane to give 2.32 g of compound (Ia-1-1'). Yield 84.1%. mp. 130–131° C.

Elemental analysis (%) $C_{28}H_{25}NO_4S$

Calcd.: C, 71.32; H, 5.34; N, 2.97; S, 6.80. Found: C, 71.05; H, 5.41; N, 3.00; S, 6.81.

IR ν max ($cm^{-1}$) (Nujol): 3352, 1732, 1341, 1190, 1163.

NMR (δ ppm) ($CDCl_3$): 3.06 (d, J=5.8 Hz, 2H), 4.30 (dt, J=6.0, 9.0 Hz, 1H), 4.89 (s, 2H), 5.12 (d, J=9.0 Hz, 1H), 6.98–7.81 (m, 14H).

$[α]_D$: −16.4±1.1(c=0.506%, 25° C., MeOH)

Process 2

A solution of compound (Ia-1-1') (2.28 g) which was obtained process 1 in 50 ml of mixed solvents of methanol/ethyl acetate=1/1, was hydrogenated using 10% Pd/C (200 mg) for 25 min. The reaction mixture was filtered off, and the filtrate was concentrated in vacuo. The residue was recrystallized from dichloromethane/hexane to give 1.83 g of compound (Ia-1-1"). Yield 99.1%. mp. 146–147° C.

Elemental analysis (%) $C_{21}H_{19}NO_4S$

Calcd.: C, 66.12; H, 5.02; N, 3.67; S, 8.41. Found: C,65.97; H, 5.06; N, 3.61; S, 8.48.

IR ν max ($cm^{-1}$) (Nujol): 3408, 3305, 1751, 1325, 1161, 1134.

NMR (δ ppm) ($CDCl_3$): 2.97 (dd, J=7.0, 13.8 Hz, 1H), 3.14 (dd, J=5.2, 14.0 Hz,1H), 4.13 (m, 1H), 7.03–7.78 (m, 14H).

$[α]_D$: −4.0±0.4(c=1.000%, 25° C., MeOH)

Process 3

To a solution of compound (Ia-1-1", 1.0 g (2.62 mmol)) which was obtained process 2 in dichloromethane (20 ml) was added 0.33 ml (3.93 mmol) of oxalyl chloride and one drop of dimethylformamide. After being stirred for stirred for 1 h at room temperature, the reaction mixture was concentrated in vacuo. The residue was dissolved in 10 ml of tetrahydrofuran. A solution of hydroxylamine hydrochloride (911 mg (13.1 mmol)) and $NaHCO_3$ 1.54 g (18.34 mmol)) in 10 ml of tetrahydrofuran and 10 ml of water was stirred for 5 min under ice-cooling. To the mixture was added the above solution of acid chloride in tetrahydrofuran and the resulting mixture was stirred for 30 min. The reaction mixture was poured into water, and extracted with ethyl acetate. The organic layer was washed with 5% $NaHCO_3$, and water, and concentrated in vacuo to give compound (Ia-1) (969 mg). Yield 93.3%.

Process 4

To a solution of compound (Ia-1-1", 2.0 g, 5.24 mmol) which was obtained process 2 in dimethylformamide (20 ml) was added 1-hydroxybenzotriazole hydrate (0.7 g, 5.24 mmol), N-methylmorpholine (2.9 ml, 26.2 mmol), 1-ethyl-3-(3-diisopropylamino) carbodiimide hydrochloride (8 mmol), and O-benzylhydroxylamine hydrochloride (1.67 g, 10.48 mmol), and the resulting mixture was stirred for 6 h at room temperature. The reaction mixture was poured into water and extracted with ethyl acetate. The organic layer was washed with 2N HCl, 5% $NaHCO_3$, and water, and concentrated in vacuo. The residue was subjected to silica gel column chromatography and the fractions eluting with $CH_2Cl_2$/hexane=1/1 were collected and recrystallized from dichloromethane/hexane to give 2.04 g of compound (XVI-1). Yield 80%. mp. 171–173° C.

Elemental analysis (%) $C_{28}H_{26}N_2O_4S$

Calcd.: C, 69.12; H, 5.39; N, 5.76; S, 6.59. Found: C, 68.85; H, 5.46; N, 5.76; S, 6.78.

IR ν max ($cm^{-1}$) (Nujol): 3248, 1661, 1594, 1333, 1163.

NMR (δ ppm) (CDCl$_3$): 2.85–3.60 (m, 2H), 3.86 (m, 1H), 4.77 (ABq-Apart, J=11.4 Hz, 1H), 4.82 (ABq-Bpart, J=11.4 Hz, 1H), 5.00 (m, 1H), 6.95–7.70 (m, 19H).

[α]$_D$: −40.2±1.6 (c=0.505%, 25° C., DMSO)

Process 5

A solution of compound (XVI-1) (1.97 g) which was obtained process 4 in a 60 ml of mixed solvents of methanol/ethyl acetate=1/1 was hydrogenated using 10% Pd—C (200 mg) for 3.5 h. The reaction mixture was filtered off, and the filtrate was concentrated in vacuo. The residue was recrystallized from dichloromethane/hexane to give 1.35 g of compound (Ib-1-1). Yield 84.4%.

EXAMPLE 2–91

The compounds which were shown in Tables 1 to 22 were synthesized in a manner similar to those described in Example 1'

TABLE 1

(Ib)

R$^{18}$SO$_2$NH—*C(R$^1$)—CONHOH

| Example No. | R$^1$ | R$^{18}$ | * | mp (decomp.) (° C.) | IR (ν cm$^{-1}$) (KBr) | $^1$H-NMR (δ ppm) d$_6$-DMSO |
|---|---|---|---|---|---|---|
| 2 | thiazol-4-yl-CH$_2$— | biphenyl-4-yl | RS | 173> | 3258, 1650, 1377, 1348, 1163 (Nujol) | 2.87(dd, J=5.6, 14.2Hz, 1H), 2.98 (dd, J=8.4, 14.2Hz, 1H), 4.02(dd, J=2.2, 8.6Hz, 1H), 7.24(d, J=2.0Hz, 1H), 8.83(d, J=2.2Hz, 1H) |
| 3 | indol-3-yl-CH$_2$— | biphenyl-4-yl | R | 203–206 | 3403, 3386, 3265, 1673, 1320, 1162 (Nujol) | 2.72(dd, J=7.2, 13.8Hz, 1H), 2.97 (dd, 7.0, 14.8Hz, 1H), 3.81(m, 1H), |
| 4 | 5-methoxy-indol-3-yl-CH$_2$— | biphenyl-4-yl | RS | — | — | — |
| 5 | naphthalen-1-yl-CH$_2$— | biphenyl-4-yl | RS | 124–126 | 3277, 1669, 1397, 1322, 1159, | 3.12(dd, J=10.3, 14.3Hz, 1H), 3.89 (dd, J=3.3, 13.5Hz, 1H), 4.20(m, 1H), 5.90(brs, 1H) |
| 6 | biphenyl-4-yl-CH$_2$— | biphenyl-4-yl | R | 139–141 | 3262, 1663, 1322, 1157, | 2.67(dd, J=9.2, 13.1Hz, 1H), 2.84 (dd, J=5.3, 13.5Hz, 1H), 3.82(m, 1H) |
| 7 | CF$_3$CH$_2$— | biphenyl-4-yl | R | 167–169 | 3265, 1676 1642, 1337, 1161 (Nujol) | 2.2–2.7(m, 2H), 3.99(t, J=7.0Hz, 1H) |
| 8 | phenyl-CH$_2$CH$_2$— | biphenyl-4-yl | RS | 172–173 | 3403, 3261, 1669, 1321, 1160 | 1.68(m, 2H), 2.37(m, 2H), 3.64(t, J=6.9Hz, 1H) |
| 9 | phenyl-CH$_2$— | 4-Br-phenyl | R | 144–146 | 3700–2200br, 3264, 1635, 1342, 1164 | 2.61(dd, J=9.4, 13.8Hz, 1H), 2.78 (dd, J=6.0, 13.8Hz, 1H), 3.78(m, 1H), 7.43(d, J=8.2Hz, 2H), 7.60 (d, J=8.2Hz, 2H), |

TABLE 2

$$R^{18}SO_2NH-\overset{R^1}{\underset{*}{CH}}-CONHOH \quad (Ib)$$

| Example No. | R¹ | R¹⁸ | * | mp (decomp.) (° C.) | IR (ν cm⁻¹) (KBr) | ¹H-NMR (δ ppm) d₆-DMSO |
|---|---|---|---|---|---|---|
| 10 | phenyl-CH₂— | 4-(F₃C)-phenyl- | R | 116–118 | 3600–2400br, 3257, 1743, 1721 1323, 1132, | 2.60–2.82(m, 2H), 3.84(m, 1H), 7.00–7.18(m, 5H), 7.62–7.80(m, 4H). |
| 11 | phenyl-CH₂— | 5-(dimethylamino)naphthalen-1-yl- | R | 91–92 | 3700–2100br, 3176, 1664, 1320, 1143, | 2.70–2.93(m, 2H), 2.82(s, 6H), 3.75(m, 1H), |
| 12 | (CH₃)₂CH— | 4-(H₃CO)-phenyl- | R | 178–179 | 3268, 1632, 1598, 1336, 1162 | 0.71(d, J=6.8z, 3H), 0.74(d, J=5.4Hz, 3H), 1.73(m, 1H), 1.73(m, 1H), 3.22(m, 1H), 3.82(s, 3H), 7.05(d, J=9.0Hz, 2H), 7.69(d, J=9.0Hz, 2H) |
| 13 | 4-(O₂N)-phenyl-CH₂— | biphenyl-4-yl- | RS | 184–185 | 3257, 1662, 1516, 1344, 1322, 1160, | 2.80(dd, J=10.0, 13.8Hz, 1H), 2.92(dd, J=5.0, 12.8Hz, 1H), 3.90(dd, J=5.4, 9.6Hz, 1H), |
| 14 | 4-F-phenyl-CH₂— | biphenyl-4-yl- | RS | 128–130 | 3258, 1669, 1509, 1322, 1157 | 2.62(dd, J=9.9, 13.5Hz, 1H), 2.78(dd, J=5.8, 13.0Hz, 1H), 3.77(t, J=6.2Hz, 1H), |
| 15 | cyclohexyl-CH₂— | biphenyl-4-yl- | R | 165–166 | 3278, 2920, 1632, 1337, 1161 | 0.50–1.62(m, 13H), 3.56 (t, J=7.4Hz, 1H) |
| 16 | (1-methyl-1H-indol-3-yl)-CH₂— | biphenyl-4-yl- | RS | 172–173 | 3272, 1631, 1332, 1161 | 2.71(dd, J=7.9, 14.2Hz, 1H), 2.94(dd, J=6.9, 14.2Hz, 1H), 3.57(s, 3H), 3.83(dd, J=7.0, 7.4Hz, 1H) |
| 17 | (5-methyl-1H-indol-3-yl)-CH₂— | biphenyl-4-yl- | RS | 144–146 | 3404, 1670, 1320, 1159 | 2.25(s, 3H), 2.67(dd, J=7.5, 14.2Hz, 1H), 2.95(dd, J=7.7, 14.6Hz, 1H), 3.81(dd, J=6.2, 14.2Hz, 1H) |

TABLE 3

(Ib)

$$R^{18}SO_2NH-\overset{R^1}{\underset{*}{C}}H-CONHOH$$

| Example No. | R¹ | R¹⁸ | * | mp (decomp.) (° C.) | IR(ν cm⁻¹) (KBr) | ¹H-NMR(δ ppm) d₆-DMSO |
|---|---|---|---|---|---|---|
| 18 | 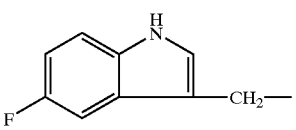 | 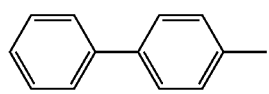 | RS | — | 3420, 1670 1592, 1321, 1159 | 2.72(dd, J=8.0, 14.0Hz, 1H), 2.90 (dd, J=6.2, 14.2Hz, 1H), 3.82(m, 1H) |
| 19 | 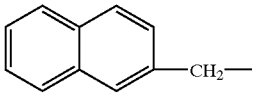 | 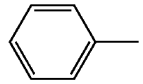 | RS | — | — | — |
| 20 | 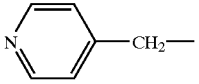 | 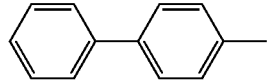 | RS | 154–158 | 3186, 1593, 1480, 1379 | 2.68(dd, J=9.8, 13.7Hz, 1H), 2.79 (dd, J=5.6, 12.8Hz, 1H), 3.85(t, J=7.0Hz, 1H), |
| 21 | 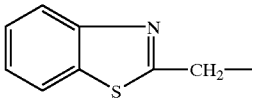 | 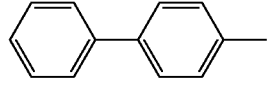 | RS | 111–115 | 3700–2400br, 3252, 1668, 1326, 1160 | 3.22–3.38(m, 2H), 4.17–4.24(m, 2H), 7.80(d, J=8.0Hz, 2H), 7.96(d, J=6.4Hz, 2H) |
| 22 | 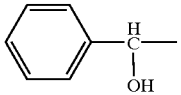 | 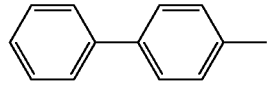 | RS | — | 3455, 3362, 1672, 1398, 1162 | 3.86(d, J=3.6Hz, 1H), 4.91 (d, J=3.6Hz, 1H) |
| 23 |  | 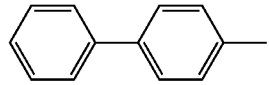 | R | 196–197 | 3404, 3315, 1669, 1594, 1316, 1162 | 4.88(d, J=9.4Hz, 1H), 8.74(d, J=9.4Hz, 1H), 8.98(s, 1H), 10.92(s, 1H) |
| 24 | 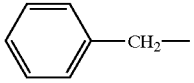 | 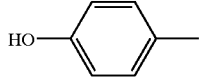 | R | 197–199 | 3700–2400(br), 3473, 1675, 1310, 1152 | 2.69(dd, J=7.6, 13.5Hz, 1H), 2.93 (dd, J=7.6, 13.5Hz, 1H), 3.77(t, J=7.6Hz, 1H), (CD₃OD) |
| 25 | 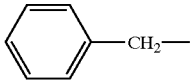 | 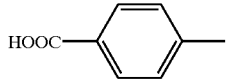 | R | 201–202 | 3700–2200(br), 3278, 1706, 1645, 1322, 1162 | 2.74(dd, J=8.3, 13.5Hz, 1H), 2.95 (dd, J=6.5, 13.5Hz, 1H), 3.87(dd, J=6.5, 8.3Hz, 1H), (CD₃OD) |

TABLE 4

(Ib)

$$R^{18}SO_2NH-\overset{R^1}{\underset{*}{C}}H-CONHOH$$

| Example No. | R¹ | R¹⁸ | * | mp (decomp.) (° C.) | IR (ν cm⁻¹) (KBr) | ¹H-NMR(δ ppm) d₆-DMSO |
|---|---|---|---|---|---|---|
| 26 | 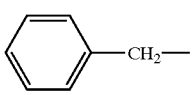 | 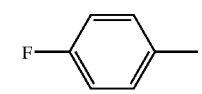 | R | 63–65 | 3700–2200(br), 3362, 1670, 1590, 1336, 1152 | 2.60(dd, J=9.0, 13.8Hz, 1H), 2.79 (dd, J=9.3, 13.8Hz, 1H), 3.76(m, 1H) |

TABLE 4-continued $$R^{18}SO_2NH-\overset{R^1}{\underset{*}{C}}H-CONHOH \quad (Ib)$$

| Example No. | R¹ | R¹⁸ | * | mp (decomp.) (° C.) | IR (ν cm⁻¹) (KBr) | ¹H-NMR(δ ppm) d₆-DMSO |
|---|---|---|---|---|---|---|
| 27 | 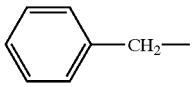 | 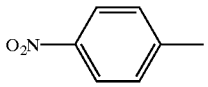 | R | 70–71 | 3700–2200br, 3372, 1674, 1531, 1348, 1310, 1161 | 2.66(dd, J=9.5, 13.6Hz, 1H), 2.79 (dd, J=5.4, 13.6Hz, 1H), 3.84(m, 1H), 7.73(A₂B₂qJ=8.9Hz, 2H), 8.20(A₂B₂q, J=8.9Hz, 2H), 8.72(d, J=9.0Hz, 1H), 8.86(s, 1H), 10.7(s, 1H) |
| 28 | HOOC—CH₂— | 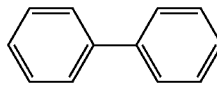 | R | — | — | — |
| 29 | HOOC—CH₂—CH₂— | 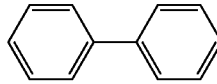 | R | — | — | — |
| 30 | HOCH₂— | 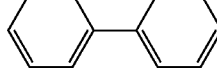 | R | 192–193 | 3700–2400(br), 3392, 1667, 1320, 1161 | 3.29(dd, J=5.7, 10.7Hz, 1H), 3.43 (dd, J=8.4, 10.7Hz, 1H), 3.62(m, 1H), 7.85(A₂B₂q, J=8.7Hz, 2H), 7.88(A₂B₂q, J=8.7Hz, 2H), 7.98 (d, J=7.8Hz, 1H), 10.61(s, 1H) |
| 31 | 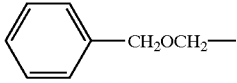 | 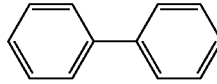 | R | 69–70 | 3700–2200(br), 1671, 1329, 1163 | 2.69(dd, J=7.6, 13.5Hz, 1H), 2.93 (dd, J=7.6, 13.5Hz, 1H), 3.77(t, J=7.6Hz, 1H), (CD₃OD) |
| 32 | 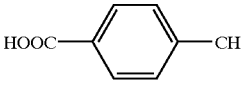 | 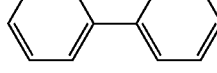 | R | — | — | — |
| 33 | 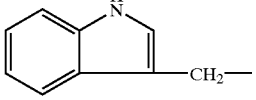 | 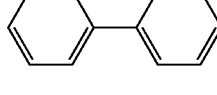 | R | 160–162 | 3401, 3260, 1673, 1316, 1165 | 2.66(dd, J=7.5, 13.4Hz, 1H), 2.96 (dd, J=7.6, 14.2Hz, 1H), 3.81(m, 1H) |

TABLE 5

$$R^{18}SO_2NH-\overset{R^1}{\underset{*}{C}}H-CONHOH \quad (Ib)$$

| Example No. | R¹ | R¹⁸ | * | mp (decomp.) (° C.) | IR (ν cm⁻¹) (KBr) | ¹H-NMR(δ ppm) d₆-DMSO |
|---|---|---|---|---|---|---|
| 34 | 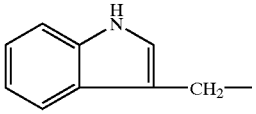 | 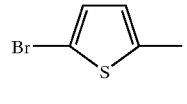 | R | — | — | — |
| 35 | 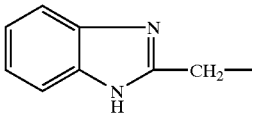 | 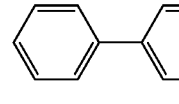 | RS | 141–145 | 3700–2400(br), 1672, 1443, 1327, 1094 | 2.84–3.21(m, 2H), 4.29(m, 1H) |

TABLE 6

$$R^{18}SO_2NH-\overset{R^1}{\underset{*}{C}}H-COOH \quad (Ia)$$

| Example No. | R¹ | R¹⁸ | * | mp (decomp.) (°C.) | IR(ν cm⁻¹) (KBr) | ¹H-NMR(δ ppm) d₆-DMSO |
|---|---|---|---|---|---|---|
| 2 | thiazol-4-yl-CH₂— | biphenyl-4-yl | RS | 159–161 | 3276, 2503br, 1897br, 1724, 1344, 1170 (Nujol) | 2.95(dd, J=9.0, 14.0Hz, 1H), 3.12 (dd, J=5.4, 14.0Hz, 1H), 4.13(m, 1H), 7.29(d, J=2.0Hz, 1H), 8.34(d, J=8.6Hz, 1H), 8.88(d, J=2.0Hz, 1H), 12.79(br, 1H) |
| 3 | (1H-indol-3-yl)-CH₂— | biphenyl-4-yl | R | 227–229 | 3386, 3305, 1747, 1363, 1323, 1161, 1135(Nujol) | 2.88(dd, J=8.0, 14.0Hz, 1H), 3.09 (dd, J=6.0, 14.0Hz, 1H), 3.91(m, 1H), 8.23(m, 1H), 10.79(s, 1H), 12.70 (br, 1H) |
| 4 | (5-methoxy-1H-indol-3-yl)-CH₂— | biphenyl-4-yl | RS | 181–189 | 2400–3700(br), 1734, 1484, 1327, 1160 | 2.75–3.06(m, 2H), 3.69(s, 3H), 3.90(m, 1H) |
| 5 | (naphth-1-yl)-CH₂— | biphenyl-4-yl | RS | 198–200 | 3446, 3065, 1594, 1397, 1303, 1154, 1094 | 3.17(dd, J=7.4, 13.8Hz, 1H), 3.57 (dd, J=5.5, 13.9Hz, 1H), 3.80(t, J=5.6Hz, 1H), 8.11(d, J=7.4Hz, 1H) |
| 6 | (biphenyl-4-yl)-CH₂— | biphenyl-4-yl | R | 213–215 | 3184, 1723, 1337, 1317, 1156 | 2.77(dd, J=9.7, 13.7Hz, 1H), 3.03 (dd, J=4.9, 13.3Hz, 1H), 3.93(m, 1H), 8.38(d, J=8.8Hz, 1H) |
| 7 | CF₃CH₂— | biphenyl-4-yl | R | 176–177 | 3276, 1706, 1344, 1260, 1165 | 2.40–2.90(m, 2H), 4.05(m, 1H), 8.51 (d, J=9.0Hz, 1H), 13.2(br, 1H) |
| 8 | phenyl-CH₂CH₂— | biphenyl-4-yl | RS | 153–156 | 3289, 1739, 1326, 1159, 1089 | 1.83(m, 2H), 2.52(m, 2H), 3.70(m, 1H), 8.32(d, J=9.0Hz, 1H) |
| 11 | phenyl-CH₂— | 5-(dimethylamino)naphth-1-yl | R | 103–105 | 2200–3700br, 3439, 3288, 1725, 1329, 1143 | 2.86(m, 1H), 2.87(s, 6H), 2.98(dd, J=5.1, 13.8Hz, 1H), 4.15(m, 1H), 5.54(m, 1H) |

TABLE 7

(Ia)

R¹⁸SO₂NH—*CH(R¹)—COOH

| Example No. | R¹ | R¹⁸ | * | mp (decomp.) (° C.) | IR(ν cm⁻¹) (KBr) | ¹H-NMR(δ ppm) d₆-DMSO |
|---|---|---|---|---|---|---|
| 13 |  4-O₂N-C₆H₄-CH₂— | 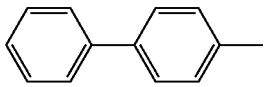 biphenyl | RS | 212–213 | 3113, 1724, 1520, 1345, 1158 | 2.86(dd, J=10.2, 13.2Hz, 1H), 3.14(dd, J=4.5, 13.7Hz, 1H), 4.02(m, 1H), 8.42(d, J=8.4Hz, 1H) |
| 14 | 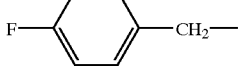 4-F-C₆H₄-CH₂— | 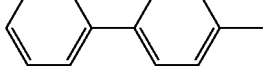 biphenyl | RS | 164–165 | 3246, 3114, 1715, 1509, 1224, 1159 | 2.71(dd, J=9.9, 13.7Hz, 1H), 2.96 (dd, J=5.3, 13.5Hz, 1H), 3.89 (m, 1H), 8.34(d, J=9.0Hz, 1H) |
| 15 | 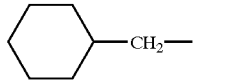 cyclohexyl-CH₂— | 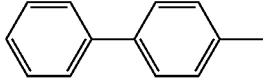 biphenyl | R | 85–87 | 2919, 1688, 1448, 1335, 1326, 1169 | 0.52–1.72(m, 13H), 3.68(m, 1H), 8.20(br.s, 1H) |
| 16 | 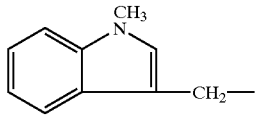 N-methylindol-3-yl-CH₂— | 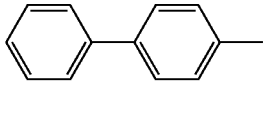 biphenyl | RS | 179–183 | 3432, 3294, 1713, 1482, 1341, 1159 | 2.80–3.12(m, 2H), 3.61(s, 3H), 3.94 (m, 1H), 8.30(d, J=8.6Hz, 1H) |
| 17 | 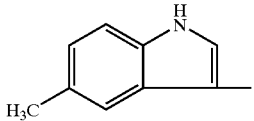 5-methylindol-3-yl-CH₂— | 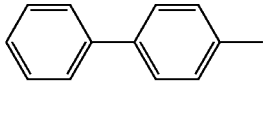 biphenyl | RS | 115–120 | 3419, 3397, 3291, 1736, 1482, 1336, 1321, 1165 | 2.28(s, 3H), 2.78–3.10(m, 2H), 3.91 (m, 1H), 8.29(d, J=8.3Hz, 1H) |
| 18 | 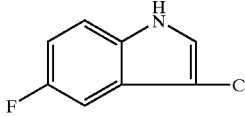 5-fluoroindol-3-yl-CH₂— | 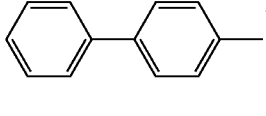 biphenyl | RS | 208–211 | 3407, 3285, 1751, 1735, 1703, 1486, 1321, 1162 | 2.80–3.10(m, 2H), 3.92 (m, 1H), 8.29(d, J=8.2Hz, 1H) |
| 20 | 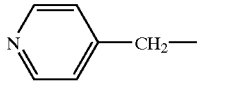 pyridin-4-yl-CH₂— | 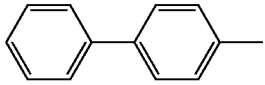 biphenyl | RS | 197–205 | 2600–3700br, 1635, 1594, 1335, 1163, 1095 | 2.60–3.0(m, 2H), 3.98(m, 1H) |
| 21 | 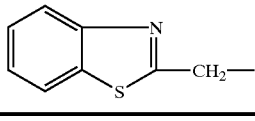 benzothiazol-2-yl-CH₂— | 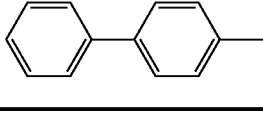 biphenyl | RS | 196–199 | 2200–3700br, 1713br, 1345, 1125 | 3.24–3.56(m, 2H), 4.34 (m, 1H) |

TABLE 8

(Ia)

R¹⁸SO₂NH—*CH(R¹)—COOH

| Example No. | R¹ | R¹⁸ | * | mp (decomp.) (° C.) | IR(ν cm⁻¹) (KBr) | ¹H-NMR(δ ppm) d₆-DMSO |
|---|---|---|---|---|---|---|
| 22 | 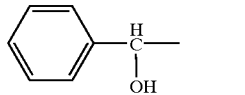 PhCH(OH)— | 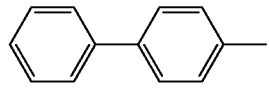 biphenyl | RS | 141–143 | 3335, 3246, 1732, 1315, 1152 | 4.10(d, J=3.2Hz, 1H), 5.13(d, J=3.2Hz, 1H) |

TABLE 8-continued (Ia)

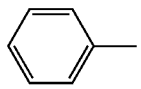

| Example No. | R¹ | R¹⁸ | * | mp (decomp.) (° C.) | IR(ν cm⁻¹) (KBr) | ¹H-NMR(δ ppm) d₆-DMSO |
|---|---|---|---|---|---|---|
| 23 | 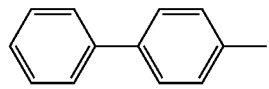 | 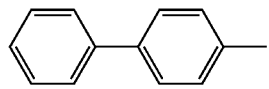 | R | 211–214 | 3316, 1734, 1325, 1159 (Nujol) | 4.94(d, J=9.4Hz, 1H), 8.80(d, J= 9.4Hz, 1H), 13.0(br.s, 1H) |
| 28 | HOOC—CH₂— | 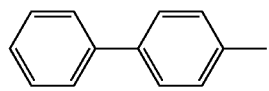 | R | 171–173 | 3353, 1752, 1326, 1155, 1096 | 2.45(dd, J=6.2, 16.4Hz, 1H) 2.63 (dd, J=6.6, 16.4Hz, 1H), |
| 29 | HOOC—CH₂—CH₂— | 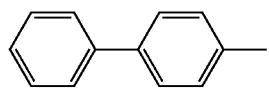 | R | 185–187 | 3270, 1709, 1336, 1159, 1093 | 1.68(dd, J=7.9, 14.1Hz, 1H), 18.7 (dd, J=6.0, 13.4Hz, 1H), 2.22(t, J= 7.2Hz, 2H), 3.80(m, 1H), |
| 30 | HOCH₂— | 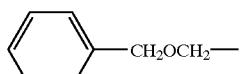 | R | 277–279 | 2200–3700br, 3430, 3292, 1728, 1324, 1162 | 3.51(dd, J=6.0, 12.9Hz, 1H), 3.55 (dd, J=5.4, 12.9Hz, 1H), 3.80(m, 1H), 8.06(d, J=8.7Hz, 1H) |
| 31 | 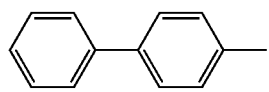 | 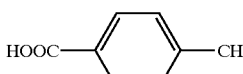 | R | 89–91 | 2200–3700br, 3432, 3289, 1733, 1330, 1165 | 3.54(dd, J=4.8, 9.9Hz, 1H), 3.60 (dd, J=5.7, 9.9Hz, 1H), 4.0(m, 1H), 4.39(s, 2H), 8.34(d, J=81Hz, 1H) |
| 32 | 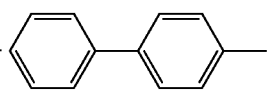 | 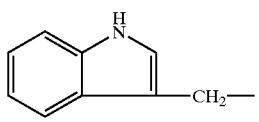 | R | >270 | 3319, 3052, 1701, 1317, 1284, 1162 | 2.81(dd, J=9.7, 13.7Hz, 1H), 3.05 (dd, J=4.8, 13.4Hz, 1H), 3.96(m, 1H), 8.40(d, J=9.0Hz, 1H), 12.88 (br.s, 1H) |

TABLE 9

(Ia)

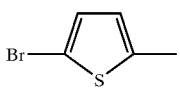

| Example No. | R¹ | R¹⁸ | * | mp (decomp.) (° C.) | IR(ν cm⁻¹) (KBr) | ¹H-NMR(δ ppm) d₆-DMSO |
|---|---|---|---|---|---|---|
| 34 | 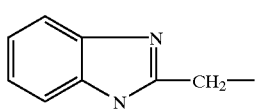 | 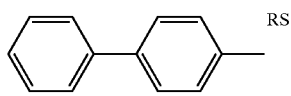 | R | 243–246 | 3420, 1588, 1402, 1324, 1151 | 3.06(dd, J=5.4, 14.4Hz, 1H), 3.14 (dd, J=5.1, 14.4Hz, 1H), 3.65(t, J= 5.4Hz, 1H), 6.92(m, 1H), 10.72(s, 1H) |
| 35 | | | RS | 151–156 | 2200–3700br, 1734, 1334, 1161 | 3.17–3.50(m, 2H), 4.51(m, 1H) |

TABLE 10

(Ia)

$$R^{18}SO_2NH-\overset{R^1}{\underset{*}{C}H}-COOH$$

| Example No. | R$^1$ | R$^{18}$ | * | mp (decomp.) (° C.) | IR(v cm$^{-1}$) (KBr) | Elemental analysis |
|---|---|---|---|---|---|---|
| 36 | indole-3-CH$_2$- with N-SO$_2$CH$_3$ | biphenyl | RS | >145 | 1726, 1354, 1326, 1161 | — |
| 37 | indole-3-CH$_2$- with N-COOC$_2$H$_5$ | biphenyl | RS | — | 1732, 1594, 1404, 1155 | — |
| 38 | 1H-indol-3-yl-CH$_2$- | H$_3$CO-biphenyl (4'-OMe) | R | 188–190 | 1607, 1594, 1294, 1153 | C$_{24}$H$_{22}$N$_2$O$_5$S.0.5H$_2$O Calc. C: 62.73 H: 5.04 N: 6.10 S: 6.98 Foun. C: 62.75 H: 5.08 N: 6.31 S: 7.05 |
| 39 | 1H-indol-3-yl-CH$_2$- | H$_3$CO-biphenyl (3'-OMe) | R | 90–93 | 1724, 1594, 1326, 1159 | C$_{24}$H$_{22}$N$_2$O$_5$S.0.8H$_2$O Calc. C: 62.00 H: 5.12 N: 6.03 S: 6.90 Foun. C: 62.03 H: 5.06 N: 6.08 S: 6.82 |
| 40 | 1H-indol-3-yl-CH$_2$- | H$_3$C-biphenyl | R | 149–152 | 1685, 1349, 1166 | — |
| 41 | 1H-indol-3-yl-CH$_2$- | F-biphenyl | R | 104–107 | 1725, 1599, 1372, 1173 | — |
| 42 | 1H-indol-3-yl-CH$_2$- | H$_3$CS-biphenyl | R | 167–169 | 1745, 1653, 1391, 1147 | — |
| 43 | (CH$_3$)$_2$CH— | biphenyl | R | 155–157 | 1714, 1594, 1334, 1166 | C$_{17}$H$_{19}$NO$_4$S.0.1CF$_3$COOH Calc. C: 59.99 H: 5.58 N: 4.06 S: 9.30 Foun. C: 60.37 H: 5.74 N: 4.13 S: 9.76 |

TABLE 11

(Ia)

$$R^{18}SO_2NH-\underset{*}{CH}(R^1)-COOH$$

| Example No. | R¹ | R¹⁸ | * | mp (decomp.) (°C.) | IR (ν cm⁻¹) (KBr) | Elemental analysis |
|---|---|---|---|---|---|---|
| 44 | (CH₃)₂CH— | 4'-tBu-biphenyl-4-yl | R | 196–197 | 1724, 1340, 1328, 1167 | C₂₁H₂₇NO₄S·0.3H₂O Calc. C: 63.87 H: 7.04 N: 3.55 S: 8.12 Foun. C: 63.84 H: 6.86 N: 3.42 S: 8.01 |
| 45 | (CH₃)₂CH— | 4'''-terphenyl-4-yl (p-terphenyl) | R | 241–243 | 1734, 1719, 1324, 1160 | C₂₃H₂₃NO₄S·0.3H₂O Calc. C: 66.58 H: 5.73 N: 3.38 S: 7.73 Foun. C: 66.45 H: 5.52 N: 3.24 S: 7.56 |
| 46 | (CH₃)₂CH— | 4'-CF₃-biphenyl-4-yl | R | 157–159 | 1670, 1375, 1148 | — |
| 47 | (CH₃)₂CH— | 4'-OCH₃-biphenyl-4-yl | R | 175–176 | 1717, 1694, 1349, 1165 | — |
| 48 | (CH₃)₂CH— | 4'-F-biphenyl-4-yl | R | 145–147 | 1634, 1334, 1158 | C₁₇H₁₈FNO₄S Calc. C: 58.11 H: 5.16 F: 5.41 N: 3.99 S: 9.12 Foun. C: 58.11 H: 5.17 F: 5.86 N: 3.92 S: 9.69 |
| 49 | (CH₃)₂CH— | 4'-CH₃-biphenyl-4-yl | R | 183–186 | 1681, 1319, 1162 | — |
| 50 | C₆H₅—CH₂— | 4''-OCH₃-p-terphenyl-4-yl | R | 183–184 | 1725, 1340, 1159 | — |
| 51 | C₆H₅—CH₂— | p-terphenyl-4-yl | R | 224–226 | 1750, 1324, 1159 | C₂₇H₂₃NO₄S·0.7H₂O Calc. C: 68.98 H: 5.23 N: 2.98 S: 6.82 Foun. C: 69.08 H: 5.09 N: 2.91 S: 6.73 |

TABLE 12

(Ia)

$$R^{18}SO_2NH-\underset{*}{CH}(R^1)-COOH$$

| Example No. | R¹ | R¹⁸ | * | mp (decomp.) (°C.) | IR (ν cm⁻¹) (KBr) | Elemental analysis |
|---|---|---|---|---|---|---|
| 52 | C₆H₅—CH₂— | 4'-CH₃-biphenyl-4-yl | R | 157–160 | 1685, 1349, 1166 | — |
| 53 | C₆H₅—CH₂— | 4'-F-biphenyl-4-yl | R | 111–112 | 1691, 1567, 1390, 1159 | — |

TABLE 12-continued $$\text{R}^{18}\text{SO}_2\text{NH}-\overset{R^1}{\underset{*}{C}}-\text{COOH} \quad (Ia)$$

| Example No. | $R^1$ | $R^{18}$ | * | mp (decomp.) (° C.) | IR ($\nu$ cm$^{-1}$) (KBr) | Elemental analysis |
|---|---|---|---|---|---|---|
| 54 | benzyl (PhCH$_2$—) | H$_3$CS-biphenyl- | R | 194–195 | 1749, 1592 1323, 1164 | — |
| 55 | (CH$_3$)$_2$CH— | H$_3$CS-biphenyl- | R | 197–199 | 1746, 1337 1164 | C$_{18}$H$_{21}$NO$_4$S$_2$.0.2H$_2$O Calc. C: 56.43 H: 5.63 N: 3.66 S: 16.74 Foun. C: 56.74 H: 5.67 N: 3.86 S: 16.35 |
| 56 | (1H-indol-3-yl)methyl | HOOC-phenyl- | R | 108–110 | 1649, 1337 1165 | — |
| 57 | (1H-indol-3-yl)methyl | (H$_3$C)$_2$N-naphthyl- | R | 187–190 | 1588, 1308 1141 | — |
| 58 | (1-COOC$_2$H$_5$-indol-3-yl)methyl | thiophen-2-yl-phenyl- | R | 239–243 | 1744, 1592 1323, 1160 | C$_{21}$H$_{18}$N$_2$O$_4$S$_2$.0.3H$_2$O Calc. C: 58.40 H: 4.34 N: 6.45 S: 14.85 Foun. C: 58.40 H: 4.44 N: 6.58 S: 14.57 |
| 59 | (1H-indol-3-yl)methyl | 2-Cl-3-NO$_2$-phenyl- | R | 222–224 | 1751, 1734 1537, 1347 1172 | C$_{17}$H$_{14}$ClN$_3$O$_6$S.0.3H$_2$O Calc. C: 47.48 H: 3.44 Cl: 8.39 N: 9.65 S: 7.52 Foun. C: 47.57 H: 3.43 Cl: 8.26 N: 9.79 S: 7.47 |

TABLE 13

$$\text{R}^{18}\text{SO}_2\text{NH}-\overset{R^1}{\underset{*}{C}}-\text{CONHOH} \quad (Ib)$$

| Example No. | $R^1$ | $R^{18}$ | * | mp (decomp.) (° C.) | IR ($\nu$ cm$^{-1}$) (KBr) | $^1$H-NMR($\delta$ ppm) d$_6$-DMSO |
|---|---|---|---|---|---|---|
| 60 | benzyl (PhCH$_2$—) | phenoxy-phenyl- | R | foam | 3700–2400 br, 3277, 1669, 1325, 1152 | 2.60(dd, J=8.7, 13.7Hz, 1H), 2.79(dd, J=6.0, 13.7Hz, 1H), 3.75(ddd, J=6.0, 8.7, 9.0, 1H), 6.94(d, J=8.9Hz, 2H) |
| 61 | (1H-indol-3-yl)methyl | phenoxy-phenyl- | R | 115–118 | 3302, 1667, 1324, 1153(Nujol) | 2.71(dd, J=7.0, 14.4Hz, 1H), 2.96(dd, J=7.0, 14.2Hz, 1H), 3.78(t, J=7.6Hz, 1H) |

TABLE 13-continued (Ib)

R¹⁸SO₂NH—*C(R¹)H—CONHOH

| Example No. | R¹ | R¹⁸ | * | mp (decomp.) (° C.) | IR (ν cm⁻¹) (KBr) | ¹H-NMR(δ ppm) d₆-DMSO |
|---|---|---|---|---|---|---|
| 62 | 1H-indol-3-ylmethyl | 4-phenoxyphenyl | S | — | 3406, 1670, 1582, 1325, 1153 | 2.71(dd, J=7.9, 14.4Hz, 1H), 2.96(dd, J=7.6, 14.4Hz, 1H), 3.78(dd, J=7.2, 7.3Hz, 1H) |
| 63 | (CH₃)₂CH— | 4-phenoxyphenyl | R | 149–151 | 3268, 1634, 1584, 1336, 1157 | 0.76(d, J=6.6Hz, 6H), 1.77(m, 1H), 3.26(m, 1H) |
| 64 | 1-methyl-1H-indol-3-ylmethyl | 4-phenoxyphenyl | RS | — | 3314, 1669, 1582, 1420, 1328, 1154 | 2.71(dd, J=7.9, 14.2Hz, 1H), 2.93(dd, J=6.5, 14.3Hz, 1H), 3.65(s, 3H), 3.78(dd, J=7.1, 7.2Hz, 1H) |
| 65 | 5-methyl-1H-indol-3-ylmethyl | 4-phenoxyphenyl | RS | — | 3405, 1671, 1582, 1487, 1324, 1154 | 2.34(s, 3H), 2.65(dd, J=7.8, 14.1Hz, 1H), 2.93(dd, J=7.6, 14.4Hz, 1H), 3.75(dd, J=6.8, 7.7Hz, 1H) |
| 66 | 5-fluoro-1H-indol-3-ylmethyl | 4-phenoxyphenyl | RS | — | 3317, 1670, 1582, 1488, 1323, 1153 | 2.71(dd, J=8.9, 14.4Hz, 1H), 2.89(dd, J=6.6, 14.4Hz, 1H), 3.75(dd, J=6.5, 6.8Hz, 1H) |
| 67 | 1-acetyl-1H-indol-3-ylmethyl | 4-phenoxyphenyl | RS | — | 3421, 1702, 1676, 1582, 1354, 1328, 1153 | 2.54(s, 3H), 2.69–2.89(m, 2H), 3.87(m, 1H) |

TABLE 14

(Ia)

R¹⁸SO₂NH—*C(R¹)H—COOH

| Example No. | R¹ | R¹⁸ | * | mp (decomp.) (° C.) | IR (ν cm⁻¹) (KBr) | ¹H-NMR(δ ppm) d₆-DMSO |
|---|---|---|---|---|---|---|
| 60 | benzyl | 4-phenoxyphenyl | R | 108–109 | 2400–3600 br, 3345, 3213, 1735, 1700, 1346, 1163 | 2.72(dd, J=8.7, 13.6Hz, 1H), 2.94(dd, J=5.6, 13.6Hz, 1H), 3.84(ddd, J=5.6, 8.7, 8.7Hz, 1H), 8.23(d, J=8.7Hz, 1H) |
| 61 | 1H-indol-3-ylmethyl | 4-phenoxyphenyl | R | 82–87 | 3410, 3276, 1724, 1582, 1488, 1331, 1152(Nujol) | 2.88(dd, J=7.4, 15.2Hz, 1H), 3.07(dd, J=6.2, 14.4Hz, 1H), 3.83(m, 1H), 8.08(m, 1H), 10.80(s, 1H), 12.70(br, 1H) |

TABLE 14-continued
(Ia)
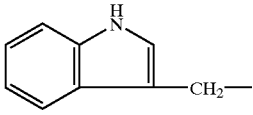
| Example No. | R¹ | R¹⁸ | * | mp (decomp.) (° C.) | IR (ν cm⁻¹) (KBr) | ¹H-NMR(δ ppm) d₆-DMSO |
|---|---|---|---|---|---|---|
| 62 | 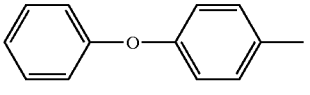 | 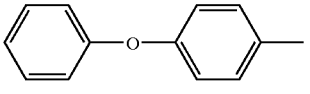 | S | foam | 3412, 1724, 1582, 1488, 1332, 1152 | 2.81–3.12(m, 2H), 3.88(m, 1H), 8.19(d, J=8.4Hz, 1H) |
| 63 | (CH₃)₂CH— | 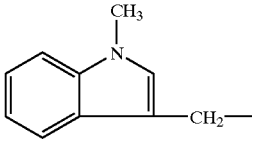 | R | 137–138 | 3154, 1720, 1688, 1583, 1488, 1251 | 0.89(d, J=7.0Hz, 3H), 0.98(d, J=6.8Hz, 3H), 2.12(m, 2H), 3.80(dd, J=4.7, 9.7Hz, 1H), 5.17(d, J=9.6Hz, 1H) |
| 64 | 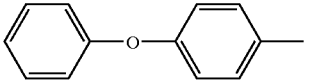 | 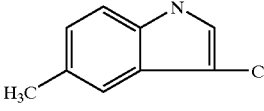 | RS | — | 3273, 1724, 1582, 1487, 1331, 1198, 1153 | 2.78–3.10(m, 2H), 3.67(s, 3H), 3.86(m, 1H) |
| 65 | 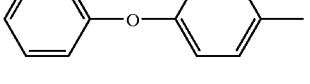 | 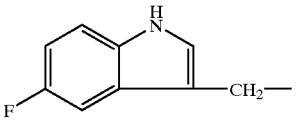 | RS | — | 3409, 3281, 1725, 1582, 1331, 1197, 1153 | 2.34(s, 3H), 2.75–3.08 (m, 2H), 3.86(m, 1H), 8.19(d, J=8.4Hz, 1H) |
| 66 | 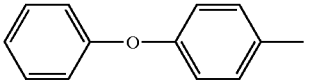 | 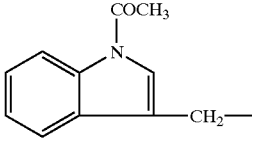 | RS | — | 3415, 1725, 1582, 1488, 1329, 1196, 1174, 1152 | 2.78–3.08(m, 2H), 3.85(m, 1H), 8.18(d, J=8.6Hz, 1H) |
| 67 | 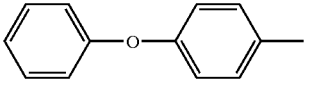 | 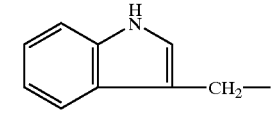 | RS | 236–237 | 3296, 1742, 1647, 1604, 1581, 1342, 1334, 1152 | 2.55(s, 3H), 2.79–3.11 (m, 2H), 3.98(m, 1H) |
TABLE 15
(Ia)
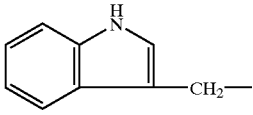
| Example No. | R¹ | R¹⁸ | * | mp (decomp.) (° C.) | IR (ν cm⁻¹) (KBr) | Elemental analysis |
|---|---|---|---|---|---|---|
| 68 | 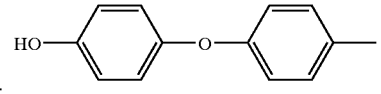 | HO—⟨phenyl⟩—O—⟨phenyl⟩— | R | >240 | 1608, 1590, 1507, 1232, 1157 | — |

TABLE 15-continued (Ia)

$$R^{18}SO_2NH-\overset{R^1}{\underset{*}{C}}H-COOH$$

| Example No. | R¹ | R¹⁸ | * | mp (decomp.) (° C.) | IR (ν cm⁻¹) (KBr) | Elemental analysis |
|---|---|---|---|---|---|---|
| 69 | 3-(N-SO₂CH₃-indolyl)-CH₂— | 4-phenoxyphenyl | RS | — | 1735, 1583, 1362, 1171 | C₂₄H₂₂N₂O₇S₂ Calc. C: 56.02 H: 4.31 N: 5.44 S: 12.46 Foun. C: 55.75 H: 4.40 N: 5.41 S: 12.21 |
| 70 | 3-(N-COOC₂H₅-indolyl)-CH₂— | 4-phenoxyphenyl | RS | — | 1733, 1583, 1150 | — |

TABLE 16

(Ib)

$$R^{18}SO_2NH-\overset{R^1}{\underset{*}{C}}H-CONHOH$$

| Example No. | R¹ | R¹⁸ | * | mp (decomp.) (° C.) | IR (ν cm⁻¹) (KBr) | ¹H-NMR(δ ppm) d₆-DMSO |
|---|---|---|---|---|---|---|
| 71 | C₆H₅—CH₂— | CH₃(CH₂)₄—(4-phenyl)— | R | 129–131 | 3700–2400 br, 3247, 1636, 1337, 1160 | 0.90(t, J=6.8Hz, 3H), 1.22–1.40 (m, 4H), 1 52–1.67(m, 2H), 2.62 (t, J=7.7Hz, 2H), 2 86(dd, J=8.4, 13.7Hz, 1H), 3.02(dd, J=5.7, 13.7Hz, 1H) (CDCl₃) |
| 72 | C₆H₅—CH₂— | CH₃(CH₂)₇— | R | oil | 3700–2400 br, 1663, 1320, 1145 (film) | 0.87(t, J=6.3Hz, 3H), 2.50(t, J=7.4Hz, 2H), 2.76(dd, J=9.6, 14.0Hz, 1H), 2.87(dd, J=5.8, 14.0Hz, 1H), 3.84(dd, J=5.8, 9.6Hz, 1H), |
| 73 | C₆H₅—CH₂— | CH₃(CH₂)₃— | R | oil | 3600–2400 br, 3262, 1673, 1321, 1142 (CHCl₃) | 0.79(t, J=7.0Hz, 3H), 2.32–2.56(m, 2H), 2.92(m, 1H), 3.26 (m, 1H), |
| 74 | 3-(1H-indolyl)-CH₂— | 5-chloro-2,3-dimethylbenzothiophen-yl | R | — | — | — |
| 75 | C₆H₅—CH₂— | 4-benzylphenyl | R | 85–86 | 3700–2200 (br), 3262, 1639, 1332, 1156 | 2.80(m, 1H), 2.96(m, 1H), 3.94 (s, 2H), 3.86(m, 1H), 6.80–7.52 (m, 10H), 7.08(A₂B₂q,J=7.5Hz, 2H), 7.42(A₂B₂q, J=7.5Hz, 2H)(CDCl₃) |
| 76 | 3-(1H-indolyl)-CH₂— | 4-morpholinyl | R | — | — | — |

TABLE 17

$$R^{18}SO_2NH-\overset{R^1}{\underset{*}{C}H}-CONHOH \quad (Ib)$$

| Example No. | R$^1$ | R$^{18}$ | * | mp (decomp.) (°C.) | IR (ν cm$^{-1}$) (KBr) | $^1$H-NMR(δ ppm) d$_6$-DMSO |
|---|---|---|---|---|---|---|
| 77 | PhCH$_2$— | PhCH$_2$— | R | 138–139 | 3700–2400 (br), 3312, 1629, 1329, 1144 | 2.79(dd, J=8.5, 13.4Hz, 1H), 2.89 (dd, J=6.0, 13.4Hz, 1H), 3.81(dd, J=6.0, 8.5Hz, 1H), 6.55(d, J=15.5Hz, 1H) |
| 78 | PhCH$_2$— | PhCH$_2$— | R | 69–70 | 3700–220 (br), 1670, 1318, 1152 | 2.78(dd, J=8.6, 13.4Hz, 1H), 2.91(dd, J=6.0, 13.4Hz, 1H), 3.92(ABq, J=13.5Hz, 1H), 3.90(m, 1H), 9.01(s, 1H), 10.78(s, 1H) |
| 79 | indol-3-yl-CH$_2$— | cyclohexyl-NH— | R | — | — | — |

TABLE 18

$$R^{18}SO_2NH-\overset{R^1}{\underset{*}{C}H}-COOH \quad (Ia)$$

| Example No. | R$^1$ | R$^{18}$ | * | mp (decomp.) (°C.) | IR (ν cm$^{-1}$) (KBr) | $^1$H-NMR(δ ppm) d$_6$-DMSO |
|---|---|---|---|---|---|---|
| 71 | PhCH$_2$— | CH$_3$(CH$_2$)$_4$—C$_6$H$_4$— | R | 121–122 | 2300–3700 br, 3426, 3318, 1713, 1330, 1159 | 0.89(t, J=6.7Hz, 3H), 2.62(t, J=7.6Hz, 2H), 2.96(dd, J=7.0, 13.9Hz, 1H), 3.10(dd, J=5.4, 13.9Hz, 1H), 4.19(dt, J=6.9, 8.2Hz, 1H), 5.30(d, J=8.2Hz, 1H), |
| 72 | PhCH$_2$— | CH$_3$(CH$_2$)$_7$— | R | oil | 2400–3600 br, 3340, 1736, 1334, 1142 (CHCl$_3$) | 0.88(t, J=6.9Hz, 3H), 2.55–2.73(m, 2H), 2.97(dd, J=8.4, 13.8Hz, 1H), 3.24(dd, J=4.8, 13.8Hz, 1H), 4.35(m, 1H), 4.98(m, 1H) (CDCl$_3$) |
| 73 | PhCH$_2$— | CH$_3$(CH$_2$)$_3$— | R | 89–90 | 2300–3700 br, 3240, 1725, 1341, 1144 | 0.84(t, J=7.1Hz, 3H), 2.57–2.70 (m, 2H), 2.97(dd, J=8.4, 13.9Hz, 1H), 3.25(dd, J=4.8, 13.9Hz, 1H), 4.35(m, 1H), 4.96(d, J=9.6Hz, 1H) (CDCl$_3$) |
| 74 | indol-3-yl-CH$_2$— | 5-Cl-3-CH$_3$-2-benzothienyl— | R | >250 | 3421, 1580, 1333, 1421, 1153 | 2.41(s, 3H), 3.01(dd, J=6.0, 14.4Hz, 1H), 3.12(dd, J=4.5, 14.4Hz, 1H), 3.67(t, J=5.4Hz, 1H), 6.79(m, 1H), 6.89(m, 1H), 10.59(s, 1H) |
| 76 | indol-3-yl-CH$_2$— | morpholino— | R | foam | 3413, 1594, 1456, 1416, 1157 | 3.03(dd, J=6.5, 15.1Hz, 1H), 3.15(dd, J=4.7, 14.1Hz, 1H), 3.64 (t, J=5.1Hz, 1H), 10.68(s, 1H) |
| 77 | PhCH$_2$— | PhCH=CH— | R | — | 2400–3700 br, 3252, 1765, 1725, 1301, 1140 | 2.81(dd, J=9.2, 13.7Hz, 1H), 3.03(dd, J=5.4, 13.7Hz, 1H), 3.94 (dt, J=5.4, 9.2Hz, 1H), 6.66(d, J=15.2Hz, 1H), 7.16(d, J=15.2Hz, 1H), 8.01(d, J=9.2Hz, 1H) |

TABLE 18-continued
(Ia)
$$R^{18}SO_2NH-\overset{R^1}{\underset{*}{CH}}-COOH$$
| Example No. | R¹ | R¹⁸ | * | mp (decomp.) (° C.) | IR (ν cm⁻¹) (KBr) | ¹H-NMR(δ ppm) d₆-DMSO |
|---|---|---|---|---|---|---|
| 78 | 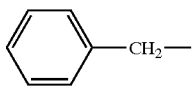 | 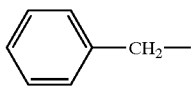 | R | — | 2200–3700 br, 3268, 1726, 1321, 1152 (film) | 2.81(dd, J=9.2, 13.7Hz, 1H), 3.00 (dd, J=5.6, 13.7Hz, 1H), 4.01 (ABq, J=137.7Hz, 2H), 4.01(m, 1H), 7.65(d, J=8.3Hz, 1H) |
| 79 | 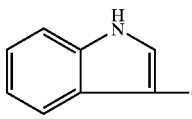 | 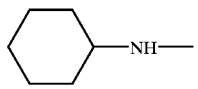 | R | — | 3413, 2931, 1720, 1585, 1455, 1421, 1313, 1144 | 0.90–1.68(m, 9H), 1.78(m, 1H), 2.74(m, 1H), 3.00–3.20(m, 2H), 3.77(m, 1H) 6.45(br.s, 1H), 6.77(br.s, 1H) |
TABLE 19
(Ia)
$$R^{18}SO_2NH-\overset{R^1}{\underset{*}{CH}}-COOH$$
| Example No. | R¹ | R¹⁸ | * | mp (decomp.) (° C.) | IR (ν cm⁻¹) (KBr) | Elemental analysis |
|---|---|---|---|---|---|---|
| 80 | 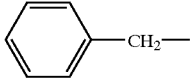 | 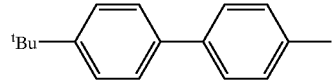 | R | 153–155 | 1704, 1596 1349, 1164 | — |
| 81 | 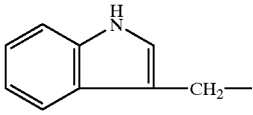 | n-C₈H₁₇— | R | >130 | 1576, 1356 1139 | — |
| 82 | 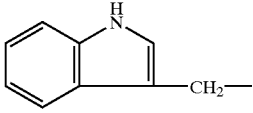 | 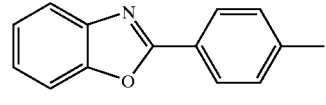 | R | 128–130 | 1732, 1342 1167 | C₂₄H₁₉N₃O₅S.1.3H₂O Calc. C: 59.45 H: 4.49 N: 8.67 S: 6.61 Foun. C: 59.43 H: 4.45 N: 8.59 S: 6.58 |
| 83 | 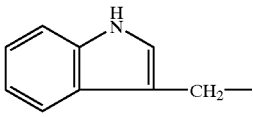 | 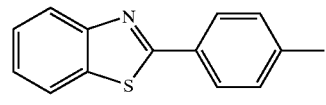 | R | 210–214 | 1745, 1590 1316, 1157 | — |
| 84 | 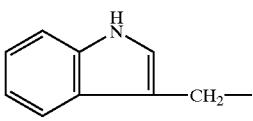 | 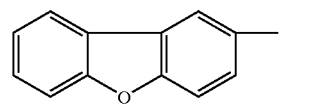 | R | 198–200 | 1594, 1456 1200, 1188 | — |

TABLE 20

(Ib)

$$R^{18}SO_2NH-\underset{*}{CH}(R^1)-CONHOH$$

| Example No. | R$^1$ | R$^{18}$ | * | mp (decomp.) (° C.) | IR (ν cm$^{-1}$) (KBr) | $^1$H-NMR(δ ppm) d$_6$-DMSO |
|---|---|---|---|---|---|---|
| 85 | phenyl-CH$_2$- | phenyl-N=N-(4-methylphenyl)- | R | 157–160 | 3700–2400 br, 3273, 1633, 1338, 1166 | 2.65(dd, J=8.9, 13.6Hz, 1H), 2.82(dd, J=6.6, 13.6Hz, 1H), 3.86(m, 1H), 7.75(d, J=7.8Hz, 2H), 7.87(d, J=8.7Hz, 2H) |
| 86 | phenyl-CH$_2$- | Me$_2$N-(phenyl)-N=N-(4-methylphenyl)- | R | 138–142 | 3700–2400 br, 2921, 1672, 1314, 1165, | 2.62(dd, J=8.6, 13.5Hz, 1H), 2.81(dd, J=6.5, 13.6Hz, 1H), 3.09(s, 6H), 3.83(m, 1H), 6.86 (d, J=9.0Hz, 2H), 7.83 (d, J=8.8Hz, 2H) |
| 87 | phenyl-CH$_2$- | phenyl-NH-C(=O)-NH-(4-methylphenyl)- | S | 206–207 | 3700–2400 (br), 3357, 1686, 1641, 1314, 1155 | 2.57(dd, J=8.3, 13.6Hz, 1H), 2.79(dd, J=6.0, 13.6Hz, 1H), 3.76(m, 1H), 8.02(d, J=8.7Hz, 1H), 8.80(s, 1H), 8.85(d, J=1.7Hz, 1H), 9.06(s, 1H), 10.59(d, J=1.7Hz, 1H) |

TABLE 21

(Ia)

$$R^{18}SO_2NH-\underset{*}{CH}(R^1)-COOH$$

| Example No. | R$^1$ | R$^{18}$ | * | mp (decomp.) (° C.) | IR(ν cm$^{-1}$) (KBr) | $^1$H-NMR(δ ppm) d$_6$-DMSO |
|---|---|---|---|---|---|---|
| 85 | phenyl-CH$_2$- | phenyl-N=N-(4-methylphenyl)- | R | 172–174 | 2400–3600br, 3426, 3296, 1698, 1350, 1167 | 2.75(dd, J=9.1, 13.7Hz, 1H), 2.98 (dd, J=5.5, 13.7Hz, 1H), 3.96(ddd, J=5.5, 9.1, 9.1Hz, 1H), 8.51(d, J+9.1Hz, 1H) |
| 86 | phenyl-CH$_2$- | Me$_2$N-(phenyl)-N=N-(4-methylphenyl)- | R | 93–94 | 2200–3700br, 3431, 1735, 1391, 1154 | 2.74(dd, J=9.1, 13.6Hz, 1H), 2.96 (dd, J=5.7, 13.6Hz, 1H), 3.09(s, 6H), 3.93(dt, J=5.7, 9.1Hz, 1H), 8.39(d, J=9.1Hz, 1H) |
| 87 | phenyl-CH$_2$- | phenyl-NH-C(=O)-NH-(4-methylphenyl)- | S | 203–204 | 2300–3700br, 3358, 3262, 1718, 1686, 1660, 1313, 1159 | 2.71(dd, J=9.1, 13.7Hz, 1H), 2.93 (dd, J=5.6, 13.7Hz, 1H), 3.84(dt, J=5.6, 9.1Hz, 1H), 8.11(d, J= 9.1Hz, 1H), 8.78(s, 1H), 9.06(s, 1H) |

TABLE 22

(Ia)

R¹⁸SO₂NH—*CH(R¹)—COOH

| Example No. | R¹ | R¹⁸ | * | mp (decomp.) (° C.) | IR (ν cm⁻¹) (KBr) | Elemental analysis |
|---|---|---|---|---|---|---|
| 88 | indol-3-yl-CH₂— | 4-(PhNHC(O))-C₆H₄— | R | 103–106 | 1719, 1390, 1229 | — |
| 89 | (CH₃)₂CH— | Ph-SO₂-NH-C₆H₄— | R | 96–99 | 1734, 1461, 1327, 1158 | C₁₇H₂₀N₂O₆S₂.0.9Ethylether<br>Calc. C: 51.63 H: 6.10 N: 5.85 S: 13.38<br>Foun. C: 51.23 H: 6.17 N: 5.87 S: 13.11 |
| 90 | (CH₃)₂CH— | Ph-SO₂-NH-N=CH-C₆H₄— | R | 110–112 | 1724, 1325, 1168 | C₁₈H₂₁N₃O₆S₂.0.8Ethylether<br>Calc. C: 51.05 H: 5.86 N: 8.42 S: 12.86<br>Foun. C: 50.75 H: 5.89 N: 8.15 S: 12.47 |
| 91 | Ph-CH₂— | 4-Br-C₆H₄-(4-)-SO₂-NH-C₆H₄— | R | 98–101 | 1735, 1598, 1327, 1185 | C₂₁H₁₉BrN₂O₆S₂.0.5CF₃COOH<br>Calc. C: 44.30 H: 3.30 Br: 13.40 N: 4.70 S: 10.75<br>Foun. C: 44.62 H: 3.52 Br: 13.07 N: 4.64 S: 10.85 |

EXAMPLE 92

(Method B)

HCl·H₂N–CH(iPr)–COOMe (XV-2) → Process 1 →

Br–(thiophene)–SO₂–NH–CH(iPr)–COOMe (XVII-1) → Process 2 →

MeO–C₆H₄–C≡C–(thiophene)–SO₂–NH–CH(iPr)–COOMe (XVIII-1) → Process 3 →

MeO–C₆H₄–C≡C–(thiophene)–SO₂–NH–CH(iPr)–COOH (Ia-2-1)

Process 1

To a solution of D-valine methylester hydrochloride (XV-2) (755 mg, 4.5 mmol) in dichloromethane (12 ml) was added N-methylmorpholine (1.49 ml, 3×4.5 mmol) and 5-bromo-2-thiophensulfonyl chloride (1.24 g, 1.05×4.5 mmol) was added under ice-cooling. After being stirred for 15 h at room temperature, the reaction mixture was washed with 2N HCl, 5% NaHCO₃, and water. The organic layer was concentrated in vacuo, and dried over Na₂SO₄. The residue was subjected to silica gel column chromatography and the fractions eluting with ethyl acetate/hexane=1/3 were collected and washed with n-hexane to give 1.32 g of the desired compound (XVII-1). Yield 82%. mp. 109–110° C.

Elemental analysis C₁₀H₁₄BrNO₄S₂
Caldc.: C, 33.71; H, 3.96; Br, 22.43; N, 3.93; S,1 8.00.
Found: C, 33.75; H, 3.89; Br, 22.43; N, 3.96; S, 17.86.
[α]$_D$: −34.5±0.7(c=1.012 CHCl₃ 25° C.)
IR(CHCl₃, ν max cm⁻¹)1737,1356,1164,1138
NMR (CDCl₃, δ ppm): 0.89(d, J=6.8 Hz, 3H), 1.00(d, J=6.8 Hz, 3H), 2.00 (m, 1H), 3.60(s, 3H), 3.83(dd, J=5.2, 10.0 Hz, 1H), 5.20(d, J=10.0 Hz, 1H), 7.04(d, J=4.1 Hz, 1H), 7.32(d, J=4.1 Hz, 1H)

Process 2

To a degassed solution of 400 mg (1.12 mmol) of compound (XVII-1) in 5 ml of dimethylformamide was added 222 mg (1.5×1.12 mmol) of 4-methoxyphenylacetylene and 21 mg(0.1×1.12 mmol) of copper iodide (I) under an argon atmosphere. Then 39 mg (0.05×1.12 mmol) of bis(triphenylphosphine)palladium dichloride (II) and 0.47 ml (3×1.12 mmol) of triethylamine were added to the reaction mixture. The resulting mixture was degassed and stirred overnight under an argon atmosphere at 50° C. The reaction mixture was diluted with ethyl acetate. The organic later was washed with 1N HCl, 5% NaHCO₃, and water, dried over Na₂SO₄, and concentrated in vacuo. The resulting residue was column chromatographed on silica gel. The fractions eluting with n-hexane/ethyl acetate=2/1 were collected and recrystallized from ethyl acetate/n-hexane to give 392 mg of the desired compound (XVIII-1). Yield 86%. mp. 131–132° C.

Elemental analysis C₁₉H₂₁NO₅S₂.0.2 H₂O
Caldc.: C, 55.51; H, 5.25; N, 3.41; S, 15.60. Found: C, 55.80; H, 5.19; N, 3.38; S, 15.36.
IR(KBr, ν max cm⁻¹): 3268,2203,1736,1604,1524,1348, 1164.

NMR(CDCl$_3$, δ ppm): 0.90(d, J=6.6 Hz, 3H), 1.00(d, J=7.0 Hz, 3H), 2.00(m, 1H), 3.60(s, 3H), 3.84(s, 3H), 3.86(dd, J=5.0, 10.2 Hz, 1H), 5.21(d, J=10.2 Hz, 1H), 6.90(d, J=9.0 Hz, 2H), 7.44(d, J=9.0 Hz, 2H), 7.12(d, J=4.0 Hz, 1H), 7.44(d, J=4.0 Hz, 1H).

Process 3

To a solution of 407 mg (1 mmol) of compound (XVII-1) in 8 ml of tetrahydrofuran and 8 ml of methanol was added 5.1 ml of 1N NaOH. The resulting mixture was stirred for 6 h at 60° C. The reaction mixture was concentrated in vacuo to remove an organic solvent, and the residue was diluted with ethyl acetate. The mixture was acidified with aqueous solution of citric acid and extracted with ethyl acetate. The organic layer was washed with brine, dried over Na$_2$SO$_4$, and concentrated in vacuo to give 373 mg of compound (Ia-2-1). Yield 100%. mp. 147–148° C.

IR (KBr, ν max cm$^{-1}$) 1710,1604,1351,1216.

Elemental analysis C$_{18}$H$_{19}$NO$_5$S$_2$.0.2H$_2$O

Caldc.: C, 54.45; H, 4.92; N, 3.53; S, 16.15. Found: C, 54.39; H, 4.93; N, 3.79; S, 15.96.

EXAMPLE 93–156

The compounds which were shown in Tables 23 to 30 were synthesized in a manner similar to those described in Example 92.

TABLE 23

(Ia)

R$^{18}$SO$_2$NH—*CH(R$^1$)—COOH

| Example No. | R$^1$ | R$^{18}$ | * | mp (decomp.) (° C.) | IR (ν cm$^{-1}$) (KBr) | Elemental analysis |
|---|---|---|---|---|---|---|
| 93 | indol-3-yl-CH$_2$– | C$_6$H$_5$–C≡C–C$_6$H$_4$– | R | 165–170 | 1590, 1316 1137 | — |
| 94 | indol-3-yl-CH$_2$– | H$_3$CO–C$_6$H$_4$–C≡C–C$_6$H$_4$– | R | 223–226 | 1747, 1323 1134 | C$_{26}$H$_{22}$N$_2$O$_5$S Calc. C: 65.81 H: 4.67 N: 5.90 S: 6.76 Foun. C: 65.34 H: 4.90 N: 5.56 S: 6.40 |
| 95 | indol-3-yl-CH$_2$– | HO–C$_6$H$_4$–C≡C–C$_6$H$_4$– | R | 216–218 | 1724, 1325 1135 | — |
| 96 | indol-3-yl-CH$_2$– | H$_3$COCO–C$_6$H$_4$–C≡C–C$_6$H$_4$– | R | 111–114 | 1739, 1336 1163 | — |
| 97 | indol-3-yl-CH$_2$– | F–C$_6$H$_4$–C≡C–C$_6$H$_4$– | R | 178–180 | 1710, 1511 1329, 1161 | — |
| 98 | indol-3-yl-CH$_2$– | O$_2$N–C$_6$H$_4$–C≡C–C$_6$H$_4$– | R | 105–108 | 1725, 1618 1373, 1163 | — |
| 99 | indol-3-yl-CH$_2$– | HOOC–C$_6$H$_4$–C≡C–C$_6$H$_4$– | R | >250 | 1706, 1606 1350, 1164 | C$_{26}$H$_{20}$N$_2$O$_6$.0.4H$_2$O Calc. C: 63.00 H: 4.23 N: 5.65 S: 6.47 Foun. C: 62.99 H: 4.32 N: 5.82 S: 6.76 |
| 100 | indol-3-yl-CH$_2$– | H$_2$N–C$_6$H$_4$–C≡C–C$_6$H$_4$– | R | 176–177 | 1735, 1633 1321, 1173 | C$_{25}$H$_{21}$N$_3$O$_4$S.0.8H$_2$O Calc. C: 63.36 H: 4.81 N: 8.87 S: 6.77 Foun. C: 63.45 H: 4.92 N: 8.77 S: 6.57 |

TABLE 24

(Ia)

structure: R¹⁸SO₂NH—*CH(R¹)—COOH

| Example No. | R¹ | R¹⁸ | * | mp (decomp.) (° C.) | IR (ν cm⁻¹) (KBr) | Elemental analysis |
|---|---|---|---|---|---|---|
| 101 | indol-3-ylmethyl | 4-methylphenyl-C≡C-phenyl- | R | 227–229 | 1736, 1618 1398, 1168 | $C_{26}H_{22}N_2O_4S \cdot 0.2H_2O$ Calc. C: 67.57 H: 4.89 N: 6.06 S: 6.94 Foun. C: 67.66 H: 4.77 N: 6.09 S: 6.71 |
| 102 | indol-3-ylmethyl | HC≡C-phenyl-C≡C-phenyl- | R | 230–233 | 1735–1654 1399, 1164 | — |
| 103 | indol-3-ylmethyl | Me₂N-phenyl-C≡C-phenyl- | R | 234–236 | 1732, 1631 1372, 1148 | — |
| 104 | indol-3-ylmethyl | H₃CO-phenyl-C≡C-(2-NO₂)phenyl- | R | >200 decomp. | 1600, 1558 1336, 1171 | — |
| 105 | $(CH_3)_2CH-$ | H₃CO-phenyl-C≡C-phenyl- | R | 146–149 | 1795, 1718 1331, 1166 | — |
| 106 | $(CH_3)_2CH-$ | O₂N-phenyl-C≡C-phenyl- | R | 231–232 | 1719, 1595 1344, 1167 | $C_{19}H_{18}N_2O_6S \cdot 0.1H_2O$ Calc. C: 56.46 H: 4.54 N: 6.93 S: 7.93 Foun. C: 56.30 H: 4.37 N: 7.14 S: 7.85 |
| 107 | $(CH_3)_2CH-$ | H₂N-phenyl-C≡C-phenyl- | R | 166–169 | 1728, 1631 1372, 1148 | — |
| 108 | $(CH_3)_2CH-$ | HO-phenyl-C≡C-phenyl- | R | 163–165 | 1728, 1332 1172 | — |

TABLE 25

(Ia)

structure: R¹⁸SO₂NH—*CH(R¹)—COOH

| Example No. | R¹ | R¹⁸ | * | mp (decomp.) (° C.) | IR (ν cm⁻¹) (KBr) | Elemental analysis |
|---|---|---|---|---|---|---|
| 109 | $(CH_3)_2CH-$ | H₃C-phenyl-C≡C-phenyl- | R | 187–189 | 1720, 1656 1319, 1165 | — |

TABLE 25-continued (Ia)

$$R^{18}SO_2NH-\overset{R^1}{\underset{*}{C}}-COOH$$

| Example No. | $R^1$ | $R^{18}$ | * | mp (decomp.) (° C.) | IR (ν cm$^{-1}$) (KBr) | Elemental analysis |
|---|---|---|---|---|---|---|
| 110 | (CH$_3$)$_2$CH— | 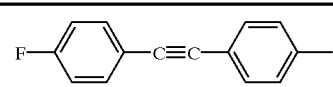 | R | 111–114 | 1724, 1635 1366, 1158 | — |
| 111 | (CH$_3$)$_3$C— | 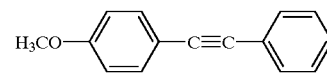 | R | 161–162 | 1711, 1683 1600, 1328 1159 | C$_{21}$H$_{23}$NO$_5$S.1.3H$_2$O Calc. C: 59.36 H: 6.07 N: 3.30 S: 7.55 Foun. C: 59.36 H: 6.06 N: 3.50 S: 7.44 |
| 112 | CH$_3$CH$_2$(CH$_3$)CH— | 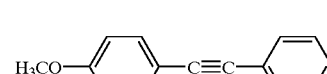 | R | 157–159 | 1732, 1680 1329, 1167 | — |
| 113 | 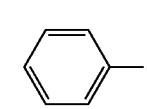 | 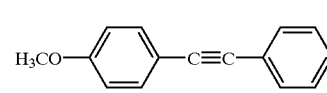 | R | 133–136 | 1735, 1651 1348, 1165 | — |
| 114 | 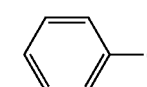 | 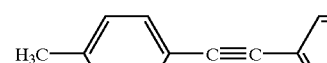 | R | 183–185 | 1727, 1604 1335, 1182 | — |
| 115 | 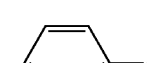 | 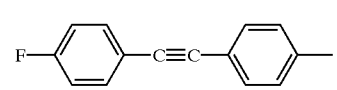 | R | 166–168 | 1725, 1663 1399, 1197 | C$_{23}$H$_{18}$FNO$_4$S.0.3H$_2$O Calc. C: 64.41 H: 4.37 F: 4.43 N: 3.27 S: 7.48 Foun. C: 64.37 H: 4.38 F: 4.96 N: 3.31 S: 7.24 |
| 116 | (CH$_3$)$_2$CH— | 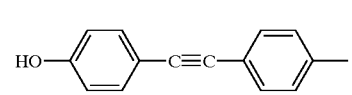 | R | 163–165 | 1728, 1332 1172 | — |

TABLE 26

(Ia)

$$R^{18}SO_2NH-\overset{R^1}{\underset{*}{C}}-COOH$$

| Example No. | $R^1$ | $R^{18}$ | * | mp (decomp.) (° C.) | IR (ν cm$^{-1}$) (KBr) | Elemental analysis |
|---|---|---|---|---|---|---|
| 117 | (CH$_3$)$_2$CH— | 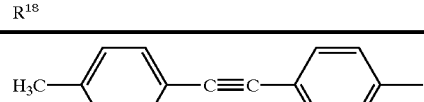 | R | 187–189 | 1720, 1656 1319, 1165 | — |
| 118 | 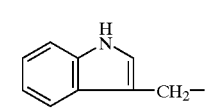 | 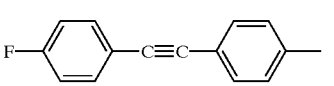 | R | 111–114 | 1724, 1635 1366, 1158 | — |
| 119 | 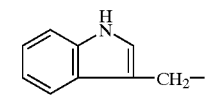 | 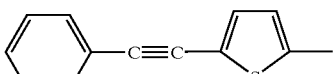 | R | 167–169 | 1585, 1318 1153 | — |

TABLE 26-continued $$R^{18}SO_2NH-\overset{R^1}{\underset{*}{C}H}-COOH \quad (Ia)$$

| Example No. | $R^1$ | $R^{18}$ | * | mp (decomp.) (° C.) | IR ($\nu$ cm$^{-1}$) (KBr) | Elemental analysis |
|---|---|---|---|---|---|---|
| 120 | 3-indolylmethyl | 2-nitrophenyl-C≡C-(5-methylthiophen-2-yl) | R | — | 1605, 1523, 1340, 1151 | — |
| 121 | 3-indolylmethyl | 4-methoxyphenyl-C≡C-(5-methylthiophen-2-yl) | R | — | 1604, 1524, 1336, 1173 | — |
| 122 | 3-indolylmethyl | 4-fluorophenyl-C≡C-(5-methylthiophen-2-yl) | R | 103–106 | 1721, 1620, 1339, 1163 | — |
| 123 | 3-indolylmethyl | 4-methylphenyl-C≡C-(5-methylthiophen-2-yl) | R | 180–182 | 1729, 1675, 1340, 1168 | — |
| 124 | $(CH_3)_2CH-$ | 4-methoxyphenyl-C≡C-(5-methylthiophen-2-yl) | R | 147–148 | 1710, 1604, 1351, 1216 | $C_{18}H_{19}NO_5S_2 \cdot 0.2H_2O$ Calc. C: 54.45 H: 4.92 N: 3.53 S: 16.15 Foun. C: 54.39 H: 4.93 N: 3.79 S: 15.96 |

TABLE 27

$$R^{18}SO_2NH-\overset{R^1}{\underset{*}{C}H}-COOH \quad (Ia)$$

| Example No. | $R^1$ | $R^{18}$ | * | mp (decomp.) (° C.) | IR ($\nu$ cm$^{-1}$) (KBr) | Elemental analysis |
|---|---|---|---|---|---|---|
| 125 | $(CH_3)_2CH-$ | 4-methylphenyl-C≡C-(5-methylthiophen-2-yl) | R | 157–158 | 1712, 1350, 1163 | $C_{18}H_{19}NO_4S_2 \cdot 0.2H_2O$ Calc. C: 56.73 H: 5.13 N: 3.68 S: 16.83 Foun. C: 57.03 H: 5.30 N: 3.89 S: 16.56 |
| 126 | $(CH_3)_2CH-$ | 4-fluorophenyl-C≡C-(5-methylthiophen-2-yl) | R | 154–158 | 1710, 1499, 1356, 1165 | — |
| 127 | benzyl | 4-methoxyphenyl-C≡C-(5-methylthiophen-2-yl) | R | 149–150 | 1695, 1334, 1184 | $C_{22}H_{19}NO_5S_2 \cdot 0.2H_2O$ Calc. C: 59.36 H: 4.39 N: 3.15 S: 14.41 Foun. C: 59.43 H: 4.61 N: 3.25 S: 14.02 |
| 128 | benzyl | 4-methylphenyl-C≡C-(5-methylthiophen-2-yl) | R | 161–164 | 1710, 1329, 1180 | — |

TABLE 27-continued
(Ia)
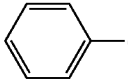
| Example No. | R[1] | R[18] | * | mp (decomp.) (° C.) | IR (ν cm[−1]) (KBr) | Elemental analysis |
|---|---|---|---|---|---|---|
| 129 | 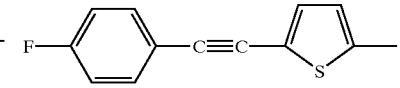 | 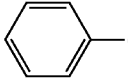 | R | 155–158 | 1734, 1699 1324, 1105 | $C_{21}H_{16}FNO_4S_2$ Calc. C: 58.73 H: 3.75 F: 4.42 N: 3.26 S: 14.93 Foun. C: 58.66 H: 3.93 F: 4.52 N: 3.33 S: 14.41 |
| 130 | 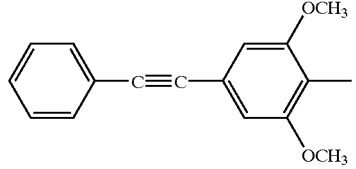 | 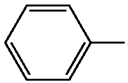 | R | — | — | — |
| 131 | 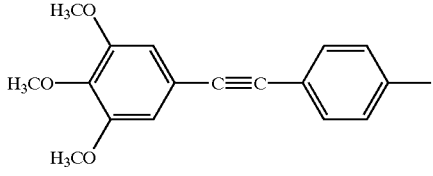 | 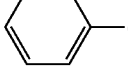 | R | — | — | — |
| 132 | 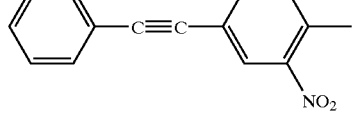 | 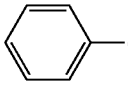 | R | — | — | — |
TABLE 28
(Ia)
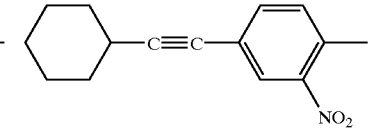
| Example No. | R[1] | R[18] | * | mp (decomp.) (° C.) | IR (ν cm[−1]) (KBr) | Elemental analysis |
|---|---|---|---|---|---|---|
| 133 | 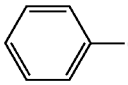 | 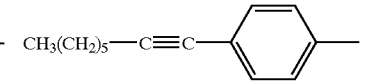 | R | — | — | — |
| 134 | 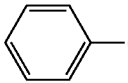 | CH₃(CH₂)₅—C≡C—⟨aryl⟩— | R | — | — | — |
| 135 | 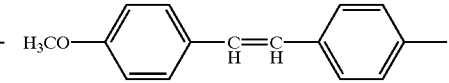 | H₃CO—⟨aryl⟩—CH=CH—⟨aryl⟩— | R | — | — | — |

TABLE 28-continued (Ia)

$$R^{18}SO_2NH-\overset{R^1}{\underset{*}{C}}H-COOH$$

| Example No. | R¹ | R¹⁸ | * | mp (decomp.) (° C.) | IR (ν cm⁻¹) (KBr) | Elemental analysis |
|---|---|---|---|---|---|---|
| 136 | phenyl-CH₂— | H₃CO-C₆H₄-CH=CH-(5-methylthiophen-2-yl) | R | — | — | — |
| 137 | phenyl-CH₂— | F-C₆H₄-C≡C-(5-methylthiophen-2-yl) | R | — | — | — |
| 138 | phenyl-CH₂— | Br-C₆H₄-C≡C-(5-methylthiophen-2-yl) | R | — | — | — |
| 139 | phenyl-CH₂— | Cl-C₆H₄-C≡C-(5-methylthiophen-2-yl) | R | — | — | — |
| 140 | phenyl-CH₂— | HO-C₆H₄-C≡C-(5-methylthiophen-2-yl) | R | — | — | — |

TABLE 29

(Ia)

$$R^{18}SO_2NH-\overset{R^1}{\underset{*}{C}}H-COOH$$

| Example No. | R¹ | R¹⁸ | * | mp (decomp.) (° C.) | IR (ν cm⁻¹) (KBr) | Elemental analysis |
|---|---|---|---|---|---|---|
| 141 | phenyl-CH₂— | cyclopropyl-C₆H₄-C≡C-(5-methylthiophen-2-yl) | R | — | — | — |
| 142 | phenyl-CH₂— | isopropyl-C₆H₄-C≡C-(5-methylthiophen-2-yl) | R | — | — | — |
| 143 | phenyl-CH₂— | F₃C-C₆H₄-C≡C-(5-methylthiophen-2-yl) | R | — | — | — |
| 144 | phenyl-CH₂— | biphenyl-C≡C-(5-methylthiophen-2-yl) | R | — | — | — |
| 145 | phenyl-CH₂— | MeOC-C₆H₄-C≡C-(5-methylthiophen-2-yl) | R | — | — | — |

TABLE 29-continued (Ia)

$$R^{18}SO_2NH-\underset{*}{\overset{R^1}{C}}-COOH$$

| Example No. | R¹ | R¹⁸ | * | mp (decomp.) (° C.) | IR (ν cm⁻¹) (KBr) | Elemental analysis |
|---|---|---|---|---|---|---|
| 146 | C₆H₅-CH₂- | 4-(5-methylthien-2-ylethynyl)-(vinyl)phenyl | R | — | — | — |
| 147 | C₆H₅-CH₂- | HOOC-C₆H₄-C≡C-(5-methylthien-2-yl) | R | — | — | — |
| 148 | C₆H₅-CH₂- | MeOOC-C₆H₄-C≡C-(5-methylthien-2-yl) | R | — | — | — |

TABLE 30

(Ia)

$$R^{18}SO_2NH-\underset{*}{\overset{R^1}{C}}-COOH$$

| Example No. | R¹ | R¹⁸ | * | mp (decomp.) (° C.) | IR (ν cm⁻¹) (KBr) | Elemental analysis |
|---|---|---|---|---|---|---|
| 149 | C₆H₅-CH₂- | H₂NOC-C₆H₄-C≡C-(5-methylthien-2-yl) | R | — | — | — |
| 150 | C₆H₅-CH₂- | OHC-C₆H₄-C≡C-(5-methylthien-2-yl) | R | — | — | — |
| 151 | C₆H₅-CH₂- | O₂N-C₆H₄-C≡C-(5-methylthien-2-yl) | R | — | — | — |
| 152 | C₆H₅-CH₂- | H₂N-C₆H₄-C≡C-(5-methylthien-2-yl) | R | — | — | — |
| 153 | C₆H₅-CH₂- | Me₂N-C₆H₄-C≡C-(5-methylthien-2-yl) | R | — | — | — |
| 154 | C₆H₅-CH₂- | MeO₂S-C₆H₄-C≡C-(5-methylthien-2-yl) | R | — | — | — |
| 155 | C₆H₅-CH₂- | HS-C₆H₄-C≡C-(5-methylthien-2-yl) | R | — | — | — |

TABLE 30-continued

(Ia)

| Example No. | R¹ | R¹⁸ | * | mp (decomp.) (° C.) | IR (ν cm⁻¹) (KBr) | Elemental analysis |
|---|---|---|---|---|---|---|
| 156 | ![phenyl-CH2] | ![NC-phenyl-C≡C-thienyl] | R | — | — | — |

EXAMPLE 157, 158

Process 1

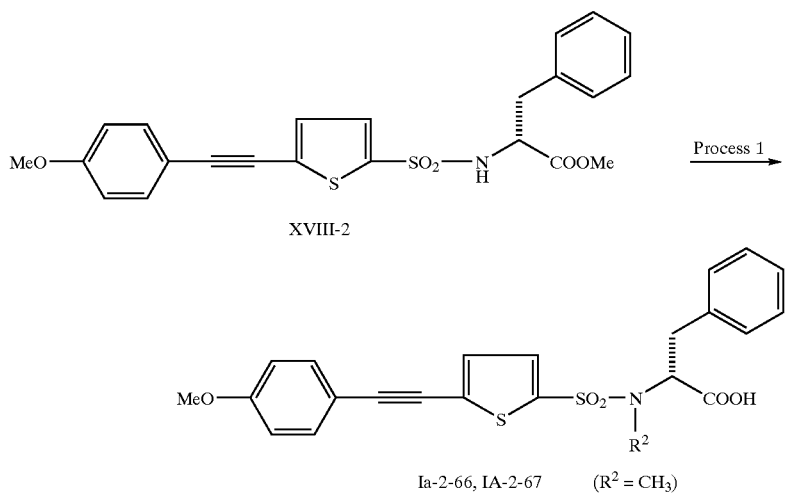

To a solution of 150 mg (0.33 mmol) of compound (XVIII-2) in 2 ml of dimethylformamide which was synthesized the same manner as those described in Example 96 was added 227 mg (5×0.33 mmol) of potassium carbonate and 0.1 ml (5×0.33 mmol) of methyl iodide, and the resulting mixture was stirred overnight at room temperature. The reaction mixture was poured into water and extracted with ethyl acetate. The organic layer was washed with water, dried over $Na_2SO_4$, and concentrated in vacuo to give 373 mg of N-methyl derivative as an oil. Yield 91%.

Elemental analysis $C_{24}H_{23}NO_5S_2$

Caldc.: C, 61.39; H, 4.94; N, 2.98; S, 13.66. Found: C, 61.22; H, 5.18; N, 2.93; S, 13.27.

Further, a solution of 140 mg of the above oily compound which was obtained the above process in 2 ml of methanol was added 0.6 ml of 1N NaOH, and the resulting mixture was stirred overnight at room temperature. The reaction mixture was acidified with 2N HCl and extracted with ethyl acetate. The organic layer was washed with water, dried over $Na_2SO_4$, and concentrated in vacuo to give 105 mg of compound (Ia-2-66) (R=Me). Yield 77%. mp. 185–186° C.

Elemental analysis $C_{23}H_{21}NO_5S$

Caldc.: C, 60.64; H, 4.65; N, 3.07; S, 14.08. Found: C, 60.56; H, 4.84; N, 3.01; S, 13.94.

IR (KBr, ν max cm⁻¹): 3600–2300br, 3426, 2203, 1710, 1604, 1503, 1344, 1151.

NMR ($d_6$-DMSO, δ ppm): 2.88(s, 3H), 2.93(dd, J=12.0, 10.2 Hz, 1H), 3.19 (dd, J=14.2, 5.6 Hz, 1H), 3.81(s, 3H), 4.74(dd, J=5.4, 10.2 Hz, 1H), 6.99–7.04(m, 2H), 7.20–7.35 (m, 7H), 7.52–7.56(m, 2H), 6.90(d, J=9.0 Hz, 2H), 7.44(d, J=9.0 Hz, 2H), 7.12(d, J=4.0 Hz, 1H), 7.44(d, J=4.0 Hz, 1H).

The compound (Ia-2-67) ($R^2$=$CH_2Ph$) was synthesized in the same manner as those described in Example 157.

IR(KBr, ν max cm⁻¹): 2200,1722,1340,1151.

NMR ($d_6$-DMSO, δ ppm): 2.94(dd, J=7.6, 13.8 Hz, 1H), 3.19(dd, J=7.2, 14.4 Hz, 1H), 3.83(s, 3H), 4.29(d, J=16.2 Hz, 1H), 4.62(d, J=16.2 Hz, 1H) (Only characteristic peaks are shown.)

EXAMPLE 159

(Method C)

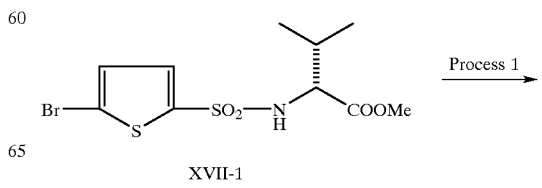

Process 1

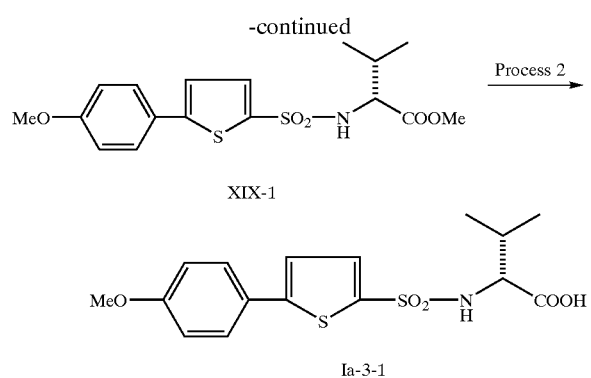

XIX-1

Ia-3-1

Process 1

To a solution of 500 mg (1.4 mmol) of compound(XVII-2) which was obtained Example 96 in 12 ml of dry tetrahydrofuran was added 387 mg (2×1.4 mmol) of powdery potassium carbonate, 319 mg (1.5×1.4 mmol) of 4-methoxyphenylboronic acid and 81 mg (0.05×1.4 mmol) of tetrakis(triphenylphosphine)palladium. The resulting mixture was stirred under argon atmosphere for 48 h at 75° C. The reaction mixture was diluted with ethyl acetate. The organic layer was washed with 1N HCl, 5% NaHCO$_3$ aq., and water, dried over Na$_2$SO$_4$, and concentrated in vacuo. The residue was column chromatographed on silica gel. The fractions eluting with n-hexane/ethyl acetate=3/1 were collected and recrystallized from n-hexane to give 447 mg of the desired compound (XIX-1). Yield 83%. mp. 122–123° C.

Elemental analysis C$_{17}$H$_{21}$NO$_5$S$_2$
Caldc.: C, 53.25; H, 5.52; N, 3.65; S, 16.72. Found: C, 53.26; H, 5.50; N, 3.69; S, 16.63.
[α]$_D$ −21.7±0.6 (c=1.000 DMSO 25° C.)
IR (KBr, ν max cm$^{-1}$): 1735,1605,1505,1350,1167,1136
NMR (CDCl$_3$, δ ppm): 0.90(d, J=7.0 Hz, 3H), 1.00(d, J=6.6 Hz, 3H), 2.10(m, 1H), 3.54(s, 3H), 3.85(s, 3H), 3.87(dd, J=5.0, 10.2 Hz, 1H), 5.20(d, J=10.2 Hz, 1H), 6.94(d, J=9.0 Hz, 2H), 7.52(d, J=9.0 Hz, 2H), 7.11(d, J=4.0 Hz, 1H), 7.49(d, J=4.0 Hz, 1H).

Process 2

To a solution of 390 mg (1.01 mmol) of compound (XIX-1) in 8 ml of tetrahydrofuran and 8 ml of methanol was added 5.1 ml of 1N NaOH, and resulting mixture was stirred at 60° C. for 6 h. The reaction mixture was concentrated in vacuo to remove an organic solvent. The resulting residue was diluted with ethyl acetate. The mixture was acidified with aqueous solution of citric acid and extracted with ethyl acetate. The organic layer was washed with brine, dried over Na$_2$SO$_4$, and concentrated in vacuo to give 373 mg of compound (Ia-3-1). Yield 100%. mp.: 174–176° C.
IR(KBr, ν max cm$^{-1}$): 1735, 1503, 1343, 1163.

EXAMPLE 160–175

The compounds which were shown in Tables 31 to 32 were synthesized in a manner similar to those described in Example 159.

TABLE 31

(Ia)

R$^{18}$SO$_2$NH–*–COOH with R$^1$

| Example No. | R$^1$ | R$^{18}$ | * | mp (decomp.) (° C.) | IR (ν cm$^{-1}$) (KBr) | Elemental Analysis |
|---|---|---|---|---|---|---|
| 160 | indol-3-yl-CH$_2$– | H$_3$CO–C$_6$H$_4$–thiophene– | R | 93–96 | 1667, 1337 1180 | — |
| 161 | indol-3-yl-CH$_2$– | H$_3$C–C$_6$H$_4$–thiophene– | R | 157–159 | 1670, 1339 1194 | — |
| 162 | indol-3-yl-CH$_2$– | F–C$_6$H$_4$–thiophene– | R | 168–171 | 1725, 1598 1371, 1185 | — |
| 163 | indol-3-yl-CH$_2$– | H$_3$CS–C$_6$H$_4$–thiophene– | R | 226–230 | 1735, 1341 1159 | C$_{22}$H$_{20}$N$_2$O$_4$S$_3$·0.4H$_2$O Calc. C: 55.07 H: 4.37 N: 5.84 S: 20.05 Foun. C: 55.35 H: 4.43 N: 6.04 S: 19.65 |
| 164 | (CH$_3$)$_2$CH– | H$_3$CO–C$_6$H$_4$–thiophene– | R | 174–178 | 1735, 1503 1343, 1163 | — |

TABLE 31-continued (Ia)
$$R^{18}SO_2NH-\underset{*}{\overset{R^1}{C}}H-COOH$$

| Example No. | $R^1$ | $R^{18}$ | * | mp (decomp.) (° C.) | IR (ν cm$^{-1}$) (KBr) | Elemental Analysis |
|---|---|---|---|---|---|---|
| 165 | $(CH_3)_2CH-$ | 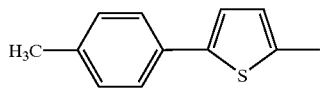 | R | 165–167 | 1713, 1353 1163 | — |
| 166 | $(CH_3)_2CH-$ | 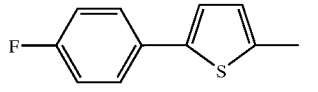 | R | 146–147 | 1702, 1504 1352, 1168 | $C_{15}H_{16}FNO_4S_2 \cdot 0.1H_2O$ Calc. C: 50.15 H: 4.55 F: 5.29 N: 3.90 S: 17.85 Foun. C: 49.99 H: 4.58 F: 5.22 N: 4.05 S: 17.77 |
| 167 | $(CH_3)_2CH-$ | 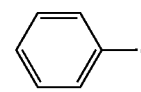 | R | 157–159 | 1747, 1324 1159 | $C_{16}H_{19}NO_4S_3$ Calc. C: 49.85 H: 4.97 N: 3.63 S: 24.95 Foun. C: 49.70 H: 5.00 N: 3.93 S: 24.96 |

TABLE 32

(Ia)
$$R^{18}SO_2NH-\underset{*}{\overset{R^1}{C}}H-COOH$$

| Example No. | $R^1$ | $R^{18}$ | * | mp (decomp.) (° C.) | IR (ν cm$^{-1}$) (KBr) | Elemental analysis |
|---|---|---|---|---|---|---|
| 168 | 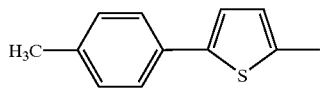 | 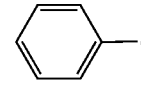 | R | 161–165 | 1735, 1698 1374 1163 | $C_{20}H_{19}NO_5S_2$ Calc. C: 57.54 H: 4.59 N: 3.35 S: 15.36 Foun. C: 57.62 H: 4.72 N: 3.52 S: 15.27 |
| 169 | 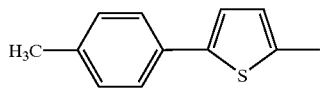 | 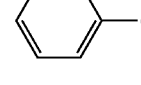 | R | 166–167 | 1713, 1609 1378, 1194 | $C_{20}H_{19}NO_4S_2$ Calc. C: 59.83 H: 4.77 N: 3.49 S: 15.97 Foun. C: 59.77 H: 4.86 N: 3.61 S: 15.86 |
| 170 | 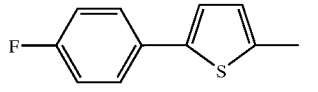 | 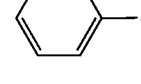 | R | 174–175 | 1721, 1654 1365, 1148 | $C_{19}H_{16}FNO_4S_2$ Calc. C: 56.28 H: 3.98 F: 4.09 N: 3.45 S: 15.82 Foun. C: 56.33 H: 4.09 F: 4.65 N: 3.65 S: 15.84 |
| 171 | 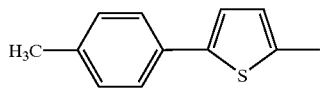 | 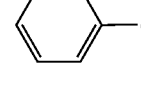 | R | 203–205 | 1750, 1730 1428, 1325 1155 | $C_{20}H_{19}NO_4S_3 \cdot 0.2H_2O$ Calc. C: 54.95 H: 4.47 N: 3.20 S: 22.00 Foun. C: 55.05 H: 4.52 N: 3.34 S: 22.04 |
| 172 | 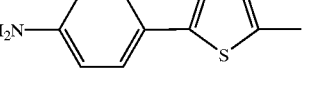 | 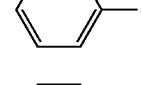 | R | — | — | — |
| 173 | 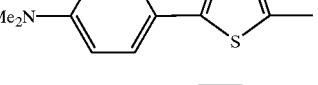 | 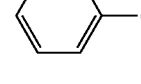 | R | — | — | — |
| 174 | 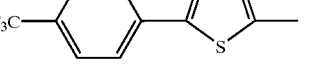 | | R | — | — | — |

TABLE 32-continued (Ia)

$$R^{18}SO_2NH-\overset{R^1}{\underset{*}{C}H}-COOH$$

| Example No. | $R^1$ | $R^{18}$ | * | mp (decomp.) (° C.) | IR (v cm$^{-1}$) (KBr) | Elemental analysis |
|---|---|---|---|---|---|---|
| 175 | —CH₂—phenyl | NC—C₆H₄—thiophene— | R | — | — | — |

EXAMPLE 176

(Method D)

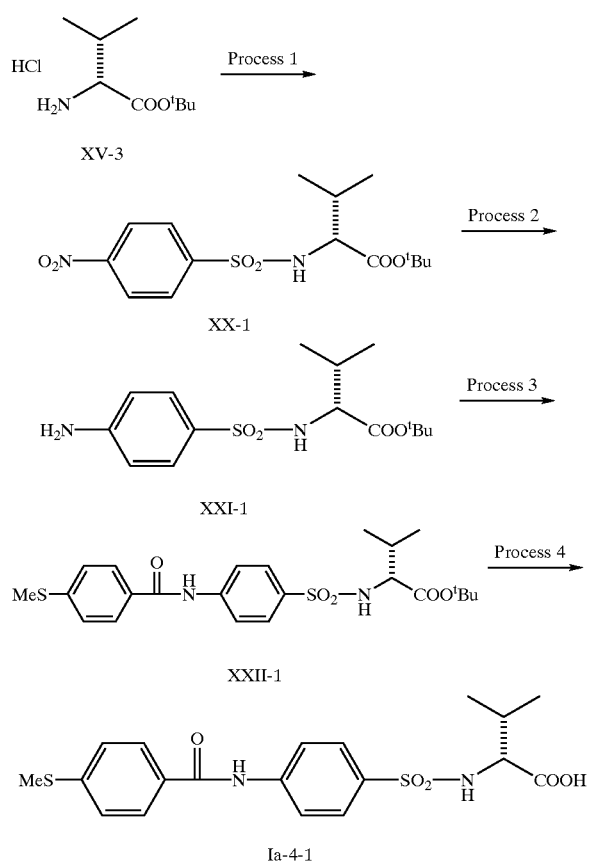

Process 1

To a solution of 10 g (47.68 mmol) of D-valine tert-butyl ester hydrochloride (XV-3) in 100 ml of dichloromethane was added 15.7 ml (3×47.68 mmol) of N-methylmorpholine and 14.1 g(1.2×47.68 mmol) of 4-nitrobenzenesulfonyl chloride under ice-cooling. After being stirred for 5 h at room temperature the reaction mixture was washed with 2N HCl, 5% NaHCO₃, water. The organic layer was dried over Na₂SO₄ and concentrated in vacuo, and the resulting residue was recrystallized from dichloromethane/n-hexane to give 13.3 g of the desired compound (XX-1). Yield 77.8%. mp. 89–90° C.

Elemental analysis $C_{15}H_{22}N_2O_6S$
Caldc.: C, 50.27; H, 6.19; N, 7.82; S, 8.95. Found: C, 50.04; H, 6.10; N, 7.89; S, 8.84.
$[\alpha]_D$ −2.9±0.8(c=0.512 DMSO 23° C.)
IR(KBr, v max cm$^{-1}$) 3430 br, 3301, 1722, 1698, 1525, 1362, 1348, 1181, 1174, 1159.

Process 2

A solution of 13.29 g (37.08 mmol) of compound (XX-1) in 200 ml of methanol was hydrogenated using 10% Pd/C (1 g) for 2 h at room temperature. The reaction mixture was filtered off and the filtrate was concentrated in vacuo. The residue was recrystallized from acetone/n-hexane to give 11.5 g of amine derivative (XXI-1). Yield 94.4%. mp. 164–166° C.

Elemental analysis $C_{15}H_{24}N_2O_4S$
Caldc.: C, 54.86; H, 7.37; N, 8.53; S, 9.76. Found: C, 54.84; H, 7.33; N, 8 63; S, 9.50.
$[\alpha]_D$ +10.3±1.0(c=0.515 DMSO 23° C.)
IR(KBr, v max cm$^{-1}$): 3461, 3375, 1716, 1638, 1598, 1344, 1313.
NMR(d-DMSO, δ ppm): 0.80(d, J=6.8 Hz, 3H), 0.82(d, J=6.6 Hz, 3H), 1.23(s, 9H), 1.83(m, 1H), 3.30(m, 1H), 5.86(s, 2H), 6.56(d, J=8.8 Hz, 2H), 7.36(d, J=8.6 Hz, 2H), 7.47(d, J=9.6 Hz, 1H)

Process 3

To a solution of 328 mg (1 mmol) of compound (XXI-1) in 10 ml of dichloromethane was added 0.33 ml (3×1 mmol) of N-methylmorpholine and 280 mg (1.5×1 mmol) of 4-(methylthio)benzoyl chloride under ice-cooling. The reaction mixture was stirred overnight at room temperature. To the reaction mixture was added ethyl ether and precipitation were collected and washed with ice-water and ethyl ether, The solid were recrystallized from acetone/ethyl ether to give 433 mg of the desired compound (XXII-1). Yield 90.5%. mp. 235–238° C.

Elemental analysis $C_{23}H_{30}N_2O_5S_2$
Caldc.: C, 57.72; H, 6.32; N, 5.85; S, 13.40. Found: C, 57.63; H, 6.28; N, 5.86; S, 13.20.
$[\alpha]_D$ +5.7±0.9(c=0.512 DMSO 25° C.)
IR(KBr, v max cm$^{-1}$): 3366, 3284, 1713, 1667, 1592, 1514, 1498, 1341, 1317.
NMR(d₆-DMSO, δ ppm): 0.82(d, J=6.6 Hz, 3H), 0.84(d, J=6.8 Hz, 3H), 1.22(s, 9H), 1.91(m, 1H), 2.55(s, 3H), 3.32(s, 3H), 3.44(dd, J=6.2, 8.6 Hz, 1H), 7.40(d, J=8.6 Hz, 2H), 7.73(d, J=8.6 Hz, 2H), 7.90–8.01(m, 5H), 10.48 (s, 1H).

Process 4

To a solution of 405 mg (0.85 mmol) of compound (XXII-1) in 3 ml of dichloromethane was added 3.3 ml (50×0.85 mmol) of trifluoroacetic acid and resulting mixture was stirred for 2 h at room temperature. The reaction mixture was concentrated in vacuo and the resulting residue was washed with ethyl ether to give 340 mg of the desired compound (Ia-4-1). Yield 94.7%. mp. 231–234° C.

IR(KBr, ν max cm$^{-1}$): 1748, 1655, 1592, 1323, 1161.

Caldc.: C, 53.14; H, 5.13; N, 6.46; S, 14.78. Found: C, 53.48; H, 5.31; N, 6.57; S, 15.06.

EXAMPLE 177–208

The compounds which were shown in Tables 33 to 36 were synthesized in a manner similar to those described in Example 176.

TABLE 33

(Ia)

$R^{18}SO_2NH-*C(R^1)-COOH$

| Example No. | R$^1$ | R$^{18}$ | * | mp (decomp.) (° C.) | IR (ν cm$^{-1}$) (KBr) | Elemental analysis |
|---|---|---|---|---|---|---|
| 177 | indol-3-ylmethyl | phenyl-C(O)NH-(4-tolyl) | R | 215–217 | 1732, 1641 1341, 1163 | — |
| 178 | indol-3-ylmethyl | 4-H$_3$CO-phenyl-C(O)NH-(4-tolyl) | R | 233–234 | 1726, 1655 1323, 1177 | C$_{25}$H$_{23}$N$_3$O$_6$S.0.9H$_2$O Calc. C: 58.91 H: 4.90 N: 8.24 S: 6.29 Foun. C: 58.97 H: 5.07 N: 7.95 S: 6.10 |
| 179 | indol-3-ylmethyl | 4-H$_2$N-phenyl-C(O)NH-(4-tolyl) | R | 216–218 | 1723, 1633 1361, 1149 | — |
| 180 | indol-3-ylmethyl | 4-O$_2$N-phenyl-C(O)NH-(4-tolyl) | R | 211–213 | 1719, 1629 1340, 1156 | C$_{24}$H$_{20}$N$_4$O$_7$S.1.1H$_2$O Calc. C: 54.56 H: 4.24 N: 10.60 S: 6.07 Foun. C: 54.51 H: 4.32 N: 10.83 S: 6.15 |
| 181 | indol-3-ylmethyl | 4-(H$_3$C)$_2$N-phenyl-C(O)NH-(4-tolyl) | R | 236–238 | 1732, 1653 1399, 1199 | C$_{26}$H$_{26}$N$_4$O$_5$S.0.9H$_2$O Calc. C: 59.73 H: 5.36 N: 10.72 S: 6.13 Foun. C: 59.58 H: 5.23 N: 10.85 S: 6.47 |
| 182 | indol-3-ylmethyl | 4-H$_3$C-phenyl-C(O)NH-(4-tolyl) | R | 240–244 | 1731, 1656 1591, 1327 1160 | C$_{25}$H$_{23}$N$_3$O$_5$S.0.9H$_2$O Calc. C: 60.82 H: 5.06 N: 8.51 S: 6.49 Foun. C: 60.83 H: 5.19 N: 8.66 S: 6.66 |
| 183 | indol-3-ylmethyl | 4-Br-phenyl-C(O)NH-(4-tolyl) | R | 215–218 | 1727, 1668 1590, 1316 1154 | C$_{24}$H$_{20}$BrN$_3$O$_5$S.0.6H$_2$O Calc. C: 52.11 H: 3.86 Br: 14.44 N: 7.60 S: 5.80 Foun. C: 52.13 H: 4.04 Br: 14.57 N: 7.43 S: 5.70 |
| 184 | indol-3-ylmethyl | 4-H$_3$CS-phenyl-C(O)NH-(4-tolyl) | R | 244–249 | 1728, 1653 1593, 1323, 1159 | C$_{25}$H$_{23}$N$_3$O$_5$S$_2$.0.7H$_2$O Calc. C: 57.50 H: 4.71 N: 8.05 S: 12.28 Foun. C: 57.63 H: 4.79 N: 8.00 S: 12.08 |

TABLE 34

(Ia)

$$R^{18}SO_2NH-\overset{R^1}{\underset{*}{C}H}-COOH$$

| Example No. | R$^1$ | R$^{18}$ | * | mp (decomp.) (° C.) | IR (ν cm$^{-1}$) (KBr) | Elemental analysis |
|---|---|---|---|---|---|---|
| 185 | indol-3-ylmethyl | 4-F-C$_6$H$_4$-C(O)NH-C$_6$H$_4$-4-CH$_3$ | R | 170–175 | 1730, 1651 1603, 1333 1161 | C$_{24}$H$_{20}$FN$_3$O$_5$S.0.6H$_2$O Calc. C: 58.55 H: 4.34 F: 3.86 N: 8.54 S: 6.51 Foun. C: 58.67 H: 4.51 F: 3.77 N: 8.42 S: 6.47 |
| 186 | benzyl | 4-CH$_3$O-C$_6$H$_3$-C(O)NH-C$_6$H$_4$-4-CH$_3$ | R | 237–239 | 1723, 1651 1591, 1322 1161 | C$_{23}$H$_{22}$N$_2$O$_6$S Calc. C: 60.78 H: 4.88 N: 6.16 S: 7.05 Foun. C: 60.50 H: 4.99 N: 6.14 S: 7.31 |
| 187 | benzyl | 4-O$_2$N-C$_6$H$_3$-C(O)NH-C$_6$H$_4$-4-CH$_3$ | R | 235–239 | 1719, 1672 1593, 1327 1159 | C$_{22}$H$_{19}$N$_3$O$_7$S Calc. C: 56.29 H: 4.08 N: 8.95 S: 6.83 Foun. C: 56.01 H: 4.09 N: 8.93 S: 6.75 |
| 188 | benzyl | C$_6$H$_5$-C(O)NH-C$_6$H$_4$-4-CH$_3$ | R | 114–115 | 1748, 1658 1592, 1325 1159 | C$_{22}$H$_{20}$N$_2$O$_5$S.0.5CF$_3$COOH Calc. C: 57.37 H: 4.29 N: 5.82 S: 6.66 Foun. C: 57.53 H: 4.45 N: 5.75 S: 7.11 |
| 189 | benzyl | 4-Br-C$_6$H$_3$-C(O)NH-C$_6$H$_4$-4-CH$_3$ | R | 242–243 | 1743, 1670 1591, 1335 1167 | C$_{22}$H$_{19}$BrN$_2$O$_5$S.CF$_3$COOH Calc. C: 46.69 H: 3.27 Br: 12.94 N: 4.54 S: 5.19 Foun. C: 46.79 H: 3.41 Br: 12.86 N: 4.57 S: 5.37 |
| 190 | benzyl | 4-CH$_3$-C$_6$H$_3$-C(O)NH-C$_6$H$_4$-4-CH$_3$ | R | 242–244 | 1752, 1726 1656, 1591 1324, 1160 | C$_{23}$H$_{22}$N$_2$O$_5$S Calc. C: 63.00 H: 5.06 N: 6.39 S: 7.31 Foun. C: 62.70 H: 5.13 N: 6.36 S: 7.36 |
| 191 | benzyl | 4-CH$_3$S-C$_6$H$_3$-C(O)NH-C$_6$H$_4$-4-CH$_3$ | R | 232–235 | 1742, 1667 1591, 1334 1161 | C$_{23}$H$_{22}$N$_2$O$_5$S$_2$.0.8CF$_3$COOH Calc. C: 52.59 H: 4.09 N: 4.99 S: 11.42 Foun. C: 52.77 H: 4.24 N: 5.12 S: 11.58 |
| 192 | benzyl | 4-F-C$_6$H$_3$-C(O)NH-C$_6$H$_4$-4-CH$_3$ | R | 218–220 | 1737, 1651 1598, 1324 1160 | C$_{22}$H$_{19}$FN$_2$O$_5$S Calc. C: 59.72 H: 4.33 F: 4.29 N: 6.33 S: 7.25 Foun. C: 59.59 H: 4.42 F: 4.30 N: 6.37 S: 7.24 |

TABLE 35

(Ia)

$$R^{18}SO_2NH-\overset{R^1}{\underset{*}{C}H}-COOH$$

| Example No. | R¹ | R¹⁸ | * | mp (decomp.) (° C.) | IR (ν cm⁻¹) (KBr) | Elemental analysis |
|---|---|---|---|---|---|---|
| 193 | phenyl-CH₂— | 6-chloropyridin-3-yl-C(O)NH-(4-methylphenyl) | R | 201–203 | 1724, 1673, 1592, 1326, 1156 | $C_{21}H_{18}ClN_3O_5S$<br>Calc. C: 54.84 H: 3.94 Cl: 7.71 N: 9.14 S: 6.97<br>Foun. C: 54.39 H: 4.06 Cl: 7.42 N: 8.98 S: 6.99 |
| 194 | phenyl-CH₂— | 2-chloro-6-methylpyridin-3-yl-C(O)NH-(4-methylphenyl) | R | 206–208 | 1725, 1682, 1592, 1332, 1160 | $C_{22}H_{20}ClN_3O_5S \cdot 0.1CF_3COOH$<br>Calc. C: 55.15 H: 4.19 Cl: 7.33 N: 8.69 S: 6.63<br>Foun. C: 55.25 H: 4.28 Cl: 7.10 N: 8.80 S: 6.80 |
| 195 | (CH₃)₂CH— | biphenyl-4-yl-C(O)NH-(4-methylphenyl) | R | 254–256 | 1748, 1659, 1590, 1324, 1161 | $C_{24}H_{24}N_2O_5S \cdot 0.5H_2O$<br>Calc. C: 62.46 H: 5.46 N: 6.07 S: 6.95<br>Foun. C: 62.42 H: 5.54 N: 6.26 S: 6.97 |
| 196 | (CH₃)₂CH— | 4-methylphenyl-C(O)NH-(4-methylphenyl) | R | 227–229 | 1749, 1658, 1592, 1323, 1161 | $C_{19}H_{22}N_2O_5S \cdot 0.2H_2O$<br>Calc. C: 57.91 H: 5.73 N: 7.11 S: 8.14<br>Foun. C: 57.94 H: 5.69 N: 7.03 S: 8.14 |
| 197 | (CH₃)₂CH— | 4-(methylthio)phenyl-C(O)NH-(4-methylphenyl) | R | 231–234 | 1748, 1655, 1592, 1323, 1161 | $C_{19}H_{22}N_2O_5S_2 \cdot 0.1CF_3COOH$<br>Calc. C: 53.14 H: 5.13 N: 6.46 S: 14.78<br>Foun. C: 53.48 H: 5.31 N: 6.57 S: 15.06 |
| 198 | (CH₃)₂CH— | 4-fluorophenyl-C(O)NH-(4-methylphenyl) | R | 235–236 | 1749, 1726, 1668, 1597, 1322, 1160 | $C_{18}H_{19}FN_2O_5S \cdot 0.1CF_3COOH$<br>Calc. C: 53.86 H: 4.74 F: 6.09 N: 6.90 S: 7.90<br>Foun. C: 53.82 H: 4.85 F: 5.60 N: 6.93 S: 7.78 |
| 199 | (CH₃)₂CH— | phenyl-C(O)NH-(4-methylphenyl) | R | 226–227 | 1728, 1661, 1591, 1317, 1159 | $C_{18}H_{20}N_2O_5S \cdot 0.1H_2O$<br>Calc. C: 57.16 H: 5.38 N: 7.41 S: 8.48<br>Foun. C: 57.01 H: 5.46 N: 7.57 S: 8.57 |
| 200 | (CH₃)₂CH— | 4-methoxyphenyl-C(O)NH-(4-methylphenyl) | R | 220–221 | 1696, 1654, 1591, 1317, 1255 | $C_{19}H_{22}N_2O_6S \cdot 0.2H_2O$<br>Calc. C: 55.65 H: 5.51 N: 6.83 S: 7.82<br>Foun. C: 55.63 H: 5.48 N: 7.03 S: 7.75 |

TABLE 36

(Ia)

$$R^{18}SO_2NH-\overset{R^1}{\underset{*}{C}H}-COOH$$

| Exam-No. | $R^1$ | $R^{18}$ | * | mp (decomp.) (° C.) | IR ($\nu$ cm$^{-1}$) (KBr) | Elemental analysis |
|---|---|---|---|---|---|---|
| 201 | $(CH_3)_2CH-$ | $O_2N$-C$_6$H$_4$-C(O)NH-C$_6$H$_4$- | R | 240–242 | 1726, 1688, 1591, 1347, 1166 | $C_{18}H_{19}N_3O_7S \cdot 0.4H_2O$<br>Calc. C: 50.44 H: 4.66 N: 9.80 S: 7.48<br>Foun. C: 50.40 H: 4.55 N: 9.90 S: 7.44 |
| 202 | $(CH_3)_2CH-$ | Br-C$_6$H$_4$-C(O)NH-C$_6$H$_4$- | R | 229–230 | 1726, 1663, 1592, 1318, 1159 | $C_{18}H_{19}BrN_2O_5S \cdot 0.2$Ethylether<br>Calc. C: 48.03 H: 4.50 Br: 17.00 N: 5.96 S: 6.82<br>Foun. C: 48.04 H: 4.61 Br: 16.83 N: 5.96 S: 6.86 |
| 203 | $(CH_3)_3C-$ | $H_3CO$-C$_6$H$_4$-C(O)NH-C$_6$H$_4$- | R | 214–216 | 1659, 1591, 1316, 1159 | $C_{20}H_{24}N_2O_6S \cdot 0.4H_2O$<br>Calc. C: 56.17 H: 5.84 N: 6.55 S: 7.50<br>Foun. C: 56.21 H: 6.02 N: 6.50 S: 7.33 |
| 204 | $C_6H_5$-$CH_2$- | 5-methylpyrazin-2-yl-C(O)NH-C$_6$H$_4$- | R | 236–237 | 1723, 1679, 1590, 1337, 1162 | $C_{21}H_{20}N_4O_5S \cdot 0.25CF_3COOH$<br>Calc. C: 55.06 H: 4.35 N: 11.95 S: 6.84<br>Foun. C: 54.80 H: 4.90 N: 12.16 S: 7.10 |
| 205 | $C_6H_5$-$CH_2$- | pyridin-4-yl-C(O)NH-C$_6$H$_4$- | R | 272–275 | 1719, 1672, 1594, 1339, 1165 | $C_{21}H_{19}N_3O_5S$<br>Calc. C: 59.28 H: 4.50 N: 9.88 S: 7.54<br>Foun. C: 58.84 H: 4.56 N: 9.71 S: 7.36 |
| 206 | $C_6H_5$-$CH_2$- | 3-methylisoxazol-5-yl-C(O)NH-C$_6$H$_4$- | R | 214–215 | 1733, 1685, 1594, 1319, 1154 | $C_{20}H_{19}N_3O_6S$<br>Calc. C: 55.94 H: 4.46 N: 9.78 S: 7.47<br>Foun. C: 55.50 H: 4.47 N: 9.74 S: 7.31 |
| 207 | $C_6H_5$-$CH_2$- | Br-C$_6$H$_4$-NHC(O)NH-C$_6$H$_4$- | R | 217–220 | 1732, 1679, 1592, 1312, 1155 | — |
| 208 | $C_6H_5$-$CH_2$- | $H_2N$-C$_6$H$_4$-C(O)NH-C$_6$H$_4$- | R | — | — | — |

EXAMPLE 209

(Method E)

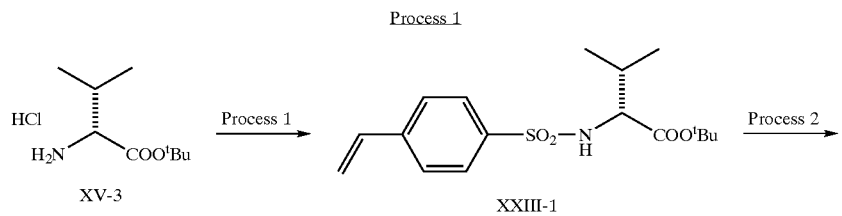

Process 1

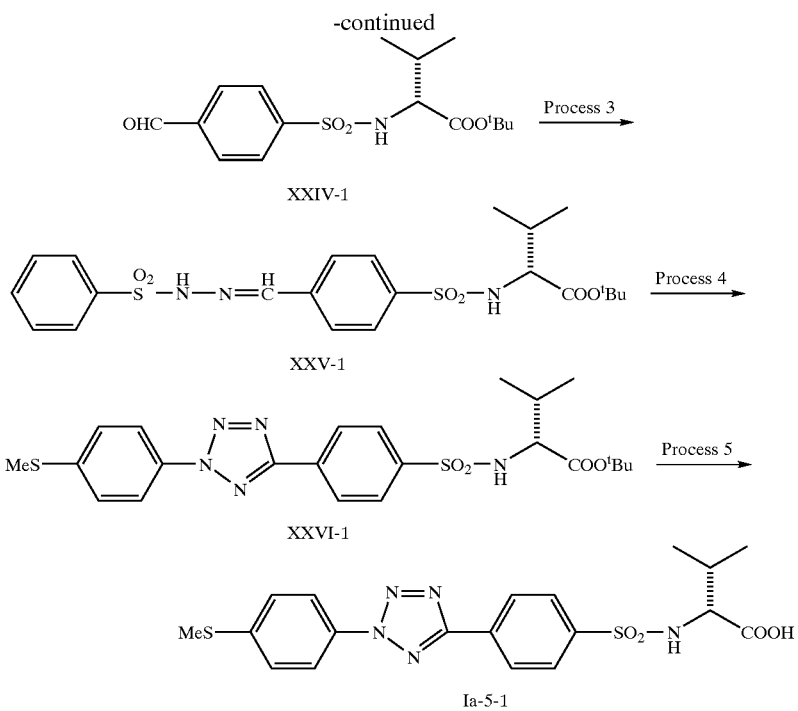

Process 1

To a solution of 20.94 g (99.8 mmol) of D-valine tert-butyl ester hydrochloride (XV-3) in 200 ml of dichloromethane was added 22 ml (2×99.8 mmol) of N-methylmorpholine and 20.27 g (99.8 mmol) of p-styrenesulfonyl chloride under ice-cooling. After being stirred for 15 h at room temperature, the reaction mixture was washed with 2N HCl, 5% NaHCO$_3$, water. The organic layer was dried over Na$_2$SO$_4$ and concentrated in vacuo, and the resulting residue was column chromatographed on silica gel. The fractions eluting with ethyl acetate/n-hexane/chloroform=1/3/1 were collected and washed with n-hexane to give 28.93 g of the desired compound (XXIII-1). Yield 85%. mp. 118–120° C.

IR(KBr, ν max cm$^{-1}$): 3419, 3283, 1716, 1348, 1168.

NMR(CDCl$_3$, δ ppm): 0.85(d, J=6.9 Hz, 3H), 1.00(d, J=6.6 Hz, 3H), 1.21(s, 9H), 2.04(m, 1H), 3.62(dd, J=9.8, 4.5 Hz, 1H), 5.09(d, J=9.8 Hz, 1H), 5.41(dd, J=0.5, 10.9 Hz, 1H), 5.84(dd, J=0.5, 17.6 Hz, 1H), 6.72(dd, J=10.9, 17.6 Hz, 1H), 7.49(d, J=8.4 Hz, 2H), 7.79(d, J=8.4 Hz, 2H).

Process 2

Ozone gas was bubbled through a solution of 5.09 g (15 mmol) of compound (XXIII-1) in 300 ml of dichloromethane for 15 h at −78° C. To this solution was added 22 ml (20×15 mmol) of methylsulfide, and the reaction mixture was allowed to warm to room temperature gradually over 80 min and concentrated in vacuo to give 6.03 g aldehyde derivative (XXIV-1).

IR(CHCl$_3$, ν max cm$^{-1}$): 3322, 1710, 1351, 1170.

NMR(CDCl$_3$, δ ppm): 0.85(d, J=6.9 Hz, 3H), 1.00(d, J=6.9 Hz, 3H), 1.22(s, 9H), 2.07(m, 1H), 3.69(dd, J=4.5, 9.9 Hz, 1H), 8.01(s, 4H), 10.08(s, 1H).

Process 3

To a solution of 6.02 g(15 mmol) of compound (XXIV-1) in 60 ml of ethanol and 15 ml of tetrahydrofuran was added 2.72 g (1.05×15 mmol) of benzenesulfonyl hydrazide at room temperature. After being stirred for 2 h, the resulting mixture was concentrated in vacuo. The residue which was obtained by concentration in vacuo was column chromatographed on silica gel and the fractions eluting with chloroform/ethyl acetate=1/4 were collected and recrystallized from ethyl acetate to give 4.44 g of the desired compound (XXV-1). Yield from process 2 60%. mp. 163–164° C.

Elemental analysis C$_{22}$H$_{29}$N$_3$O$_6$S$_2$

Caldc.: C, 53.32; H, 5.90; N, 8.48; S, 12.94. Found: C, 53.15; H, 5.87; N, 8.32; S, 12.82.

[α]$_D$ −11.6±1.0(c=0.509 DMSO 23.5° C.)

IR(KBr, ν max cm$^{-1}$): 3430, 3274, 1711, 1364, 1343, 1172.

NMR(CDCl$_3$ δ ppm): 0.84(d, J=6.9 Hz, 3H), 0.99(d, J=6.6 Hz, 3H), 1.19(s, 9H), 2.00(m, 1H), 3.63(dd, J=4.5, 9.9 Hz, 1H), 5.16(d, J=9.9 Hz, 1H), 7.50–7.68(m, 5H), 7.73(s, 1H), 7.78–7.84(m, 2H), 7.96–8.02(m, 2H), 8.16(brs, 1H).

Process 4

To a solution of 0.14 ml (1.11×1 mmol) of 4-(methylmercapto)aniline and 0.3 ml of conc. hydrochloric acid in 3 ml of aqueous 50% ethanol solution was added a solution of 78.4 mg (1.14×1 mmol) of sodium nitrite in 1 ml of water at 0 to 5° C. of the internal temperature and the reaction mixture was stirred for 15 min at the same temperature. To a solution of 496 mg (1 mmol) of compound (XXV-1) in 5 ml of dry pyridine was added the above reaction mixture over 8 min at −25° C. This reaction mixture was stirred for additional 4 h at −15° C. to rt, poured into water, and extracted with ethyl acetate. The organic layer was washed with 2N HCl, 5% NaHCO$_3$, and water, dried over Na$_2$SO$_4$, and concentrated in vacuo. The residue was column chromatographed on silica gel and the fractions eluting with chloroform/ethyl acetate=1/9 were collected to give 374 mg of the desired compound (XXVI-1). Yield 74%.

Elemental analysis C$_{23}$H$_{29}$N$_5$O$_4$S$_2$.0.3H$_2$O Found: C, 54.25; H, 5.77; N, 13.87; S, 12.52.

IR(KBr, ν max cm$^{-1}$): 3422, 3310, 1705, 1345, 1171.

NMR(d$_6$-DMSO, δ ppm): 0.83(d, J=6.9 Hz, 3H), 0.86(d, J=7.2 Hz, 3H), 1.19(s, 9H), 2.00(m, 1H), 2.59(s, 3H), 3.54(dd, J=6.3, 9.6 Hz, 1H), 7.56(d, J=8.7 Hz, 2H), 8.00(d, J=8.6 Hz, 2H), 8.10(d, J=8.7 Hz, 2H), 8.33(d, J=9.6 Hz, 2H), 8.34(d, J=8.7 Hz, 2H).

Process 5

A solution of 353 mg of compound (XXVI-1) in 2.5 ml of dichloromethane and 2.5 ml of trifluoroacetic acid was stirred for 3 h at room temperature. The reaction mixture was concentrated in vacuo and the resulting residue was washed with ethyl ether to give 308 mg of compound (Ia-5-1). Yield 98%. mp. 194–195° C.

IR(KBr, ν max cm$^{-1}$): 1720, 1343, 1166.
Elemental analysis $C_{19}H_{21}N_5O_4S_2 \cdot 1.1H_2O$ Caldc.: C, 48.83; H, 5.00; N, 14.99; S, 13.72. Found: C, 49.13; H, 5.25; N, 14.55; S, 13.34.

EXAMPLE 210–251

The compounds which were shown in Tables 37 to 43 were synthesized in a manner similar to those described in Example 209.

TABLE 37

(Ib)

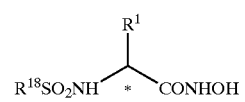

| Example No. | R$^1$ | R$^{18}$ | * | mp (decomp.) (° C.) | IR(ν cm$^{-1}$) (KBr) | $^1$H-NMR(δ ppm) d$_6$-DMSO |
|---|---|---|---|---|---|---|
| 210 |  | 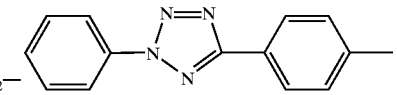 | R | — | — | — |
| 211 |  | 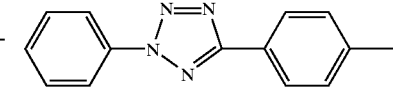 | R | 194–195 | 3700–2200 (br), 3278, 1634, 1337, 1160 | 2.65(dd, J=9.3, 13.1Hz, 1H), 2.82(dd, J=5.8, 13.1Hz, 1H), 3.86(dt, J=5.8, 9.3Hz, 1H), 7.72(A$_2$B$_2$q, J=8.1Hz, 2H), 8.19(A$_2$B$_2$q, J=8.1Hz, 2H), 8.49(d, J=9.3Hz, 1H), 8.88(s, 1H), 10.69(s, 1H) |

TABLE 38

(Ia)

| Example No. | R$^1$ | R$^{18}$ | * | mp (decomp.) (° C.) | IR(ν cm$^{-1}$) (KBr) | $^1$H-NMR(δ ppm) d$_6$-DMSO |
|---|---|---|---|---|---|---|
| 210 | 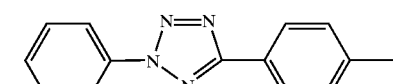 |  | R | — | — | — |
| 211 | 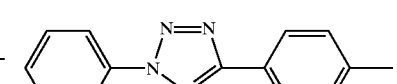 | | R | 215–216 | 2400–3700 br, 3422, 3337, 1733, 1698, 1347, 1170 | 2.75(dd, J=9.3, 13.7Hz, 1H), 2.99(dd, J=5.3, 13.7Hz, 1H), 3.96(dt, J=5.3, 9.3Hz, 1H), 8.53(d, J=9.3Hz, 1H) |

TABLE 39

(Ia)
$$R^{18}SO_2NH-\overset{R^1}{\underset{*}{CH}}-COOH$$

| Example No. | R¹ | R¹⁸ | * | mp (decomp.) (° C.) | IR (ν cm⁻¹) (KBr) | Elemental analysis |
|---|---|---|---|---|---|---|
| 212 | 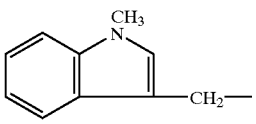 | 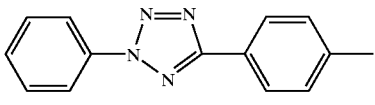 | RS | 199–202 | 1734, 1337, 1161 | $C_{25}H_{22}N_6O_4S \cdot 0.5$Ethylether<br>Calc. C: 60.10 H: 5.04 N: 15.57 S: 5.94<br>Foun. C: 60.41 H: 4.69 N: 15.52 S: 5.57 |
| 213 | 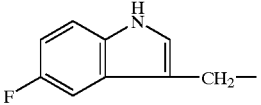 | 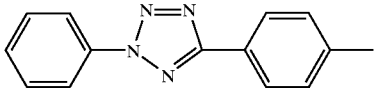 | RS | 224–225 | 1728, 1338, 1166 | $C_{24}H_{19}FN_6O_4S \cdot 0.4$Ethylether<br>Calc C: 57.35 H: 4.32 F: 3.54 N: 15.67 S: 5.98<br>Foun. C: 56.74 H: 4.37 F: 3.47 N: 15.17 S: 568 |
| 214 | $(CH_3)_2CHCH_2$— | 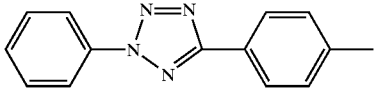 | R | 202–204 | 1720, 1595, 1338, 1170 | $C_{19}H_{21}N_5O_4S$<br>Calc. C: 54.93 H: 5.09 N: 16.86 S: 7.72<br>Foun. C: 54.75 H: 5.14 N: 16.81 S: 7.55 |
| 215 | $(CH_3)_2CH$— | 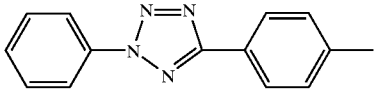 | R | 221–222 | 1696, 1594, 1349, 1173 | $C_{18}H_{19}N_5O_4S$<br>Calc. C: 53.38 H: 4.83 N: 17.29 S: 7.92<br>Foun. C: 53.38 H: 4.80 N: 17.05 S: 7.67 |
| 216 | 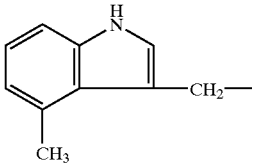 | 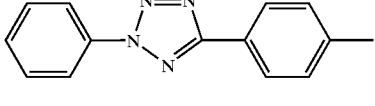 | RS | 145–148 | 1727, 1337, 1163 | — |
| 217 | 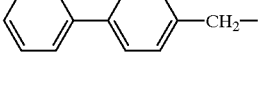 | 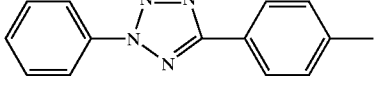 | R | 203–205 | 1735, 1495, 1336, 1160 | $C_{28}H_{23}N_5O_4S \cdot 0.6H_2O$<br>Calc. C: 62.70 H: 4.55 N: 13.06 S: 5.98<br>Foun. C: 62.61 H: 4.50 N: 13.29 S: 5.87 |
| 218 | 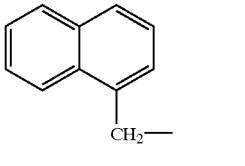 | 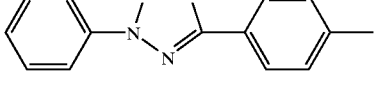 | RS | 225–227 | 1721, 1418, 1344, 1163 | $C_{26}H_{21}N_5O_4S \cdot 0.2H_2O$<br>Calc. C: 62.07 H: 4.29 N: 13.92 S: 6.37<br>Foun. C: 61.93 H: 4.30 N: 14.01 S: 6.43 |
| 219 | 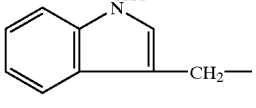 | 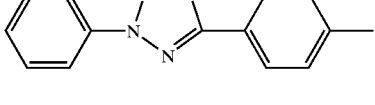 | R | 111–114 | 1727, 1703, 1459, 1332, 1165 | $C_{25}H_{20}N_6O_5S \cdot H_2O$<br>Calc. C: 56.17 H: 4.15 N: 15.72 S: 6.00<br>Foun. C: 56.20 H: 4.18 N: 15.68 S: 6.10 |

TABLE 40

(Ia)

$$R^{18}SO_2NH-*CH(R^1)-COOH$$

| Example No. | R¹ | R¹⁸ | * | mp (decomp.) (° C.) | IR (ν cm⁻¹) (KBr) | Elemental analysis |
|---|---|---|---|---|---|---|
| 220 | 1H-indol-3-yl-CH₂— | 4-(5-(4-methylphenyl)-2H-tetrazol-2-yl)-phenyl with H₃CO- on tetrazole-phenyl (4-methoxyphenyl-tetrazolyl-tolyl) | R | 195–196 | 1749, 1719, 1331, 1165 | C₂₅H₂₂N₆O₅S Calc. C: 57.91 H: 4.28 N: 16.21 S: 6.18 Foun. C: 57.77 H: 4.29 N: 16.01 S: 6.37 |
| 221 | CH₃CH₂(CH₃)CH— | 4-(2-phenyl-2H-tetrazol-5-yl)phenyl | R | 205–207 | 1730, 1693, 1349, 1173 | C₁₉H₂₁N₅O₄S Calc. C: 54.93 H: 5.09 N: 16.86 S: 7.72 Foun. C: 54.71 H: 5.09 N: 16.70 S: 7.56 |
| 222 | CH₃CH₂(CH₃)CH— | 4-(2-(4-methoxyphenyl)-2H-tetrazol-5-yl)phenyl | R | 204–207 | 1729, 1693, 1337, 1170 | C₂₀H₂₃N₅O₅S·0.4H₂O Calc. C: 53.06 H: 5.30 N: 15.47 S: 7.08 Foun. C: 53.13 H: 5.13 N: 15.12 S: 7.14 |
| 223 | (CH₃)₂CH— | 4-(2-(4-hydroxyphenyl)-2H-tetrazol-5-yl)phenyl | R | 190 decomp. | 1718, 1601 1385, 1162 | — |
| 224 | (CH₃)₂CH— | 4-(2-(4-methoxyphenyl)-2H-tetrazol-5-yl)phenyl | R | 195–197 | 1719, 1304 1162 | C₂₀H₂₃N₅O₅S·0.4H₂O Calc. C: 53.06 H: 5.30 N: 15.47 S: 7.08 Foun. C: 53.13 H: 5.13 N: 15.12 S: 7.14 |
| 225 | (CH₃)₂CH— | 4-(2-(4-bromophenyl)-2H-tetrazol-5-yl)phenyl | R | 227–228 | 1696, 1348 1171 | C₁₈H₁₈BrN₅O₄S·0.8H₂O Calc. C: 43.70 H: 3.99 Br: 16.15 N: 14.16 S: 6.48 Foun. C: 43.93 H: 3.85 Br: 15.92 N: 13.87 S: 6.47 |
| 226 | (CH₃)₃C— | 4-(2-(4-methoxyphenyl)-2H-tetrazol-5-yl)phenyl | R | 204–207 | 1698, 1344 1168 | — |
| 227 | 1H-indol-3-yl-CH₂— | 4-(2-(4-fluorophenyl)-2H-tetrazol-5-yl)phenyl | R | 203–205 | 1757, 1738 1331, 1163 | — |

TABLE 41

(Ia)

$$R^{18}SO_2NH-*CH(R^1)-COOH$$

| Example No. | R¹ | R¹⁸ | * | mp (decomp.) (° C.) | IR (ν cm⁻¹) (KBr) | Elemental analysis |
|---|---|---|---|---|---|---|
| 228 | C₆H₅—CH₂— | 4-(2-(4-bromophenyl)-2H-tetrazol-5-yl)phenyl | R | 197–199 | 1744, 1325 1154 | — |

TABLE 41-continued (Ia)

$$R^{18}SO_2NH-\overset{R^1}{\underset{*}{C}}H-COOH$$

| Example No. | $R^1$ | $R^{18}$ | * | mp (decomp.) (° C.) | IR (v cm$^{-1}$) (KBr) | Elemental analysis |
|---|---|---|---|---|---|---|
| 229 |  | 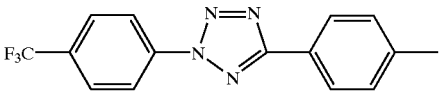 | R | 197–198 | 1738–1707 1328, 1169 | $C_{23}H_{18}F_3N_5O_4S$ Calc. C: 53.38 H: 3.51 F: 11.01 N: 13.53 S: 6.20 Foun. C: 53.11 H: 3.55 F: 10.89 N: 13.66 S: 6.31 |
| 230 |  | 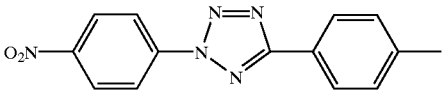 | R | 190–191 | 1730, 1597 1345, 1161 | $C_{22}H_{18}N_6O_6S \cdot 0.4H_2O$ Calc. C: 52.67 H: 3.78 N: 16.73 S: 6.39 Foun. C: 52.73 H: 3.92 N: 16.53 S: 6.55 |
| 231 |  | 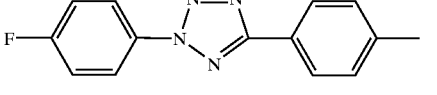 | R | 205–207 | 1730, 1509 1236, 1165 | $C_{22}H_{18}FN_5O_4S \cdot 0.2H_2O$ Calc. C: 56.09 H: 3.94 F: 4.03 N: 14.87 S: 6.81 Foun. C: 56.10 H: 4.09 F: 4.12 N: 14.84 S: 7.08 |
| 232 |  | 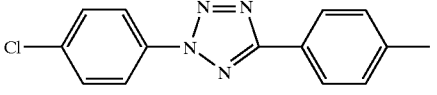 | R | 204–206 | 1730, 1493 1346, 1164 | $C_{22}H_{18}ClN_5O_4S \cdot 0.6H_2O$ Calc. C: 53.41 H: 3.91 Cl: 7.17 N: 14.16 S: 6.48 Foun. C: 53.33 H: 3.90 Cl: 7.22 N: 14.19 S: 6.68 |
| 233 |  | 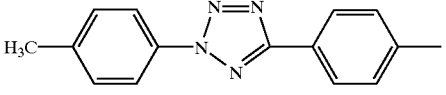 | R | 226–227 | 1732, 1697 1509, 1373 135, 1170 | $C_{23}H_{21}N_5O_4S \cdot 1.2H_2O$ Calc. C: 56.94 H: 4.86 N: 14.44 S: 6.61 Foun. C: 56.88 H: 4.49 N: 14.31 S: 6.72 |
| 234 |  | 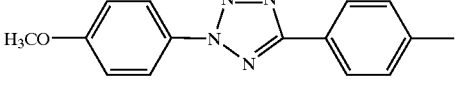 | R | 214–216 | 1732, 1697 1345, 1168 | $C_{23}H_{21}N_5O_5S \cdot 1.7H_2O$ Calc. C: 54.15 H: 4.82 N: 13.73 S: 6.29 Foun. C: 54.05 H: 4.35 N: 13.60 S: 6.77 |
| 235 |  | 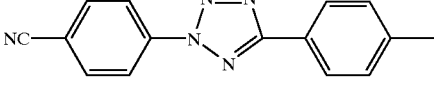 | R | 190–192 | 1731, 1605 1336, 1160 | $C_{23}H_{18}N_6O_4S \cdot 0.8H_2O$ Calc. C: 56.50 H: 4.04 N: 17.19 S: 6.56 Foun. C: 56.52 H: 4.16 N: 17.00 S: 6.52 |

TABLE 42

(Ia)

$$R^{18}SO_2NH-\overset{R^1}{\underset{*}{C}}H-COOH$$

| Example No. | $R^1$ | $R^{18}$ | * | mp (decomp.) (° C.) | IR (v cm$^{-1}$) (KBr) | Elemental anaylsis |
|---|---|---|---|---|---|---|
| 236 |  | 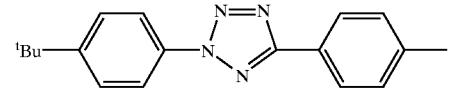 | R | 224–226 | 1738, 1328 1314, 1149 | $C_{26}H_{27}N_5O_4S$ Calc. C: 61.77 H: 5.38 N: 13.85 S: 6.34 Foun. C: 61.59 H: 5.45 N: 13.89 S: 6.27 |

TABLE 42-continued (Ia)

$$R^{18}SO_2NH-*CH(R^1)-COOH$$

| Example No. | $R^1$ | $R^{18}$ | * | mp (decomp.) (° C.) | IR (ν cm$^{-1}$) (KBr) | Elemental analysis |
|---|---|---|---|---|---|---|
| 237 | phenyl-CH$_2$– | 4-cyclohexylphenyl-(tetrazol-2-yl)-4-phenyl- | R | 225–227 | 1739, 1512, 1329, 1178 | C$_{28}$H$_{29}$N$_5$O$_4$S.0.3H$_2$O<br>Calc. C: 62.62 H: 5.56<br>N: 13.04 S: 5.97<br>Foun. C: 62.46 H: 5.52<br>N: 13.43 S: 6.28 |
| 238 | phenyl-CH$_2$– | 4-phenoxyphenyl-(tetrazol-2-yl)-4-phenyl- | R | 182–184 | 1587, 1506, 1242, 1159 | — |
| 239 | phenyl-CH$_2$– | 4-hydroxyphenyl-(tetrazol-2-yl)-4-phenyl- | R | 226–228 | 1713, 1514, 1341, 1159 | — |
| 240 | (1H-indol-3-yl)-CH$_2$– | 4-bromophenyl-(tetrazol-2-yl)-4-phenyl- | R | 205–207 | 1744, 1716, 1490, 1327, 1159 | C$_{24}$H$_{19}$BrN$_6$O$_4$S.1.7H$_2$O<br>Calc. C: 48.20 H: 3.78<br>Br: 13.36 N: 14.05<br>S: 5.36<br>Foun. C: 48.27 H: 3.75<br>Br: 13.16 N: 14.11<br>S: 5.38 |
| 241 | (1H-indol-3-yl)-CH$_2$– | 4-methylphenyl-(tetrazol-2-yl)-4-phenyl- | R | 199–201 | 1718, 1685, 1334, 1170 | C$_{25}$H$_{22}$N$_6$O$_4$S.0.6H$_2$O<br>Calc. C: 58.49 H: 4.56<br>N: 16.37 S: 6.25<br>Foun. C: 58.52 H: 4.69<br>N: 16.71 S: 5.90 |
| 242 | (CH$_3$)$_2$CH– | 4-methylphenyl-(tetrazol-2-yl)-4-phenyl- | R | 206–207 | 1716, 1346, 1165 | C$_{19}$H$_{21}$N$_5$O$_4$S.0.8H$_2$O<br>Calc. C: 53.09 H: 5.30<br>N: 16.29 S: 7.46<br>Foun. C: 53.20 H: 5.14<br>N: 16.06 S: 7.70 |
| 243 | (CH$_3$)$_2$CH– | 4-fluorophenyl-(tetrazol-2-yl)-4-phenyl- | R | 208–209 | 1746, 1726, 1715, 1334, 1159 | C$_{18}$H$_{18}$FN$_5$O$_4$S.0.2H$_2$O<br>Calc. C: 51.11 H: 4.38<br>F: 4.49 N: 16.55 S: 7.58<br>Foun. C: 50.90 H: 4.37<br>F: 4.89 N: 16.28<br>S: 7.46 |

TABLE 43

(Ia)

$$R^{18}SO_2NH-*CH(R^1)-COOH$$

| Example No. | $R^1$ | $R^{18}$ | * | mp (decomp.) (° C.) | IR (ν cm$^{-1}$) (KBr) | Elemental analysis |
|---|---|---|---|---|---|---|
| 244 | (CH$_3$)$_2$CH– | 4-chlorophenyl-(tetrazol-2-yl)-4-phenyl- | R | 223–225 | 1696, 1348, 1171 | — |
| 245 | (CH$_3$)$_2$CH– | 4-(methylthio)phenyl-(tetrazol-2-yl)-4-phenyl- | R | 194–195 | 1720, 1343, 1166 | C$_{19}$H$_{21}$N$_5$O$_4$S$_2$.1.1H$_2$O<br>Calc. C: 48.83 H: 5.00<br>N: 14.99 S: 13.72<br>Foun. C: 49.13 H: 5.25<br>N: 14.55 S: 13.34 |

TABLE 43-continued (Ia)

R¹⁸SO₂NH—*CH(R¹)—COOH

| Example No. | R¹ | R¹⁸ | * | mp (decomp.) (° C.) | IR (ν cm⁻¹) (KBr) | Elemental analysis |
|---|---|---|---|---|---|---|
| 246 | PhCH₂— | H₃CS-C₆H₄-(tetrazolyl)-C₆H₄- | R | 222–224 | 1753, 1497, 1325, 1165 | $C_{23}H_{21}N_5O_4S_2 \cdot 0.2H_2O$<br>Calc. C: 55.34 H: 4.32 N: 14.03 S: 12.85<br>Foun. C: 55.37 H: 4.35 N: 14.00 S: 12.86 |
| 247 | (1H-indol-3-yl)CH₂— | H₃CS-C₆H₄-(tetrazolyl)-C₆H₄- | R | 213–216 | 1718, 1677, 1495, 1333, 1170 | $C_{25}H_{22}N_6O_4S_2 \cdot 1.1H_2O$<br>Calc. C: 54.16 H: 4.40 N: 15.16 S: 11.57<br>Foun. C: 54.20 H: 4.66 N: 15.09 S: 11.62 |
| 248 | (1H-indol-3-yl)CH₂— | HN-tetrazolyl-C₆H₄- | R | >220 | 1698, 1430, 1327, 1163 | $C_{18}H_{16}N_6O_4S \cdot 0.4H_2O$<br>Calc. C: 51.52 H: 4.04 N: 20.03 S: 7.64<br>Foun. C: 51.34 H: 3.96 N: 19.76 S: 8.02 |
| 249 | PhCH₂— | H₂N-C₆H₄-(tetrazolyl)-C₆H₄- | R | — | — | — |
| 250 | PhCH₂— | HS-C₆H₄-(tetrazolyl)-C₆H₄- | — | — | — | — |
| 251 | PhCH₂— | OHC-C₆H₄-(tetrazolyl)-C₆H₄- | R | — | — | — |

EXAMPLE 252–266

The compounds which were shown in Tables 44 to 45 were synthesized in a manner similar to those described in Example 157.

TABLE 44

(I)

R¹⁸SO₂N(R¹⁹)—*CH(R¹)—R²⁰

| Example No. | R¹ | R¹⁸ | R¹⁹ |
|---|---|---|---|
| 252 | (CH₃)₂CH— | Ph-O-C₆H₄- | —CH₃ |
| 253 | (CH₃)₂CH— | Ph-O-C₆H₄- | —CH₃ |

TABLE 44-continued

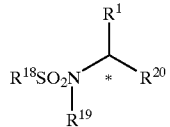

| No. | R¹⁸ | R¹⁹ | | R²⁰ |
|---|---|---|---|---|
| 254 | (CH₃)₂CH— | 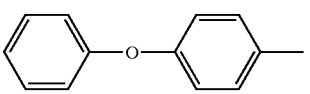 | | 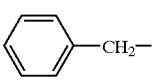 |
| 255 | (CH₃)₂CH— | 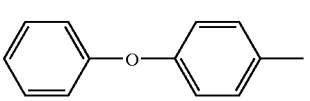 | | —(CH₂)₄NH₂ |
| 256 | (CH₃)₂CH— | 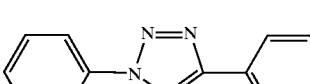 | | —CH₃ |
| 257 | (CH₃)₂CHCH₂— | 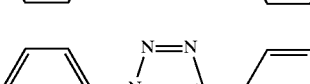 | | —CH₃ |
| 258 | 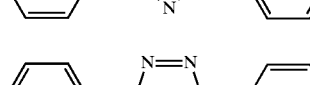 | 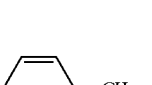 | | 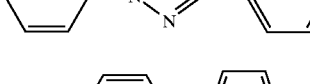 |
| 259 | (CH₃)₂CH— | 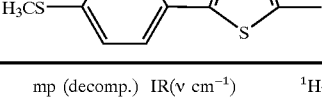 | | —CH₃ |

| Example No. | R²⁰ | * | mp (decomp.) (° C.) | IR(ν cm⁻¹) (KBr) | ¹H-NMR(δ ppm) d₆-DMSO |
|---|---|---|---|---|---|
| 252 | —COOH | R | — | 1715, 1583 1340, 1151 | 0.96(d, J=6.6Hz, 3H) 1.01(d, 6.8Hz, 3H) 2.87(s, 3H) 4.17(d, J=10.4Hz, 1H) |
| 253 | —CONHOH | R | 110–111 | 3323, 1678 1328, 1150 | 0.71(d, J=6.6Hz, 3H) 0.88(d, 6.4Hz, 3H) 2.88(s, 3H) 3.48(d, J=10.8Hz, 1H) |
| 254 | —CONHOH | R | 148–150 | 3344, 1684 1323, 1149 | 0.55(d, J=6.8Hz, 3H) 0.82(d, 6.6Hz, 3H) 3.74(s, 3H) |
| 255 | —COOH | R | — | 3700–2200 br 1681, 1319 1212 | 0.91(d, J=5.6Hz, 6H) 1.52–1.69(m, 4H) 3.84(d, J=10.4Hz, 1H) |
| 256 | —COOH | R | 206–207 | 3300–2400 br 1711, 1336 1185 | 0.95(d, J=6.6Hz, 3H) 0.97(d, 6.8Hz, 3H) 2.89(s, 3H) 4.20(d, J=10.6Hz, 1H) |
| 257 | —COOH | R | 132–132.5 | 3300–2400 br 1719, 1340 1153 | 0.92(d, J=6.6Hz, 3H) 0.97(d, 6.6Hz, 3H) 2.84(s, 3H) 4.73(t, J=7.4Hz, 1H) |
| 258 | —COOH | R | — | 3640–2400 br 1736, 1717 1694, 1346 1162 | 2.78(d.d, J=13.8, 7.2Hz, 1H) 3.14(d.d, J=14.8, 7.4Hz, 1H) 4.43(d, J=16.4Hz, 1H) 4.68(d, J=16.4Hz, 1H) |
| 259 | —COOH | R | 141–144 | 3284 br, 1745 1714, 1323 1131 | 0.96(d, J=6.4Hz, 3H) 0.97(d, J=6.4Hz, 3H) 2.52(s, 3H), 2.93(s, 3H) |

TABLE 45

(I)

$$R^{18}SO_2N(R^{19})-C^*(R^1)(R^{20})$$

| Example No. | R¹ | R¹⁸ | R¹⁹ |
|---|---|---|---|
| 260 | (CH₃)₂CH— | H₃CS-C₆H₄-(2-thienyl-5-)— | C₆H₅-CH₂— |
| 261 | C₆H₅-CH₂— | H₃CS-C₆H₄-C(O)NH-C₆H₄-(4-)— | —CH₃ |
| 262 | C₆H₅-CH₂— | H₃CS-C₆H₄-C(O)NH-C₆H₄-(4-)— | C₆H₅-CH₂— |
| 263 | C₆H₅-CH₂— | H₃CO-C₆H₄-C≡C-(2-thienyl-5-)— | —(CH₂)₄NH₂ |
| 264 | C₆H₅-CH₂— | H₃CO-C₆H₄-C≡C-C₆H₄-(4-)— | —CH₃ |
| 265 | C₆H₅-CH₂— | H₃CO-C₆H₄-C≡C-C₆H₄-C₆H₄-(4-)— | C₆H₅-CH₂— |
| 266 | C₆H₅-CH₂— | H₃CO-C₆H₄-C≡C-C₆H₄-(4-)— | —(CH₂)₄NH₂ |

| Example No. | R²⁰ | * | mp (decomp.) (° C.) | IR(ν cm⁻¹) (KBr) | ¹H-NMR(δ ppm) d₆-DMSO |
|---|---|---|---|---|---|
| 260 | —COOH | R | — | 3600–2400 br 1718, 1344 1151 | 0.72(d, J=6.4Hz, 3H) 0.85(d, J=6.4Hz, 3H) 2.47(s, 3), 4.15(d, J=10.2Hz, 1H), 4.51(d, J=15.5 Hz, 1H) 4.73(d, J=15.5Hz, 1H) |
| 261 | —COOH | R | — | 3600–2400 br 1719, 1655 1592, 1320 1154 | 2.54(s, 3H), 2.78(s, 3H) 2.85(d.d, J=14.0, 9.4Hz, 1H) 3.16(d.d, J=14.0, 6.0Hz, 1H) 4.76(d.d, J=10.0, 5.8Hz, 1H) |
| 262 | —COOH | R | — | — | — |
| 263 | —COOH | R | — | — | — |
| 264 | —COOH | R | — | — | — |
| 265 | —COOH | R | — | — | — |
| 266 | —COOH | R | — | — | — |

EXAMPLE 267

The compounds which were shown in Tables 46 were synthesized in a manner similar to those described in Example 92.

TABLE 46

(I)

$$R^{18}SO_2HN-\underset{*}{\overset{R^1}{C}}-R^{20}$$

| Example No. | R$^1$ | R$^{18}$ | R$^{20}$ | * | mp (decomp.) (° C.) | IR(ν cm$^{-1}$) (KBr) | $^1$H-NMR(δ ppm d$_6$-DMSO) |
|---|---|---|---|---|---|---|---|
| 267 | Ph-CH$_2$— | Ph—C≡C—C$_6$H$_4$— | —CONHOH | R | 156–158 | 3700–2400 br, 3267, 2217, 1671, 1321, 1161 | 2.62(dd, J=8.4, 13.5Hz, 1H), 2.80(dd, J=6.0, 13.5Hz, 1H), 3.82(ddd, J=6.0, 8.4, 8.7Hz, 1H), 8.38(d, J=8.7Hz, 1H) |
| 267 | Ph-CH$_2$— | Ph—C≡C—C$_6$H$_4$— | —COOH | R | 176–178 | 2200–3700 br, 3430, 3292, 1728, 1324, 1162 | 2.73(dd, J=9.3, 13.6Hz, 1H), 2.96(dd, J=5.4, 13.5Hz, 1H), 3.92(dt, J=5.4, 9.3Hz, 1H), 8.42(d, J=9.3Hz, 1H) |

Test examples on the compounds of the present invention are described below. The test compounds are the ones described in the Examples and Tables.

Test Example
(1) Isolation and Purification of MMP-9 (92 kDa, Gelatinase B)

Type IV collagenase (MMP-9) was purified according to the methods descrived in the following literature. Scott M. Wilhelm et al., J. Biol. Chem., 264, 17213–17221, (1989), SV40-transformed Human Lung Fibroblasts Secrete a 92-kDa Type IV Collagenase Which Is Identical to That Secreted by Normal Human Macrophages; Yasunori Okada et al., J. Biol. Chem., 267, 21712–21719, (1992), Matrix Metalloproteinase 9 (92-kDa Gelatinase/Type IV Collagenase) from HT 1080 Human Fibrosarcoma Cells; Robin V. Ward et al., Biochem. J., (1991) 278, 179–187, The purification of tissue inhibitor of metalloproteinase-2 from its 72 kDa progelatinase complex.

MMP-9 is secreted from human fibrosarcoma cell line ATCC HT 1080, into its culture medium when it is stimulated with 12-tetradecanoylphorbol-13-acetate (TPA). The production of MMP-9 in this culture was verified by the gelatin zymography as described in the following literature (Hidekazu Tanaka et al., (1993) Biochem. Biophys. Res. Commun., 190, 732–740, Molecular cloning and manifestation of mouse 105-kDa gelatinase cDNA). The condition medium of the stimulated HT 1080 was concentrated and was purified with gelatin-Sepharose 4B, concanavalin A-sepharose, and Sephacryl S-200. The purified pro-MMP-9 (92 kDa, gelatinase B) thus obtained gave a single positive band in the gelatin zymography. Subsequently, activated MMP-9 was obtained by treating the pro-MMP-9 with trypsin.

(2) Assay Methods of Type IV Collagenase Inhibitors

Collagenase assay was performed using the activated MMP-9 described above and the substrate supplied in the type IV collagenase activity kit (YAGAI, inc.), according to the manufacturer's protocol. The following 4 assays are performed per compound (inhibitor).

(A) substrate (type IV collagenase), enzyme (MP-9), inhibitor
(B) substrate (type IV collagenase), inhibitor
(C) substrate (type IV collagenase), enzyme (MMP-9)
(D) substrate (type IV collagenase)

According to the manufacturer's protocol, fluorescent intensity was measured and percent inhibition was determined by the following equation.

Inhibition (%)={1−(A−B)/(C−D)}×100

IC$_{50}$ is a concentration at which the percent inhibition reaches 50%. The results are shown in Tables 47 to 54.

TABLE 47

| Example No. | Compound No. | IC$_{50}$ (μM) | Compound No. | IC$_{50}$ (μM) |
|---|---|---|---|---|
| 1 | 1a-1-1 | 0.24 | 1b-1-1 | 0.030 |
| 2 | 1a-1-2 | 2.6 | 1b-1-2 | 0.04 |
| 3 | 1a-1-3 | 0.18 | 1b-1-3 | 0.005 |
| 4 | 1a-1-4 | 2.25 | | |
| 5 | 1a-1-5 | 0.81 | 1b-1-5 | 0.041 |
| 6 | 1a-1-6 | 0.68 | 1b-1-6 | 0.034 |
| 7 | | | 1b-1-7 | 0.028 |
| 8 | 1a-1-8 | 2.0 | 1b-1-8 | 2.0 |
| 9 | | | 1b-1-9 | 0.41 |
| 10 | | | 1b-1-10 | 2.1 |
| 11 | | | 1b-1-11 | 1.7 |
| 12 | | | 1b-1-12 | 0.085 |
| 13 | | | 1b-1-13 | 0.38 |
| 14 | 1a-1-14 | 3.7 | 1b-1-14 | 0.11 |
| 15 | | | 1b-1-15 | 0.027 |
| 16 | 1a-1-16 | 0.520 | 1b-1-16 | 0.0108 |
| 17 | 1a-1-17 | 0.205 | 1b-1-17 | 0.0203 |
| 18 | 1a-1-18 | 0.500 | 1b-1-18 | 0.0282 |
| 20 | | | 1b-1-20 | 0.134 |
| 21 | 1a-1-21 | 4.65 | 1b-1-21 | 0.0041 |
| 23 | | | 1b-1-23 | 0.073 |
| 24 | | | 1b-1-24 | 0.2 |
| 26 | | | 1b-1-26 | 1.3 |
| 27 | | | 1b-1-27 | 3.0 |

TABLE 47-continued

| Example No. | Compound No. | IC$_{50}$ ($\mu$M) | Compound No. | IC$_{50}$ ($\mu$M) |
| --- | --- | --- | --- | --- |
| 30 | 1a-1-30 | 1.16 | 1b-1-30 | 0.213 |
| 31 |  |  | 1b-1-31 | 0.0129 |

TABLE 48

| Example No. | Compound No. | IC$_{50}$ ($\mu$M) | Compound No. | IC$_{50}$ ($\mu$M) |
| --- | --- | --- | --- | --- |
| 33 | 1a-1-33 | 0.24 | 1b-1-33 | 0.005 |
| 35 | 1a-1-35 | 2.6 | 1b-1-35 | 0.0216 |
| 38 | 1a-1-38 | 0.018 |  |  |
| 40 | 1a-1-40 | 0.076 |  |  |
| 41 | 1a-1-41 | 0.312 |  |  |
| 42 | 1a-1-42 | 0.0123 |  |  |
| 43 | 1a-1-43 | 0.625 |  |  |
| 45 | 1a-1-45 | 0.040 |  |  |
| 46 | 1a-1-46 | 1.12 |  |  |
| 47 | 1a-1-47 | 0.389 |  |  |
| 48 | 1a-1-48 | 1.15 |  |  |
| 49 | 1a-1-49 | 0.249 |  |  |
| 50 | 1a-1-50 | 0.553 |  |  |
| 51 | 1a-1-51 | 0.110 |  |  |
| 52 | 1a-1-52 | 0.329 |  |  |
| 53 | 1a-1-53 | 1.8 |  |  |
| 54 | 1a-1-54 | 0.075 |  |  |
| 55 | 1a-1-55 | 0.0398 |  |  |
| 60 | 1a-1-60 | 1.31 | 1b-1-60 | 0.0012 |
| 61 | 1a-1-61 | 0.247 | 1b-1-61 | 0.247 |
| 62 |  |  | 1b-1-62 | 3.50 |
| 63 | 1a-1-63 | 1.05 | 1b-1-63 | 0.00039 |
| 64 | 1a-1-64 | 1.90 | 1b-1-64 | 0.0037 |
| 65 | 1a-1-65 | 0.291 | 1b-1-65 | 0.0035 |

TABLE 49

| Example No. | Compound No. | IC$_{50}$ ($\mu$M) | Compound No. | IC$_{50}$ ($\mu$M) |
| --- | --- | --- | --- | --- |
| 67 | 1a-1-67 |  | 1b-1-67 | 0.0061 |
| 68 | 1a-1-68 | 0.231 |  |  |
| 80 | 1a-1-80 | 1.91 |  |  |
| 83 | 1a-1-83 | 1.77 |  |  |
| 85 | 1a-1-85 | 1.2 | 1b-1-85 | 0.013 |
| 86 | 1a-1-86 | 0.35 | 1b-1-86 | 0.0053 |
| 87 |  |  | 1b-1-87 | 0.940 |
| 93 | 1a-2-2 | 0.237 |  |  |
| 94 | 1a-2-3 | 0.0109 |  |  |
| 95 | 1a-2-4 | 0.0759 |  |  |
| 96 | 1a-2-5 | 0.123 |  |  |
| 97 | 1a-2-6 | 0.088 |  |  |
| 98 | 1a-2-7 | 0.0699 |  |  |
| 100 | 1a-2-9 | 0.0577 |  |  |
| 101 | 1a-2-10 | 0.023 |  |  |
| 102 | 1a-2-11 | 0.0475 |  |  |
| 103 | 1a-2-12 | 0.0981 |  |  |
| 104 | 1a-2-13 | 3.28 |  |  |
| 105 | 1a-2-14 | 2.98 |  |  |
| 106 | 1a-2-15 | 0.133 |  |  |
| 107 | 1a-2-16 | 0.325 |  |  |
| 109 | 1a-2-18 | 1.19 |  |  |
| 110 | 1a-2-19 | 0.203 |  |  |
| 111 | 1a-2-20 | 3.41 |  |  |
| 112 | 1a-2-21 | 3.74 |  |  |
| 114 | 1a-2-23 | 0.929 |  |  |

TABLE 50

| Example No. | Compound No. | IC$_{50}$ ($\mu$M) |
| --- | --- | --- |
| 115 | 1a-2-24 | 0.161 |
| 117 | 1a-2-26 | 1.19 |
| 118 | 1a-2-27 | 0.088 |
| 119 | 1a-2-28 | 1.11 |
| 120 | 1a-2-29 | 1.53 |
| 121 | 1a-2-30 | 0.0736 |
| 122 | 1a-2-31 | 0.224 |
| 123 | 1a-2-32 | 0.0234 |
| 124 | 1a-2-33 | 0.0218 |
| 125 | 1a-2-34 | 0.0144 |
| 126 | 1a-2-35 | 0.156 |
| 127 | 1a-2-36 | 0.0243 |
| 128 | 1a-2-37 | 0.0922 |
| 129 | 1a-2-38 | 0.222 |
| 160 | 1a-3-2 | 0.040 |
| 161 | 1a-3-3 | 0.0108 |
| 162 | 1a-3-4 | 0.873 |
| 163 | 1a-3-5 | 0.0126 |
| 164 | 1a-3-6 | 0.0965 |
| 165 | 1a-3-7 | 0.230 |
| 166 | 1a-3-8 | 1.28 |
| 167 | 1a-3-9 | 0.014 |
| 168 | 1a-3-10 | 0.0083 |
| 169 | 1a-3-11 | 0.244 |
| 170 | 1a-3-12 | 2.03 |
| 171 | 1a-3-13 | 0.0395 |

TABLE 51

| Example No. | Compound No. | IC$_{50}$ ($\mu$M) |
| --- | --- | --- |
| 177 | 1a-4-2 | 0.684 |
| 178 | 1a-4-3 | 0.0252 |
| 179 | 1a-4-4 | 2.36 |
| 180 | 1a-4-5 | 0.045 |
| 181 | 1a-4-6 | 0.0539 |
| 182 | 1a-4-7 | 0.0059 |
| 183 | 1a-4-8 | 0.0027 |
| 184 | 1a-4-9 | 0.00325 |
| 185 | 1a-4-10 | 0.0422 |
| 186 | 1a-4-11 | 0.0982 |
| 187 | 1a-4-12 | 0.177 |
| 188 | 1a-4-13 | 0.843 |
| 189 | 1a-4-14 | 0.0375 |
| 190 | 1a-4-15 | 0.0597 |
| 191 | 1a-4-16 | 0.0095 |
| 192 | 1a-4-17 | 0.324 |
| 193 | 1a-4-18 | 0.722 |
| 195 | 1a-4-20 | 1.1 |
| 196 | 1a-4-21 | 0.0573 |
| 197 | 1a-4-22 | 0.0161 |
| 198 | 1a-4-23 | 0.493 |
| 199 | 1a-4-24 | 2.06 |
| 200 | 1a-4-25 | 0.173 |
| 201 | 1a-4-26 | 0.252 |
| 202 | 1a-4-27 | 0.0114 |
| 203 | 1a-4-28 | 0.173 |

TABLE 52

| Example No. | Compound No. | IC$_{50}$ ($\mu$M) | Compound No. | IC$_{50}$ ($\mu$M) |
| --- | --- | --- | --- | --- |
| 204 | 1a-4-29 | 3.95 |  |  |
| 207 | 1a-4-30 | 4.44 |  |  |
| 210 | 1a-5-2 | 0.024 |  |  |
| 211 | 1a-5-3 | 0.210 | 1b-211 | 0.00565 |
| 212 | 1a-5-4 | 0.393 |  |  |
| 213 | 1a-5-5 | 0.128 |  |  |
| 214 | 1a-5-6 | 0.832 |  |  |
| 215 | 1a-5-7 | 0.110 |  |  |
| 216 | 1a-5-8 | 0.107 |  |  |
| 218 | 1a-5-10 | 0.744 |  |  |
| 219 | 1a-5-11 | 0.574 |  |  |
| 220 | 1a-5-12 | 0.0167 |  |  |
| 221 | 1a-5-13 | 0.316 |  |  |

TABLE 52-continued

| Example No. | Compound No. | IC$_{50}$ ($\mu$M) | Compound No. | IC$_{50}$ ($\mu$M) |
|---|---|---|---|---|
| 222 | 1a-5-14 | 0.078 | | |
| 223 | 1a-5-15 | 0.349 | | |
| 224 | 1a-1-16 | 0.0101 | | |
| 225 | 1a-5-17 | 0.0122 | | |
| 226 | 1a-5-18 | 0.166 | | |
| 227 | 1a-5-19 | 0.0198 | | |
| 228 | 1a-5-20 | 0.106 | | |
| 229 | 1a-5-21 | 0.215 | | |
| 230 | 1a-5-22 | 0.281 | | |
| 231 | 1a-5-23 | 0.197 | | |
| 232 | 1a-5-24 | 0.144 | | |
| 233 | 1a-5-25 | 0.0864 | | |
| 234 | 1a-5-26 | 0.153 | | |

TABLE 53

| Example No. | Compound No. | IC$_{50}$ ($\mu$M) | Compound No. | IC$_{50}$ ($\mu$M) |
|---|---|---|---|---|
| 235 | 1a-5-27 | 0.265 | | |
| 236 | 1a-5-28 | 0.304 | | |
| 237 | 1a-5-29 | 1.32 | | |
| 238 | 1a-5-30 | 2.85 | | |
| 239 | 1a-5-31 | 0.243 | | |
| 240 | 1a-5-32 | 0.0041 | | |
| 241 | 1a-5-33 | 0.0131 | | |
| 242 | 1a-5-34 | 0.0239 | | |
| 243 | 1a-5-35 | 0.0529 | | |
| 244 | 1a-5-36 | 0.0165 | | |
| 245 | 1a-5-37 | 0.0059 | | |
| 246 | 1a-5-38 | 0.0108 | | |
| 247 | 1a-5-39 | 0.0035 | | |
| 267 | 1a-2-66 | 1.5 | 1b-2-66 | 0.011 |

TABLE 54

| Example No. | Compound No. | IC$_{50}$ ($\mu$M) |
|---|---|---|
| 252 | 1-252 | 0.24 |
| 253 | 1-253 | 0.000039 |
| 254 | 1-254 | 0.00063 |
| 255 | 1-255 | 0.529 |
| 256 | 1-256 | 0.601 |
| 257 | 1-257 | 0.776 |
| 258 | 1-258 | 0.908 |
| 259 | 1-259 | 0.130 |
| 260 | 1-260 | 0.159 |
| 261 | 1-260 | 0.182 |

The compound of the present invention showed strong activity for inhibiting type IV collagenase.

Industrial Applicability

It is considered that the compound of the present invention is useful to prevent or treat osteoarthritis, rheumatoid arthritis, corneal ulceration, periodontal disease, metastasis and invasion of tumor, advanced virus infection (e.g., HIV), arteriosclerosis obliterans, arteriosclerotic aneurysm, atherosclerosis, restenosis, sepsis, septic shock, coronary thrombosis, aberrant angiogenesis, scleritis, multiple sclerosis, open angle glaucoma, retinopathies, proliferative retinopathy, neovascular glaucoma, pterygium, keratitis, epidermolysis bullosa, psoriasis, diabetes, nephritis, neurodegengerative disease, gingivitis, tumor growth, tumor angiogenesis, ocular tumor, angiofibroma, hemangioma, fever, hemorrhage, coagulation, cachexia, anorexia, acute infection, shock, autoimmune disease, malaria, Crohn disease, meningitis, and gastric ulcer, because the compound of the present invention has strong inhibitory activity against metalloproteinase, especially MMP.

What is claimed is:

1. A method for inhibiting metalloproteinase using a compound of the formula:

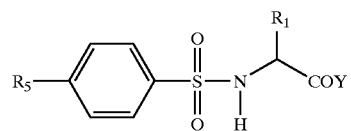

R$_1$ is lower alkyl optionally substituted with one or more substituents selected from the group consisting of phenyl and heteroaryl;

R$_5$ is a thioalkyl substituted phenyl group; and

Y is —NHOH or —OH;

or a pharmaceutically acceptable salt or hydrate thereof.

2. The method of claim 1, wherein R$_1$ is isopropyl.

3. The method of claim 1, wherein Y—OH.

4. The method of claim 1, wherein said thioalkyl group is a thiomethyl group.

5. The method of claim 1, wherein said compound is selected from the group consisting of 3-methyl-2-(4'-methylthiobiphenyl-4-sulfonylamino)-butyric acid, 2-(4'-methylthiobiphenyl-4-sulfonylamino)-3-phenyl-propionic acid and 3-(1H-indol-3-yl)-2-(4'-methylthiobiphenyl-4-sulfonylamino)-propionic acid.

6. A compound of the formula:

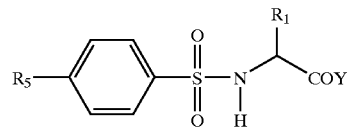

R$_1$ is lower alkyl optionally substituted with one or more substituents selected from the group consisting of phenyl and heteroaryl;

R$_5$ is a thioalkyl substituted phenyl group; and

Y is —NHOH or —OH;

or a pharmaceutically acceptable salt or hydrate thereof.

7. The compound of claim 6, wherein R$_1$ is isopropyl.

8. The compound of claim 6, wherein Y—OH.

9. The compound of claim 6, wherein said thioalkyl group is a thiomethyl group.

10. The compound of claim 6, wherein said compound is selected from the group consisting of 3-methyl-2-(4'-methylthiobiphenyl-4-sulfonylamino)-butyric acid, 2-(4'-methylthiobiphenyl-4-sulfonylamino)-3-phenyl-propionic acid and 3-(1H-indol-3-yl)-2-(4'-methylthiobiphenyl-4-sulfonylamino)-propionic acid.

11. A composition comprising the compound of claim 6 and a pharmaceutically acceptable carrier or excipient.

* * * * *